US011598780B2

(12) United States Patent
Nakamura et al.

(10) Patent No.: US 11,598,780 B2
(45) Date of Patent: Mar. 7, 2023

(54) ENGINEERING LYMPHOCYTES WITH SPECIFIC ALPHA AND BETA CHAINS ON THEIR T-CELL RECEPTOR

(71) Applicants: The University of Chicago, Chicago, IL (US); OncoTherapy Science, Inc., Kawaski (JP)

(72) Inventors: Yusuke Nakamura, Chicago, IL (US); Jae-Hyun Park, Chicago, IL (US); Sachiko Yoshimura, Tokyo (JP); Tetsuro Hikichi, Yokohama (JP)

(73) Assignees: The University of Chicago, Chicago, IL (US); Onco Therapy Science, Inc.

( * ) Notice: Subject to any disclaimer, the term of this patent is extended or adjusted under 35 U.S.C. 154(b) by 394 days.

(21) Appl. No.: 16/753,684

(22) PCT Filed: Oct. 5, 2018

(86) PCT No.: PCT/US2018/054664
§ 371 (c)(1),
(2) Date: Apr. 3, 2020

(87) PCT Pub. No.: WO2019/071164
PCT Pub. Date: Apr. 11, 2019

(65) Prior Publication Data
US 2020/0341001 A1 Oct. 29, 2020

Related U.S. Application Data

(60) Provisional application No. 62/569,215, filed on Oct. 6, 2017.

(51) Int. Cl.
| | | |
|---|---|---|
| *G01N 33/68* | (2006.01) | |
| *A61K 35/17* | (2015.01) | |
| *C07K 14/725* | (2006.01) | |
| *C12N 5/0783* | (2010.01) | |
| *C12N 15/85* | (2006.01) | |
| *G01N 33/50* | (2006.01) | |
| *G01N 33/569* | (2006.01) | |

(52) U.S. Cl.
CPC ......... *G01N 33/6818* (2013.01); *A61K 35/17* (2013.01); *C07K 14/7051* (2013.01); *C12N 5/0636* (2013.01); *C12N 15/85* (2013.01); *G01N 33/5005* (2013.01); *G01N 33/56966* (2013.01); *C12N 2510/00* (2013.01)

(58) Field of Classification Search
CPC .............. C12N 2510/00; C12N 5/0636; G01N 33/5005; G01N 33/6818; C07K 14/7051; A61K 35/17
See application file for complete search history.

(56) References Cited

U.S. PATENT DOCUMENTS

| | | |
|---|---|---|
| 4,816,567 A | 3/1989 | Cabilly et al. |
| 4,946,778 A | 8/1990 | Ladner et al. |
| 5,260,203 A | 11/1993 | Ladner et al. |
| 5,695,934 A | 12/1997 | Brenner |
| 5,714,330 A | 2/1998 | Brenner et al. |
| 5,750,341 A | 5/1998 | Macevicz |
| 6,306,597 B1 | 10/2001 | Macevicz |
| 6,432,360 B1 | 8/2002 | Church |
| 6,485,944 B1 | 11/2002 | Church et al. |
| 6,511,803 B1 | 1/2003 | Church et al. |
| 6,787,308 B2 | 9/2004 | Balasubramanian et al. |
| 6,818,395 B1 | 11/2004 | Quake et al. |
| 6,833,246 B2 | 12/2004 | Balasubramanian |
| 7,169,560 B2 | 1/2007 | Lapidus et al. |
| 7,282,337 B1 | 10/2007 | Harris |
| 2002/0164629 A1 | 11/2002 | Quake et al. |
| 2005/0130173 A1 | 6/2005 | Leamon et al. |
| 2009/0026082 A1 | 1/2009 | Rothberg et al. |
| 2009/0127589 A1 | 5/2009 | Rothberg et al. |
| 2009/0191565 A1 | 7/2009 | Lapidus et al. |
| 2010/0035252 A1 | 2/2010 | Rothberg et al. |
| 2010/0137143 A1 | 6/2010 | Rothberg et al. |
| 2010/0188073 A1 | 7/2010 | Rothberg et al. |
| 2010/0197507 A1 | 8/2010 | Rothberg et al. |
| 2010/0282617 A1 | 11/2010 | Rothberg et al. |
| 2010/0297093 A1 | 11/2010 | Robbins et al. |

(Continued)

FOREIGN PATENT DOCUMENTS

| | | |
|---|---|---|
| WO | WO 88/01649 | 3/1988 |
| WO | WO 00/018957 | 4/2000 |
| WO | WO 2006/084132 | 8/2006 |
| WO | WO 2017/089768 | 6/2017 |
| WO | WO 2017/161092 | 9/2017 |

OTHER PUBLICATIONS

Adessi et al., Solid phase DNA amplification: characterisation of primer attachment and amplification mechanisms. Nucleic Acids Res. Oct. 15, 2000;28(20):E87. 8 pages.

(Continued)

*Primary Examiner* — Elly-Gerald Stoica
(74) *Attorney, Agent, or Firm* — Casimir Jones SC; David W. Staple

(57) ABSTRACT

Provided herein are methods to identify TCR-recognizing cancer-specific antigens, and TCR-engineered T cells having antigen-specific cytotoxic activity. Provided herein are engineered T lymphocytes produced by the methods described herein. Provided herein are methods of treating cancer in a subject comprising administering the engineered T lymphocytes described herein. Provided herein are antibodies, or fragments thereof, produced by the methods described herein. Provided herein are methods of treating cancer in a subject comprising administering the antibodies described herein to a subject. In some embodiments, the therapeutic compositions (e.g., engineered lymphocytes, antibodies, etc.) and methods herein are provided as part of a kit or system.

11 Claims, 14 Drawing Sheets

Specification includes a Sequence Listing.

(56) References Cited

U.S. PATENT DOCUMENTS

| | | |
|---|---|---|
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2015/0337369 A1 | 11/2015 | Davis et al. |
| 2016/0289760 A1 | 10/2016 | Suzuki et al. |
| 2017/0107490 A1 | 4/2017 | Maeurer |
| 2017/0218042 A1 | 8/2017 | Tran et al. |

OTHER PUBLICATIONS

Bektas et al., Tight correlation between expression of the Forkhead transcription factor FOXM1 and HER2 in human breast cancer. BMC Cancer. Feb. 6, 2008;8:42.
Bennett et al., Toward the 1,000 dollars human genome. Pharmacogenomics. Jun. 2005;6(4):373-82.
Braslaysky et al., Sequence information can be obtained from single DNA molecules. Proc Natl Acad Sci U S A. Apr. 1, 2003;100(7):3960-4.
Brenner et al., Gene expression analysis by massively parallel signature sequencing (MPSS) on microbead arrays. Nat Biotechnol. Jun. 2000;18(6):630-4.
Clackson et al., Making antibody fragments using phage display libraries. Nature. Aug. 15, 1991;352(6336):624-8.
Coulie et al., Tumour antigens recognized by T lymphocytes: at the core of cancer immunotherapy. Nat Rev Cancer. Feb. 2014;14(2):135-46.
Dudley et al., Cancer regression and autoimmunity in patients after clonal repopulation with antitumor lymphocytes. Science. Oct. 25, 2002;298(5594):850-4.
Engels et al., Long-term persistence of CD4(+) but rapid disappearance of CD8(+) T cells expressing an MHC class I-restricted TCR of nanomolar affinity. Mol Ther. Mar. 2012;20(3):652-60.
Fang et al., Quantitative T cell repertoire analysis by deep cDNA sequencing of T cell receptor α and β chains using next-generation sequencing (NGS). Oncoimmunology. Jan. 7, 2015;3(12):e968467. 13 pages.
Guo et al., Therapeutic cancer vaccines: past, present, and future. Adv Cancer Res. 2013;119:421-75.
Harlow et al., Antibodies: A Laboratory Manual. Cold Spring Harbor Laboratory. 1988. TOC only. 9 pages.
Harris et al., Single-molecule DNA sequencing of a viral genome. Science. Apr. 4, 2008;320(5872):106-9.
Hazama et al., A phase II study of five peptides combination with oxaliplatin-based chemotherapy as a first-line therapy for advanced colorectal cancer (FXV study). J Transl Med. Apr. 30, 2014;12:108.
Hinrichs et al., Exploiting the curative potential of adoptive T-cell therapy for cancer. Immunol Rev. Jan. 2014;257(1):56-71.
Hodi et al., Improved survival with ipilimumab in patients with metastatic melanoma. N Engl J Med. Aug. 19, 2010;363(8):711-23.
Hudson et al., Engineered antibodies. Nat Med. Jan. 2003;9(1):129-34.
Ishida et al., Induced expression of PD-1, a novel member of the immunoglobulin gene superfamily, upon programmed cell death. EMBO J. Nov. 1992;11(11):3887-95.
Jackson et al., Driving CAR T-cells forward. Nat Rev Clin Oncol. Jun. 2016;13(6):370-83.
Johnson et al., Gene therapy with human and mouse T-cell receptors mediates cancer regression and targets normal tissues expressing cognate antigen. Blood. Jul. 16, 2009;114(3):535-46.
Kato et al., Effective screening of T cells recognizing neoantigens and construction of T-cell receptor-engineered T cells. Oncotarget. Jan. 13, 2018;9(13):11009-11019.
Kohler et al., Continuous cultures of fused cells secreting antibody of predefined specificity. Nature. Aug. 7, 1975;256(5517):495-7.
Kono et al., Multicenter, phase II clinical trial of cancer vaccination for advanced esophageal cancer with three peptides derived from novel cancer-testis antigens. J Transl Med. Jul. 9, 2012; 10:141.
Krummel et al., CD28 and CTLA-4 have opposing effects on the response of T cells to stimulation. J Exp Med. Aug. 1, 1995;182(2):459-65.
Law, ed. ImmunoAssay: A Practical Guide, published by Taylor & Francis, Ltd., 2005 edition. TOC only. 4 pages.
Leisegang et al., Eradication of Large Solid Tumors by Gene Therapy with a T-Cell Receptor Targeting a Single Cancer-Specific Point Mutation. Clin Cancer Res. Jun. 1, 2016;22( 11 ):2734-43.
Lim et al., The Principles of Engineering Immune Cells to Treat Cancer. Cell. Feb. 9, 2017;168(4):724-740.
Maclean et al., Application of 'next-generation' sequencing technologies to microbial genetics. Nat Rev Microbiol. Apr. 2009;7(4):287-96.
Margulies et al., Genome sequencing in microfabricated high-density picolitre reactors. Nature. Sep. 15, 2005;437(7057):376-80.
Marks et al., By-passing immunization. Human antibodies from V-gene libraries displayed on phage. J Mol Biol. Dec. 5, 1991;222(3):581-97.
Matsuda et al., Abstract 625: Eradication of cancer cells by T-cell receptor-engineered Tcells targeting neoantigens/oncoantigens: Cancer Research. 2017. 4 pages.
Matsuda et al., Induction of Neoantigen-Specific Cytotoxic T Cells and Construction of T-cell Receptor-Engineered T Cells for Ovarian Cancer. Clin Cancer Res. Nov. 1, 2018;24(21):5357-5367.
Maude et al., Chimeric antigen receptor T cells for sustained remissions in leukemia. N Engl J Med. Oct. 16, 2014;371(16):1507-17.
Mitra et al., Fluorescent in situ sequencing on polymerase colonies. Anal Biochem. Sep. 1, 2003;320(1):55-65.
NAKAMURA. Immunopharmacogenomics. Springer, Tokyo, 2015. 162 pages.
Osawa et al., Identification of HLA-A24-restricted novel T Cell epitope peptides derived from P-cadherin and kinesin family member 20A. J Biomed Biotechnol. 2012;2012:848042. 11 pages.
Pardoll. The blockade of immune checkpoints in cancer immunotherapy. Nat Rev Cancer. Mar. 22, 2012;12(4):252-64.
Postow et al., Immune Checkpoint Blockade in Cancer Therapy. J Clin Oncol. Jun. 10, 2015;33(17):1974-82.
Rapoport et al., NY-ESO-1-specific TCR-engineered T cells mediate sustained antigen-specific antitumor effects in myeloma.Nat Med. Aug. 2015;21 (8):914-921.
Riddell et al., T-cell mediated rejection of gene-modified HIV-specific cytotoxic T lymphocytes in HIV-infected patients. Nat Med. Feb. 1996;2(2):216-23.
Rizvi et al., Cancer immunology. Mutational landscape determines sensitivity to PD-1 blockade in non-small cell lung cancer. Science. Apr. 3, 2015;348(6230):124-8.
Robbins et al., Tumor regression in patients with metastatic synovial cell sarcoma and melanoma using genetically engineered lymphocytes reactive with NY-ESO-1. J Clin Oncol. Mar. 1, 2011;29(7):917-24.
Rooney et al., Molecular and genetic properties of tumors associated with local immune cytolytic activity. Cell. Jan. 15, 2015;160(1-2):48-61.
Rosenberg et al., Durable complete responses in heavily pretreated patients with metastatic melanoma using T-cell transfer immunotherapy. Clin Cancer Res. Jul. 1, 2011;17(13):4550-7.
Schalper et al., In situ tumor PD-L1 mRNA expression is associated with increased TILs and better outcome in breast carcinomas. Clin Cancer Res. May 15, 2014;20(10):2773-82.
Shendure et al., Accurate multiplex polony sequencing of an evolved bacterial genome. Science. Sep. 9, 2005;309(5741):1728-32.
Soni et al., Progress toward ultrafast DNA sequencing using solid-state nanopores. Clin Chem. Nov. 2007;53(11):1996-2001.
Stevanović et al., Landscape of immunogenic tumor antigens in successful immunotherapy of virally induced epithelial cancer. Science. Apr. 14, 2017;356(6334):200-205.
Strønen et al., Targeting of cancer neoantigens with donor-derived T cell receptor repertoires. Science. Jun. 10, 2016;352(6291):1337-41.
Suda et al., Identification of secernin 1 as a novel immunotherapy target for gastric cancer using the expression profiles of cDNA microarray. Cancer Sci. May 2006;97(5):411-9.

(56) References Cited

OTHER PUBLICATIONS

Topalian et al., Safety, activity, and immune correlates of anti-PD-1 antibody in cancer. N Engl J Med. Jun. 28, 2012;366(26):2443-54.

Tran et al., Cancer immunotherapy based on mutation-specific CD4+ T cells in a patient with epithelial cancer. Science. May 9, 2014;344(6184):641-5.

Tran et al., T-Cell Transfer Therapy Targeting Mutant KRAS in Cancer. N Engl J Med. Dec. 8, 2016;375(23):2255-2262.

Tumeh et al., PD-1 blockade induces responses by inhibiting adaptive immune resistance. Nature. Nov. 27, 2014;515(7528):568-71.

Uchida et al., Ring finger protein 43 as a new target for cancer immunotherapy. Clin Cancer Res. Dec. 15, 2004;10(24):8577-86.

Van Der Bruggen et al., A gene encoding an antigen recognized by cytolytic T lymphocytes on a human melanoma. Science. Dec. 13, 1991;254(5038):1643-7.

Voelkerding et al., Next-generation sequencing: from basic research to diagnostics. Clin Chem. Apr. 2009;55(4):641-58.

Vonderheide et al., A translational bridge to cancer immunotherapy: exploiting costimulation and target antigens for active and passive T cell immunotherapy. Immunol Res. 2003;27(2-3):341-56.

Watanabe et al., Identification of immunoglobulin superfamily 11 (IGSF11) as a novel target for cancer immunotherapy of gastrointestinal and hepatocellular carcinomas. Cancer Sci. Aug. 2005;96(8):498-506.

Wen et al., Elevated expression of UBE2T exhibits oncogenic properties in human prostate cancer. Oncotarget. Sep. 22, 2015;6(28):25226-39.

Weng et al., FOXM1 and FOXQ1 Are Promising Prognostic Biomarkers and Novel Targets of Tumor-Suppressive miR-342 in Human Colorectal Cancer. Clin Cancer Res. Oct. 1, 2016;22(19):4947-4957.

Yarchoan et al., Targeting neoantigens to augment antitumour immunity. Nat Rev Cancer. Apr. 2017;17(4):209-222.

Yee et al., Recent advances in the use of 1-15 antigen-specific Tcells for the treatment of cancer. Update on Cancer Therapeutics, Elsevier, vol. 1, No. 3, 2006 p. 333-342.

Yoshimura et al., Identification of an HLA-A2-restricted epitope peptide derived from hypoxia-inducible protein 2 (HIG2). PLoS One. Jan. 8, 2014;9(1):e85267. 7 pages.

Yoshitake et al., Phase II clinical trial of multiple peptide vaccination for advaced head and neck cancer patients revealed induction of immune responses and improved OS. Clin Cancer Res. Jan. 15, 2015;21(2):312-21.

Yu et al., Ubiquitin-Conjugating Enzyme E2T is an Independent Prognostic Factor and Promotes Gastric Cancer Progression. Tumour Biol. Sep. 2016;37(9):11723-11732.

Extended European Search Report for PCT/US2018/054664, dated Apr. 14, 2021. 11 pages.

International Search Report and Written Opinion for PCT/US2018/054664, dated Jan. 22, 2019. 15 pages.

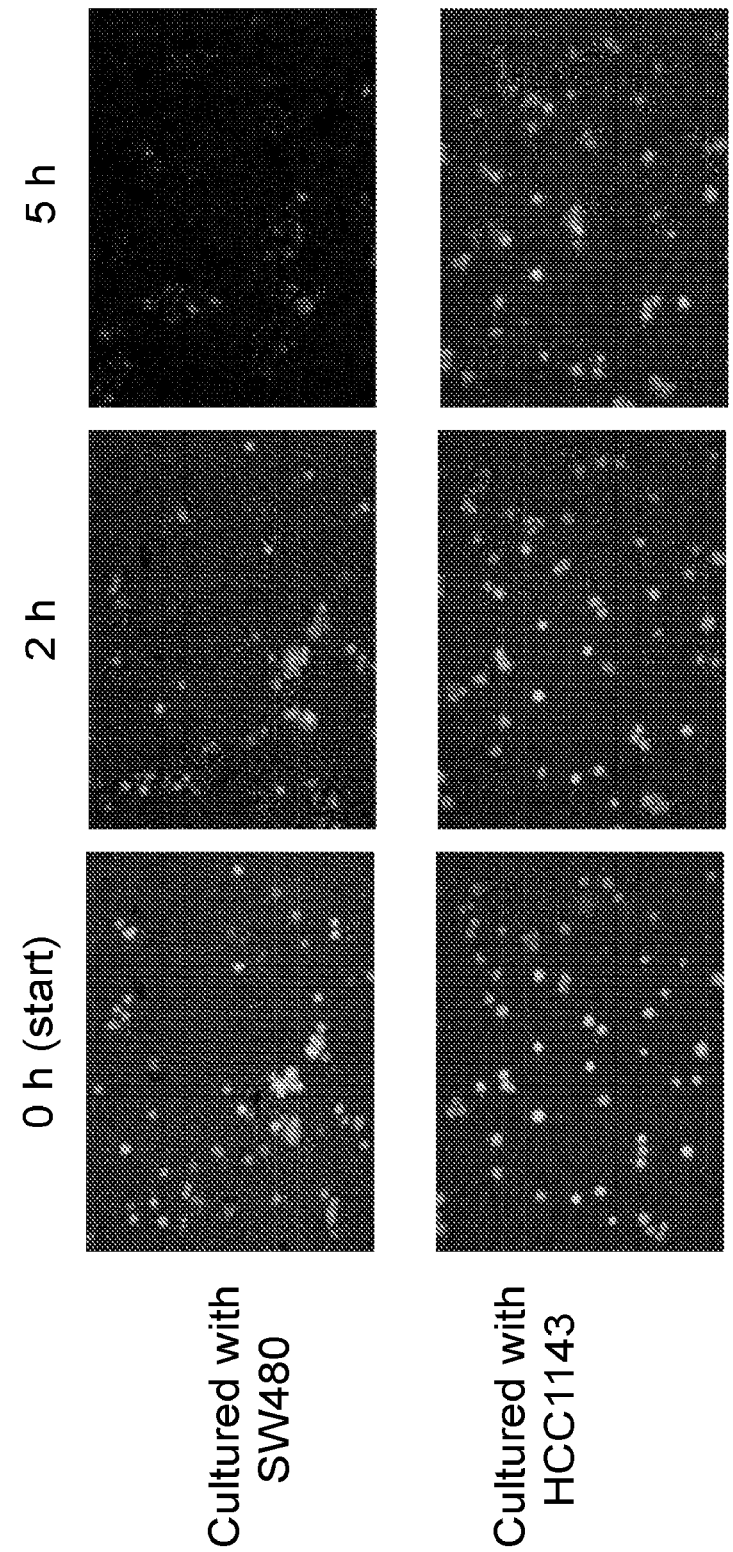

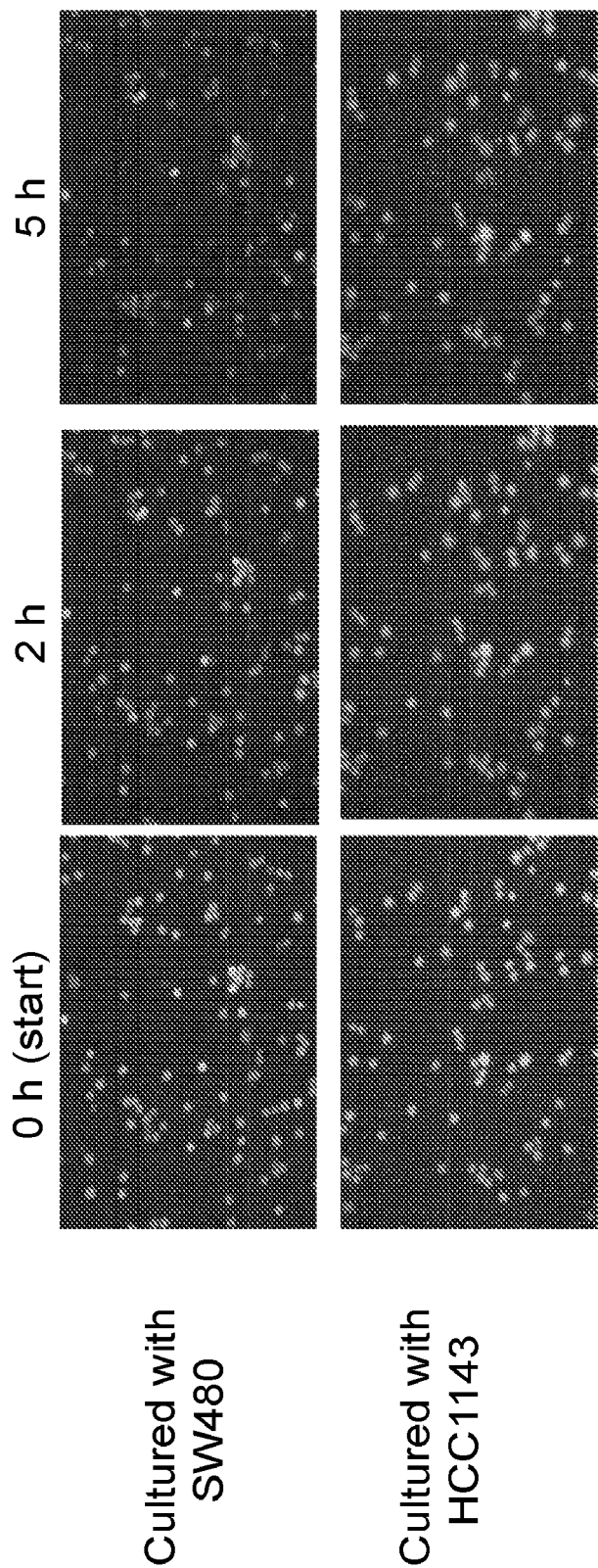

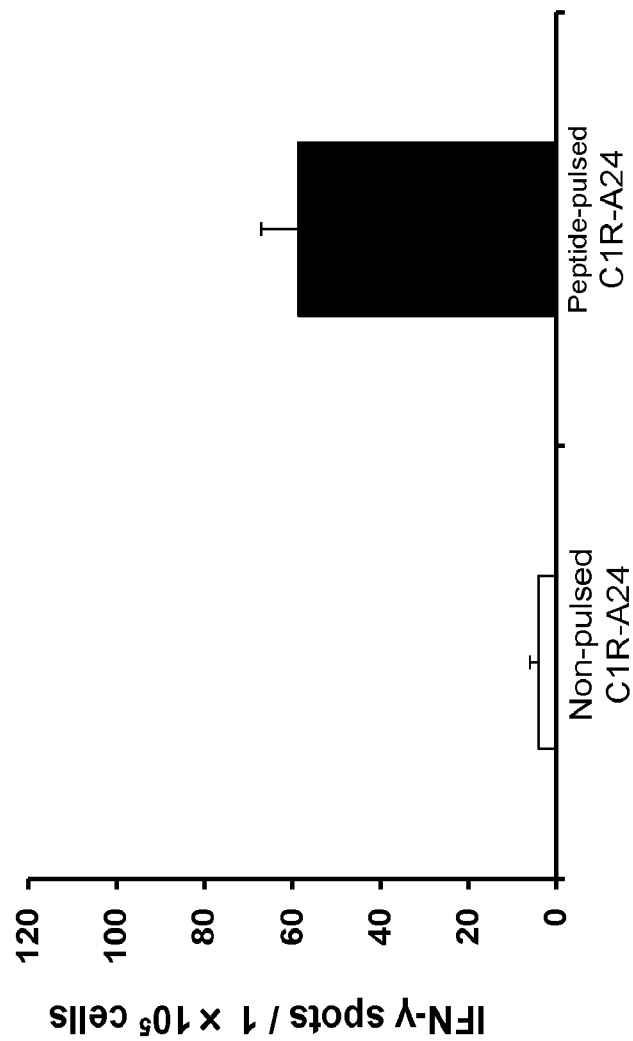

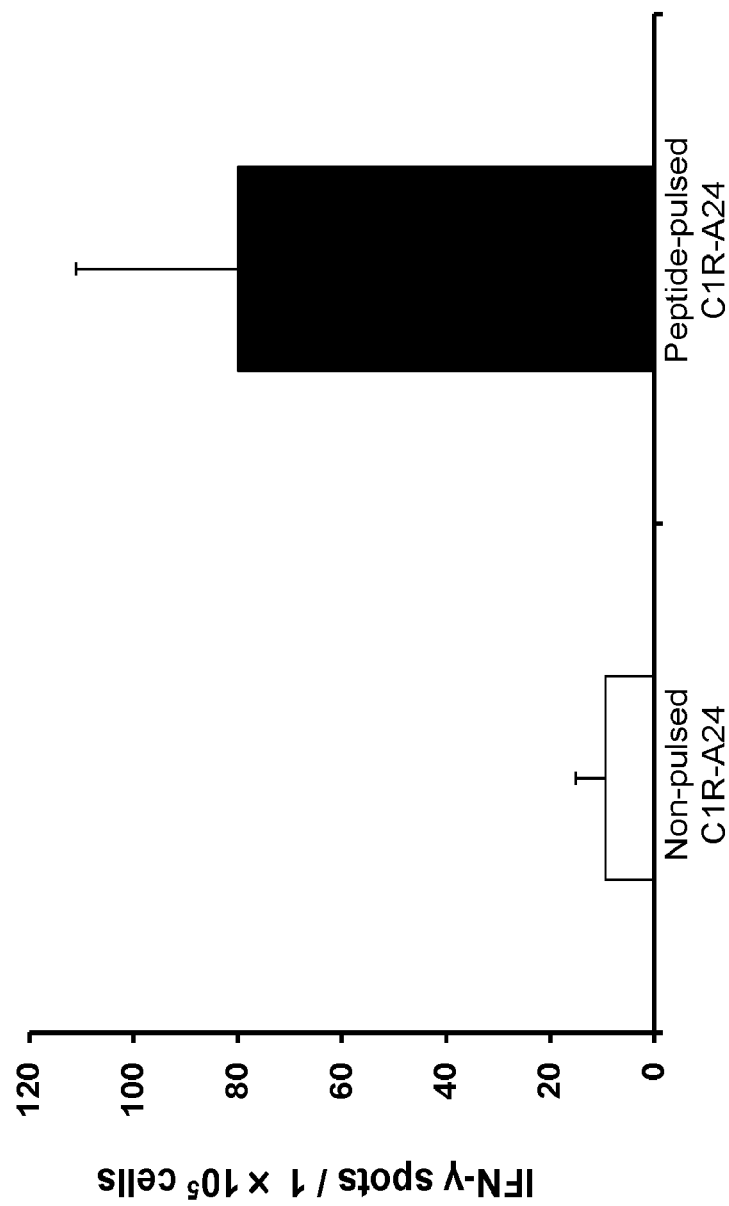

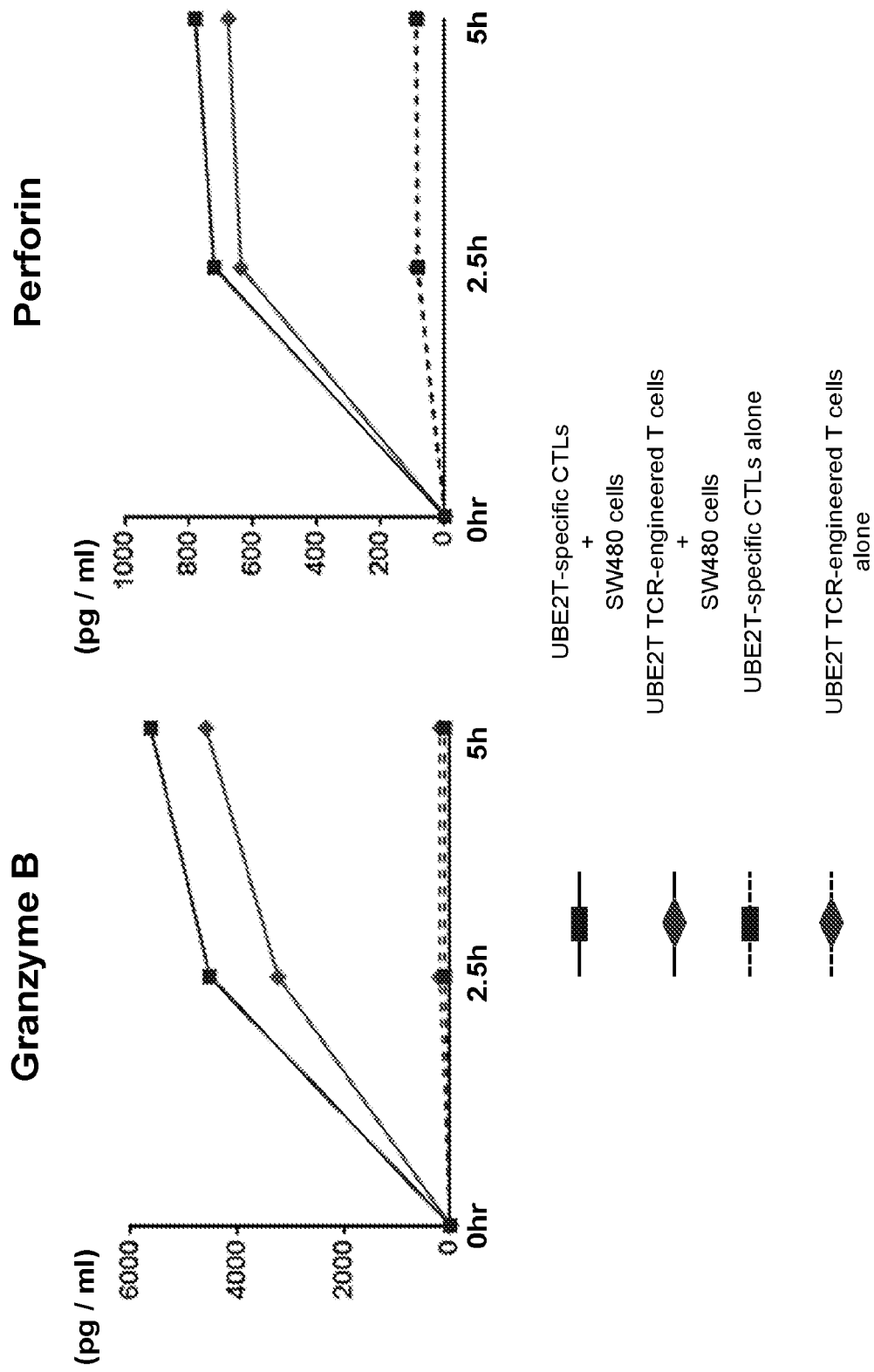

SEQUENCE LISTING

<160> NUMBER OF SEQ ID NOS: 132

<210> SEQ ID NO 1
<211> LENGTH: 10
<212> TYPE: PRT
<213> ORGANISM: Homo sapiens

<400> SEQUENCE: 1

Glu Trp Ala Ala Ala Met Asn Ala Glu Phe
1               5                   10

<210> SEQ ID NO 2
<211> LENGTH: 10
<212> TYPE: PRT
<213> ORGANISM: Homo sapiens

<400> SEQUENCE: 2

Asp Tyr Leu Asn Glu Trp Gly Ser Arg Phe
1               5                   10

<210> SEQ ID NO 3
<211> LENGTH: 9
<212> TYPE: PRT
<213> ORGANISM: Homo sapiens

<400> SEQUENCE: 3

Ile Tyr Thr Trp Ile Glu Asp His Phe
1               5

<210> SEQ ID NO 4
<211> LENGTH: 9
<212> TYPE: PRT
<213> ORGANISM: Homo sapiens

<400> SEQUENCE: 4

Lys Trp Leu Ile Ser Pro Val Lys Ile
1               5

<210> SEQ ID NO 5
<211> LENGTH: 9
<212> TYPE: PRT
<213> ORGANISM: Homo sapiens

<400> SEQUENCE: 5

Leu Tyr Leu Lys Leu Leu Pro Tyr Val
1               5

<210> SEQ ID NO 6
<211> LENGTH: 10
<212> TYPE: PRT
<213> ORGANISM: Homo sapiens

<400> SEQUENCE: 6

Lys Val Tyr Leu Arg Val Arg Pro Leu Leu
1               5                   10

<210> SEQ ID NO 7
<211> LENGTH: 9
<212> TYPE: PRT
<213> ORGANISM: Homo sapiens

<400> SEQUENCE: 7

Glu Tyr Cys Pro Gly Gly Asn Leu Phe
1               5

```
<210> SEQ ID NO 8
<211> LENGTH: 9
<212> TYPE: PRT
<213> ORGANISM: Homo sapiens

<400> SEQUENCE: 8

Glu Trp Ala Asp Leu Ser Phe Pro Phe
1               5

<210> SEQ ID NO 9
<211> LENGTH: 9
<212> TYPE: PRT
<213> ORGANISM: Homo sapiens

<400> SEQUENCE: 9

Asn Ser Gln Pro Val Trp Leu Cys Leu
1               5

<210> SEQ ID NO 10
<211> LENGTH: 10
<212> TYPE: PRT
<213> ORGANISM: Homo sapiens

<400> SEQUENCE: 10

Ala Tyr Asp Ile Gly Leu Phe Ala Tyr Phe
1               5                   10

<210> SEQ ID NO 11
<211> LENGTH: 9
<212> TYPE: PRT
<213> ORGANISM: Homo sapiens

<400> SEQUENCE: 11

Gln Tyr Cys Phe Glu Cys Asp Cys Phe
1               5

<210> SEQ ID NO 12
<211> LENGTH: 10
<212> TYPE: PRT
<213> ORGANISM: Homo sapiens

<400> SEQUENCE: 12

Ser Tyr Gln Lys Val Ile Glu Leu Phe Ser
1               5                   10

<210> SEQ ID NO 13
<211> LENGTH: 9
<212> TYPE: PRT
<213> ORGANISM: Homo sapiens

<400> SEQUENCE: 13

Arg Tyr Pro Phe Glu Pro Pro Gln Ile
1               5

<210> SEQ ID NO 14
<211> LENGTH: 9
<212> TYPE: PRT
<213> ORGANISM: Homo sapiens

<400> SEQUENCE: 14

Arg Tyr Leu Ser Ala Gly Pro Thr Leu
1               5
```

-continued

```
<210> SEQ ID NO 15
<211> LENGTH: 9
<212> TYPE: PRT
<213> ORGANISM: Homo sapiens

<400> SEQUENCE: 15

Ser Tyr Gly Val Leu Leu Trp Glu Ile
1               5

<210> SEQ ID NO 16
<211> LENGTH: 9
<212> TYPE: PRT
<213> ORGANISM: Homo sapiens

<400> SEQUENCE: 16

Arg Phe Val Pro Asp Gly Asn Arg Ile
1               5

<210> SEQ ID NO 17
<211> LENGTH: 9
<212> TYPE: PRT
<213> ORGANISM: Homo sapiens

<400> SEQUENCE: 17

Gly Tyr Ser Asn Thr Ala Thr Glu Trp
1               5

<210> SEQ ID NO 18
<211> LENGTH: 9
<212> TYPE: PRT
<213> ORGANISM: Homo sapiens

<400> SEQUENCE: 18

Ile Tyr Arg Val Ser Phe Thr Asp Phe
1               5

<210> SEQ ID NO 19
<211> LENGTH: 10
<212> TYPE: PRT
<213> ORGANISM: Homo sapiens

<400> SEQUENCE: 19

Ser Ile Ala Gly Gly Gln Ile Leu Ser Val
1               5                   10

<210> SEQ ID NO 20
<211> LENGTH: 9
<212> TYPE: PRT
<213> ORGANISM: Homo sapiens

<400> SEQUENCE: 20

Ser Leu Gln Lys Ala Leu His His Leu
1               5

<210> SEQ ID NO 21
<211> LENGTH: 10
<212> TYPE: PRT
<213> ORGANISM: Homo sapiens

<400> SEQUENCE: 21

Thr Leu Leu Ser Ile Tyr Ile Asp Gly Val
1               5                   10
```

```
<210> SEQ ID NO 22
<211> LENGTH: 9
<212> TYPE: PRT
<213> ORGANISM: Homo sapiens

<400> SEQUENCE: 22

Val Val Cys Ser Lys Leu Thr Glu Val
1               5

<210> SEQ ID NO 23
<211> LENGTH: 10
<212> TYPE: PRT
<213> ORGANISM: Homo sapiens

<400> SEQUENCE: 23

Ile Leu Val Val Cys Gly Tyr Ile Thr Val
1               5                   10

<210> SEQ ID NO 24
<211> LENGTH: 9
<212> TYPE: PRT
<213> ORGANISM: Homo sapiens

<400> SEQUENCE: 24

Leu Leu Ile Gly Ser Thr Ser Tyr Val
1               5

<210> SEQ ID NO 25
<211> LENGTH: 9
<212> TYPE: PRT
<213> ORGANISM: Homo sapiens

<400> SEQUENCE: 25

Ala Leu Val Trp Leu Ile Asp Cys Ile
1               5

<210> SEQ ID NO 26
<211> LENGTH: 9
<212> TYPE: PRT
<213> ORGANISM: Homo sapiens

<400> SEQUENCE: 26

Leu Leu Phe Asp Glu Tyr His Lys Leu
1               5

<210> SEQ ID NO 27
<211> LENGTH: 10
<212> TYPE: PRT
<213> ORGANISM: Homo sapiens

<400> SEQUENCE: 27

Tyr Ile Tyr Asp Leu Phe Val Pro Val Ser
1               5                   10

<210> SEQ ID NO 28
<211> LENGTH: 9
<212> TYPE: PRT
<213> ORGANISM: Homo sapiens

<400> SEQUENCE: 28

Arg Ile Ile Cys Glu Ala His Lys Val
1               5
```

```
<210> SEQ ID NO 29
<211> LENGTH: 9
<212> TYPE: PRT
<213> ORGANISM: Homo sapiens

<400> SEQUENCE: 29

Phe Gln Asn Ser Pro Pro Ala Ser Val
1               5

<210> SEQ ID NO 30
<211> LENGTH: 9
<212> TYPE: PRT
<213> ORGANISM: Homo sapiens

<400> SEQUENCE: 30

Arg Leu Ala Phe Asp Ile Met Arg Val
1               5

<210> SEQ ID NO 31
<211> LENGTH: 10
<212> TYPE: PRT
<213> ORGANISM: Homo sapiens

<400> SEQUENCE: 31

Thr Thr Met Trp Arg Ala Thr Thr Thr Val
1               5                   10

<210> SEQ ID NO 32
<211> LENGTH: 9
<212> TYPE: PRT
<213> ORGANISM: Homo sapiens

<400> SEQUENCE: 32

Ala Leu Tyr Gly Arg Ala Leu Arg Val
1               5

<210> SEQ ID NO 33
<211> LENGTH: 9
<212> TYPE: PRT
<213> ORGANISM: Homo sapiens

<400> SEQUENCE: 33

Ile Thr Asp Gln Tyr Ile Tyr Met Val
1               5

<210> SEQ ID NO 34
<211> LENGTH: 9
<212> TYPE: PRT
<213> ORGANISM: Homo sapiens

<400> SEQUENCE: 34

Gly Leu Gly Pro Gly Leu Leu Gly Val
1               5

<210> SEQ ID NO 35
<211> LENGTH: 9
<212> TYPE: PRT
<213> ORGANISM: Homo sapiens

<400> SEQUENCE: 35

Lys Cys Leu Asp Phe Ser Leu Val Val
1               5
```

```
<210> SEQ ID NO 36
<211> LENGTH: 9
<212> TYPE: PRT
<213> ORGANISM: Homo sapiens

<400> SEQUENCE: 36

Lys Thr Lys Arg Leu Asn Glu Leu Lys
1               5

<210> SEQ ID NO 37
<211> LENGTH: 9
<212> TYPE: PRT
<213> ORGANISM: Homo sapiens

<400> SEQUENCE: 37

Met Ser Gln Asn Val Asp Met Pro Lys
1               5

<210> SEQ ID NO 38
<211> LENGTH: 9
<212> TYPE: PRT
<213> ORGANISM: Homo sapiens

<400> SEQUENCE: 38

Val Val Ser Thr Ser Leu Glu Asp Lys
1               5

<210> SEQ ID NO 39
<211> LENGTH: 10
<212> TYPE: PRT
<213> ORGANISM: Homo sapiens

<400> SEQUENCE: 39

Ser Thr Ser Phe Glu Ile Ser Arg Asn Lys
1               5                   10

<210> SEQ ID NO 40
<211> LENGTH: 9
<212> TYPE: PRT
<213> ORGANISM: Homo sapiens

<400> SEQUENCE: 40

Glu Val Leu His Met Ile Tyr Met Arg
1               5

<210> SEQ ID NO 41
<211> LENGTH: 9
<212> TYPE: PRT
<213> ORGANISM: Homo sapiens

<400> SEQUENCE: 41

Trp Thr Ile His Pro Ser Ala Asn Arg
1               5

<210> SEQ ID NO 42
<211> LENGTH: 9
<212> TYPE: PRT
<213> ORGANISM: Homo sapiens

<400> SEQUENCE: 42

Glu Phe Thr Gln Tyr Trp Ala Gln Arg
1               5
```

```
<210> SEQ ID NO 43
<211> LENGTH: 9
<212> TYPE: PRT
<213> ORGANISM: Homo sapiens

<400> SEQUENCE: 43

Ile Tyr Val Tyr Val Gln Asp Tyr Arg
1               5

<210> SEQ ID NO 44
<211> LENGTH: 10
<212> TYPE: PRT
<213> ORGANISM: Homo sapiens

<400> SEQUENCE: 44

Ala Val Val Asn Val Thr Tyr Ser Ser Lys
1               5                   10

<210> SEQ ID NO 45
<211> LENGTH: 12
<212> TYPE: PRT
<213> ORGANISM: Artificial sequence
<220> FEATURE:
<223> OTHER INFORMATION: Synthetic peptide

<400> SEQUENCE: 45

Cys Ala Ala Leu Asp Ser Asn Tyr Gln Leu Ile Trp
1               5                   10

<210> SEQ ID NO 46
<211> LENGTH: 16
<212> TYPE: PRT
<213> ORGANISM: Artificial sequence
<220> FEATURE:
<223> OTHER INFORMATION: Synthetic peptide

<400> SEQUENCE: 46

Cys Ala Ser Ser Lys Asn Gly Gly Ser Tyr Lys Asn Glu Gln Phe Phe
1               5                   10                  15

<210> SEQ ID NO 47
<211> LENGTH: 17
<212> TYPE: PRT
<213> ORGANISM: Artificial sequence
<220> FEATURE:
<223> OTHER INFORMATION: Synthetic peptide

<400> SEQUENCE: 47

Cys Ala Met Arg Glu Val Leu Ser Gly Gly Ala Asp Gly Leu Thr
1               5                   10                  15

Phe

<210> SEQ ID NO 48
<211> LENGTH: 15
<212> TYPE: PRT
<213> ORGANISM: Artificial sequence
<220> FEATURE:
<223> OTHER INFORMATION: Synthetic peptide

<400> SEQUENCE: 48

Cys Ala Ser Ser Pro Leu Ile Asp Thr Asn Gln Pro Gln His Phe
1               5                   10                  15
```

```
<210> SEQ ID NO 49
<211> LENGTH: 15
<212> TYPE: PRT
<213> ORGANISM: Artificial sequence
<220> FEATURE:
<223> OTHER INFORMATION: Synthetic peptide

<400> SEQUENCE: 49

Cys Ala Cys Pro Ile Met Trp Gly Ser Asn Tyr Lys Leu Thr Phe
1               5                   10                  15

<210> SEQ ID NO 50
<211> LENGTH: 12
<212> TYPE: PRT
<213> ORGANISM: Artificial sequence
<220> FEATURE:
<223> OTHER INFORMATION: Synthetic peptide

<400> SEQUENCE: 50

Cys Ala Ser Ser Leu Arg Val His Glu Gln Tyr Phe
1               5                   10

<210> SEQ ID NO 51
<211> LENGTH: 16
<212> TYPE: PRT
<213> ORGANISM: Artificial sequence
<220> FEATURE:
<223> OTHER INFORMATION: Synthetic peptide

<400> SEQUENCE: 51

Cys Ala Met Arg Glu Ala Leu Ser Tyr Asn Thr Asp Lys Leu Ile Phe
1               5                   10                  15

<210> SEQ ID NO 52
<211> LENGTH: 12
<212> TYPE: PRT
<213> ORGANISM: Artificial sequence
<220> FEATURE:
<223> OTHER INFORMATION: Synthetic peptide

<400> SEQUENCE: 52

Cys Ala Ser Arg Glu Tyr Lys Asn Glu Gln Phe Phe
1               5                   10

<210> SEQ ID NO 53
<211> LENGTH: 15
<212> TYPE: PRT
<213> ORGANISM: Artificial sequence
<220> FEATURE:
<223> OTHER INFORMATION: Synthetic peptide

<400> SEQUENCE: 53

Cys Ala Pro Ser Gly Ser Gly Ala Gly Ser Tyr Gln Leu Thr Phe
1               5                   10                  15

<210> SEQ ID NO 54
<211> LENGTH: 12
<212> TYPE: PRT
<213> ORGANISM: Artificial sequence
<220> FEATURE:
<223> OTHER INFORMATION: Synthetic peptide

<400> SEQUENCE: 54

Cys Ala Ser Ser Phe Ser Ile Asp Thr Gln Tyr Phe
1               5                   10
```

```
<210> SEQ ID NO 55
<211> LENGTH: 14
<212> TYPE: PRT
<213> ORGANISM: Artificial sequence
<220> FEATURE:
<223> OTHER INFORMATION: Synthetic peptide

<400> SEQUENCE: 55

Cys Ala Val Ile Gly Gly Gly Ser Asn Tyr Gln Leu Ile Trp
1               5                   10

<210> SEQ ID NO 56
<211> LENGTH: 15
<212> TYPE: PRT
<213> ORGANISM: Artificial sequence
<220> FEATURE:
<223> OTHER INFORMATION: Synthetic peptide

<400> SEQUENCE: 56

Cys Ala Ser Ser Pro Ser Pro Leu Asp Trp Glu Thr Gln Tyr Phe
1               5                   10                  15

<210> SEQ ID NO 57
<211> LENGTH: 13
<212> TYPE: PRT
<213> ORGANISM: Artificial sequence
<220> FEATURE:
<223> OTHER INFORMATION: Synthetic peptide

<400> SEQUENCE: 57

Cys Ala Gly Arg Asn Ser Gly Thr Tyr Lys Tyr Ile Phe
1               5                   10

<210> SEQ ID NO 58
<211> LENGTH: 14
<212> TYPE: PRT
<213> ORGANISM: Artificial sequence
<220> FEATURE:
<223> OTHER INFORMATION: Synthetic peptide

<400> SEQUENCE: 58

Cys Ala Ser Ser Leu Gly Thr Pro Lys Glu Thr Gln Tyr Phe
1               5                   10

<210> SEQ ID NO 59
<211> LENGTH: 16
<212> TYPE: PRT
<213> ORGANISM: Artificial sequence
<220> FEATURE:
<223> OTHER INFORMATION: Synthetic peptide

<400> SEQUENCE: 59

Cys Ala Ala Arg Gly Tyr Ser Gly Ala Gly Ser Tyr Gln Leu Thr Phe
1               5                   10                  15

<210> SEQ ID NO 60
<211> LENGTH: 12
<212> TYPE: PRT
<213> ORGANISM: Artificial sequence
<220> FEATURE:
<223> OTHER INFORMATION: Synthetic peptide

<400> SEQUENCE: 60

Cys Ala Ser Arg Gln Gly Gly Thr Pro Leu His Phe
1               5                   10
```

```
<210> SEQ ID NO 61
<211> LENGTH: 11
<212> TYPE: PRT
<213> ORGANISM: Artificial sequence
<220> FEATURE:
<223> OTHER INFORMATION: Synthetic peptide

<400> SEQUENCE: 61

Cys Ala Val Arg Arg Gly Asn Gln Phe Tyr Phe
1               5                   10

<210> SEQ ID NO 62
<211> LENGTH: 17
<212> TYPE: PRT
<213> ORGANISM: Artificial sequence
<220> FEATURE:
<223> OTHER INFORMATION: Synthetic peptide

<400> SEQUENCE: 62

Cys Ala Ser Ser Leu Ala Leu Gln Gly Met Val Ser Thr Glu Ala Phe
1               5                   10                  15

Phe

<210> SEQ ID NO 63
<211> LENGTH: 13
<212> TYPE: PRT
<213> ORGANISM: Artificial sequence
<220> FEATURE:
<223> OTHER INFORMATION: Synthetic peptide

<400> SEQUENCE: 63

Cys Ala Val Asp Met Trp Ser Gln Gly Asn Leu Ile Phe
1               5                   10

<210> SEQ ID NO 64
<211> LENGTH: 14
<212> TYPE: PRT
<213> ORGANISM: Artificial sequence
<220> FEATURE:
<223> OTHER INFORMATION: Synthetic peptide

<400> SEQUENCE: 64

Cys Ala Ser Ser Leu Gly Thr Gly Asp Tyr Glu Gln Tyr Phe
1               5                   10

<210> SEQ ID NO 65
<211> LENGTH: 16
<212> TYPE: PRT
<213> ORGANISM: Artificial sequence
<220> FEATURE:
<223> OTHER INFORMATION: Synthetic peptide

<400> SEQUENCE: 65

Cys Ala Val Arg Asp Ile Glu Ala Gly Gly Ser Tyr Ile Pro Thr Phe
1               5                   10                  15

<210> SEQ ID NO 66
<211> LENGTH: 15
<212> TYPE: PRT
<213> ORGANISM: Artificial sequence
<220> FEATURE:
<223> OTHER INFORMATION: Synthetic peptide

<400> SEQUENCE: 66

Cys Ala Ser Ser Val Gly Trp Thr Ser Ser Tyr Glu Gln Tyr Phe
1               5                   10                  15
```

```
<210> SEQ ID NO 67
<211> LENGTH: 12
<212> TYPE: PRT
<213> ORGANISM: Artificial sequence
<220> FEATURE:
<223> OTHER INFORMATION: Synthetic peptide

<400> SEQUENCE: 67

Cys Ala Val Glu Ala Gly Tyr Ser Thr Leu Thr Phe
1               5                   10

<210> SEQ ID NO 68
<211> LENGTH: 7
<212> TYPE: PRT
<213> ORGANISM: Artificial sequence
<220> FEATURE:
<223> OTHER INFORMATION: Synthetic peptide

<400> SEQUENCE: 68

Cys Ala Ser Gly Ala Phe Phe
1               5

<210> SEQ ID NO 69
<211> LENGTH: 14
<212> TYPE: PRT
<213> ORGANISM: Artificial sequence
<220> FEATURE:
<223> OTHER INFORMATION: Synthetic peptide

<400> SEQUENCE: 69

Cys Ala Met Arg Glu Gly Arg Asn Phe Asn Lys Phe Tyr Phe
1               5                   10

<210> SEQ ID NO 70
<211> LENGTH: 14
<212> TYPE: PRT
<213> ORGANISM: Artificial sequence
<220> FEATURE:
<223> OTHER INFORMATION: Synthetic peptide

<400> SEQUENCE: 70

Cys Ala Ser Ser Leu Ser Gly Gly Pro Asn Glu Gln Phe Phe
1               5                   10

<210> SEQ ID NO 71
<211> LENGTH: 13
<212> TYPE: PRT
<213> ORGANISM: Artificial sequence
<220> FEATURE:
<223> OTHER INFORMATION: Synthetic peptide

<400> SEQUENCE: 71

Cys Ala Met Arg Glu Val Thr Gly Asn Gln Phe Tyr Phe
1               5                   10

<210> SEQ ID NO 72
<211> LENGTH: 17
<212> TYPE: PRT
<213> ORGANISM: Artificial sequence
<220> FEATURE:
<223> OTHER INFORMATION: Synthetic peptide

<400> SEQUENCE: 72

Cys Ala Ser Ser Gln Lys Ser Gly Pro Leu Lys Arg Gln Pro Gln His
1               5                   10                  15

Phe
```

```
<210> SEQ ID NO 73
<211> LENGTH: 13
<212> TYPE: PRT
<213> ORGANISM: Artificial sequence
<220> FEATURE:
<223> OTHER INFORMATION: Synthetic peptide

<400> SEQUENCE: 73

Cys Ala Val Arg Ala Gly Ala Gly Asn Met Leu Thr Phe
1               5                   10

<210> SEQ ID NO 74
<211> LENGTH: 14
<212> TYPE: PRT
<213> ORGANISM: Artificial sequence
<220> FEATURE:
<223> OTHER INFORMATION: Synthetic peptide

<400> SEQUENCE: 74

Cys Ala Ser Ser Ile Asp Gly Leu Ala Gly Glu Gln Tyr Phe
1               5                   10

<210> SEQ ID NO 75
<211> LENGTH: 12
<212> TYPE: PRT
<213> ORGANISM: Artificial sequence
<220> FEATURE:
<223> OTHER INFORMATION: Synthetic peptide

<400> SEQUENCE: 75

Cys Ala Met Ser Gln Tyr Gly Asn Lys Leu Val Phe
1               5                   10

<210> SEQ ID NO 76
<211> LENGTH: 14
<212> TYPE: PRT
<213> ORGANISM: Artificial sequence
<220> FEATURE:
<223> OTHER INFORMATION: Synthetic peptide

<400> SEQUENCE: 76

Cys Ala Ser Ser Glu Ile Arg Asn Ala Tyr Glu Gln Tyr Phe
1               5                   10

<210> SEQ ID NO 77
<211> LENGTH: 13
<212> TYPE: PRT
<213> ORGANISM: Artificial sequence
<220> FEATURE:
<223> OTHER INFORMATION: Synthetic peptide

<400> SEQUENCE: 77

Cys Ala Val Arg Gly Gly Ser Asn Tyr Gln Leu Ile Trp
1               5                   10

<210> SEQ ID NO 78
<211> LENGTH: 16
<212> TYPE: PRT
<213> ORGANISM: Artificial sequence
<220> FEATURE:
<223> OTHER INFORMATION: Synthetic peptide

<400> SEQUENCE: 78

Cys Ala Ser Ser Ser Ser Ser Gly Thr Pro Trp Asn Glu Gln Phe Phe
1               5                   10                  15
```

```
<210> SEQ ID NO 79
<211> LENGTH: 11
<212> TYPE: PRT
<213> ORGANISM: Artificial sequence
<220> FEATURE:
<223> OTHER INFORMATION: Synthetic peptide

<400> SEQUENCE: 79

Cys Ala Thr Val Asn Asp Tyr Lys Leu Ser Phe
1               5                   10

<210> SEQ ID NO 80
<211> LENGTH: 15
<212> TYPE: PRT
<213> ORGANISM: Artificial sequence
<220> FEATURE:
<223> OTHER INFORMATION: Synthetic peptide

<400> SEQUENCE: 80

Cys Ala Ser Ser Leu Val Leu Gly Arg Asn Thr Glu Ala Phe Phe
1               5                   10                  15

<210> SEQ ID NO 81
<211> LENGTH: 14
<212> TYPE: PRT
<213> ORGANISM: Artificial sequence
<220> FEATURE:
<223> OTHER INFORMATION: Synthetic peptide

<400> SEQUENCE: 81

Cys Leu Val Gly Asp Arg Gln Ala Gly Thr Ala Leu Ile Phe
1               5                   10

<210> SEQ ID NO 82
<211> LENGTH: 15
<212> TYPE: PRT
<213> ORGANISM: Artificial sequence
<220> FEATURE:
<223> OTHER INFORMATION: Synthetic peptide

<400> SEQUENCE: 82

Cys Ser Val Glu Gly Ser Leu Gly Gly Arg Asp Glu Gln Phe Phe
1               5                   10                  15

<210> SEQ ID NO 83
<211> LENGTH: 15
<212> TYPE: PRT
<213> ORGANISM: Artificial sequence
<220> FEATURE:
<223> OTHER INFORMATION: Synthetic peptide

<400> SEQUENCE: 83

Cys Ala Met Arg Glu Arg Ser Gly Gly Ser Tyr Ile Pro Thr Phe
1               5                   10                  15

<210> SEQ ID NO 84
<211> LENGTH: 14
<212> TYPE: PRT
<213> ORGANISM: Artificial sequence
<220> FEATURE:
<223> OTHER INFORMATION: Synthetic peptide

<400> SEQUENCE: 84

Cys Ala Ser Lys Gly Thr Gly Gln Lys Glu Thr Gln Tyr Phe
1               5                   10
```

```
<210> SEQ ID NO 85
<211> LENGTH: 15
<212> TYPE: PRT
<213> ORGANISM: Artificial sequence
<220> FEATURE:
<223> OTHER INFORMATION: Synthetic peptide

<400> SEQUENCE: 85

Cys Ala Glu Thr Asp Thr Thr Ser Gly Thr Tyr Lys Tyr Ile Phe
1               5                   10                  15

<210> SEQ ID NO 86
<211> LENGTH: 17
<212> TYPE: PRT
<213> ORGANISM: Artificial sequence
<220> FEATURE:
<223> OTHER INFORMATION: Synthetic peptide

<400> SEQUENCE: 86

Cys Ala Ser Ser Leu Phe Ala Gln Ser Ser Tyr Lys Asn Glu Gln Phe
1               5                   10                  15

Phe

<210> SEQ ID NO 87
<211> LENGTH: 18
<212> TYPE: PRT
<213> ORGANISM: Artificial sequence
<220> FEATURE:
<223> OTHER INFORMATION: Synthetic peptide

<400> SEQUENCE: 87

Cys Ala Ala Ser Ala Glu Gly Ala Gly Gly Thr Ser Tyr Gly Lys Leu
1               5                   10                  15

Thr Phe

<210> SEQ ID NO 88
<211> LENGTH: 13
<212> TYPE: PRT
<213> ORGANISM: Artificial sequence
<220> FEATURE:
<223> OTHER INFORMATION: Synthetic peptide

<400> SEQUENCE: 88

Cys Ala Ser Ser Leu Leu Lys Asn Thr Glu Ala Phe Phe
1               5                   10

<210> SEQ ID NO 89
<211> LENGTH: 13
<212> TYPE: PRT
<213> ORGANISM: Artificial sequence
<220> FEATURE:
<223> OTHER INFORMATION: Synthetic peptide

<400> SEQUENCE: 89

Cys Ala Val His Asp Asn Tyr Gly Gln Asn Phe Val Phe
1               5                   10

<210> SEQ ID NO 90
<211> LENGTH: 13
<212> TYPE: PRT
<213> ORGANISM: Artificial sequence
<220> FEATURE:
<223> OTHER INFORMATION: Synthetic peptide
```

```
<400> SEQUENCE: 90

Cys Ala Ser Ser Leu Gly Thr Gly Asn Glu Gln Tyr Phe
1               5                   10

<210> SEQ ID NO 91
<211> LENGTH: 14
<212> TYPE: PRT
<213> ORGANISM: Artificial sequence
<220> FEATURE:
<223> OTHER INFORMATION: Synthetic peptide

<400> SEQUENCE: 91

Cys Ala Thr Ile Arg Lys Leu Thr Gly Asn Gln Phe Tyr Phe
1               5                   10

<210> SEQ ID NO 92
<211> LENGTH: 18
<212> TYPE: PRT
<213> ORGANISM: Artificial sequence
<220> FEATURE:
<223> OTHER INFORMATION: Synthetic peptide

<400> SEQUENCE: 92

Cys Ala Ser Ser Arg Trp Lys Gly Gln Gly Leu His Thr Gly Glu Leu
1               5                   10                  15

Phe Phe

<210> SEQ ID NO 93
<211> LENGTH: 14
<212> TYPE: PRT
<213> ORGANISM: Artificial sequence
<220> FEATURE:
<223> OTHER INFORMATION: Synthetic peptide

<400> SEQUENCE: 93

Cys Ala Met Arg Glu Gly Gln Ala Gly Thr Ala Leu Ile Phe
1               5                   10

<210> SEQ ID NO 94
<211> LENGTH: 14
<212> TYPE: PRT
<213> ORGANISM: Artificial sequence
<220> FEATURE:
<223> OTHER INFORMATION: Synthetic peptide

<400> SEQUENCE: 94

Cys Ala Ser Ser Leu Arg Gln Gly Arg Asp Thr Gln Tyr Phe
1               5                   10

<210> SEQ ID NO 95
<211> LENGTH: 14
<212> TYPE: PRT
<213> ORGANISM: Artificial sequence
<220> FEATURE:
<223> OTHER INFORMATION: Synthetic peptide

<400> SEQUENCE: 95

Cys Ala Ala Ser Ala Gly Asn Tyr Gly Gln Asn Phe Val Phe
1               5                   10

<210> SEQ ID NO 96
<211> LENGTH: 11
<212> TYPE: PRT
<213> ORGANISM: Artificial sequence
<220> FEATURE:
<223> OTHER INFORMATION: Synthetic peptide
```

```
<400> SEQUENCE: 96

Cys Ala Ser Ser Asp Arg Thr Ala Phe Phe
1               5                   10

<210> SEQ ID NO 97
<211> LENGTH: 11
<212> TYPE: PRT
<213> ORGANISM: Artificial sequence
<220> FEATURE:
<223> OTHER INFORMATION: Synthetic peptide

<400> SEQUENCE: 97

Cys Ala Val Asn Glu Pro Tyr Lys Leu Ser Phe
1               5                   10

<210> SEQ ID NO 98
<211> LENGTH: 12
<212> TYPE: PRT
<213> ORGANISM: Artificial sequence
<220> FEATURE:
<223> OTHER INFORMATION: Synthetic peptide

<400> SEQUENCE: 98

Cys Ala Ser Ser Phe Thr Lys Asn Glu Gln Tyr Phe
1               5                   10

<210> SEQ ID NO 99
<211> LENGTH: 11
<212> TYPE: PRT
<213> ORGANISM: Artificial sequence
<220> FEATURE:
<223> OTHER INFORMATION: Synthetic peptide

<400> SEQUENCE: 99

Cys Ala Met Arg Thr Gly Gly Lys Leu Ile Phe
1               5                   10

<210> SEQ ID NO 100
<211> LENGTH: 15
<212> TYPE: PRT
<213> ORGANISM: Artificial sequence
<220> FEATURE:
<223> OTHER INFORMATION: Synthetic peptide

<400> SEQUENCE: 100

Cys Ala Trp Ser Val Gly Gln Gly Val Arg Glu Thr Gln Tyr Phe
1               5                   10                  15

<210> SEQ ID NO 101
<211> LENGTH: 14
<212> TYPE: PRT
<213> ORGANISM: Artificial sequence
<220> FEATURE:
<223> OTHER INFORMATION: Synthetic peptide

<400> SEQUENCE: 101

Cys Ala Glu Asn Leu Ala Arg Gly Gly Asn Lys Leu Thr Phe
1               5                   10

<210> SEQ ID NO 102
<211> LENGTH: 14
<212> TYPE: PRT
<213> ORGANISM: Artificial sequence
<220> FEATURE:
<223> OTHER INFORMATION: Synthetic peptide
```

```
<400> SEQUENCE: 102

Cys Ala Thr Ser Arg Asp Leu Phe Gly Asp Glu Gln Phe Phe
1               5                   10

<210> SEQ ID NO 103
<211> LENGTH: 13
<212> TYPE: PRT
<213> ORGANISM: Artificial sequence
<220> FEATURE:
<223> OTHER INFORMATION: Synthetic peptide

<400> SEQUENCE: 103

Cys Ala Gly Cys Pro Phe Arg Asp Asp Lys Ile Ile Phe
1               5                   10

<210> SEQ ID NO 104
<211> LENGTH: 13
<212> TYPE: PRT
<213> ORGANISM: Artificial sequence
<220> FEATURE:
<223> OTHER INFORMATION: Synthetic peptide

<400> SEQUENCE: 104

Cys Ala Ser Ser Leu Ala Gly Glu Glu Thr Gln Tyr Phe
1               5                   10

<210> SEQ ID NO 105
<211> LENGTH: 12
<212> TYPE: PRT
<213> ORGANISM: Artificial sequence
<220> FEATURE:
<223> OTHER INFORMATION: Synthetic peptide

<400> SEQUENCE: 105

Cys Ala Leu Asn Asn Ala Gly Asn Met Leu Thr Phe
1               5                   10

<210> SEQ ID NO 106
<211> LENGTH: 15
<212> TYPE: PRT
<213> ORGANISM: Artificial sequence
<220> FEATURE:
<223> OTHER INFORMATION: Synthetic peptide

<400> SEQUENCE: 106

Cys Ala Ser Thr Leu Arg Gly Trp Ser Thr Gly Glu Leu Phe Phe
1               5                   10                  15

<210> SEQ ID NO 107
<211> LENGTH: 16
<212> TYPE: PRT
<213> ORGANISM: Artificial sequence
<220> FEATURE:
<223> OTHER INFORMATION: Synthetic peptide

<400> SEQUENCE: 107

Cys Ile Val Arg Ala Tyr Tyr Gly Gly Ala Thr Asn Lys Leu Ile Phe
1               5                   10                  15

<210> SEQ ID NO 108
<211> LENGTH: 15
<212> TYPE: PRT
<213> ORGANISM: Artificial sequence
<220> FEATURE:
<223> OTHER INFORMATION: Synthetic peptide
```

```
<400> SEQUENCE: 108

Cys Ala Ser Ser Gln Ala Arg Met Gly Asn Gly Glu Leu Phe Phe
1               5                   10                  15

<210> SEQ ID NO 109
<211> LENGTH: 14
<212> TYPE: PRT
<213> ORGANISM: Artificial sequence
<220> FEATURE:
<223> OTHER INFORMATION: Synthetic peptide

<400> SEQUENCE: 109

Cys Ala Glu Ser Gly Tyr Thr Gly Ala Asn Asn Leu Phe Phe
1               5                   10

<210> SEQ ID NO 110
<211> LENGTH: 15
<212> TYPE: PRT
<213> ORGANISM: Artificial sequence
<220> FEATURE:
<223> OTHER INFORMATION: Synthetic peptide

<400> SEQUENCE: 110

Cys Ala Ser Ser Ser Ala Arg Gln Gly Thr Asp Thr Gln Tyr Phe
1               5                   10                  15

<210> SEQ ID NO 111
<211> LENGTH: 13
<212> TYPE: PRT
<213> ORGANISM: Artificial sequence
<220> FEATURE:
<223> OTHER INFORMATION: Synthetic peptide

<400> SEQUENCE: 111

Cys Ala Thr Asp Phe Asn Ala Gly Asn Met Leu Thr Phe
1               5                   10

<210> SEQ ID NO 112
<211> LENGTH: 15
<212> TYPE: PRT
<213> ORGANISM: Artificial sequence
<220> FEATURE:
<223> OTHER INFORMATION: Synthetic peptide

<400> SEQUENCE: 112

Cys Ala Ser Ser Pro Asp Arg Glu Ile Thr Asp Thr Gln Tyr Phe
1               5                   10                  15

<210> SEQ ID NO 113
<211> LENGTH: 14
<212> TYPE: PRT
<213> ORGANISM: Artificial sequence
<220> FEATURE:
<223> OTHER INFORMATION: Synthetic peptide

<400> SEQUENCE: 113

Cys Ala Ala Ser Gly Arg Ala Gly Ala Asn Asn Leu Phe Phe
1               5                   10

<210> SEQ ID NO 114
<211> LENGTH: 15
<212> TYPE: PRT
<213> ORGANISM: Artificial sequence
<220> FEATURE:
<223> OTHER INFORMATION: Synthetic peptide
```

```
<400> SEQUENCE: 114

Cys Ser Ala Gly Val Ala Gly Gly Arg Pro Asp Thr Gln Tyr Phe
1               5                   10                  15

<210> SEQ ID NO 115
<211> LENGTH: 14
<212> TYPE: PRT
<213> ORGANISM: Artificial sequence
<220> FEATURE:
<223> OTHER INFORMATION: Synthetic peptide

<400> SEQUENCE: 115

Cys Ala Val Ser Glu Ser Asp Ser Gly Tyr Ala Leu Asn Phe
1               5                   10

<210> SEQ ID NO 116
<211> LENGTH: 15
<212> TYPE: PRT
<213> ORGANISM: Artificial sequence
<220> FEATURE:
<223> OTHER INFORMATION: Synthetic peptide

<400> SEQUENCE: 116

Cys Ala Ser Ser Leu Gly Ile Asp Ser Gly Tyr Gly Tyr Thr Phe
1               5                   10                  15

<210> SEQ ID NO 117
<211> LENGTH: 12
<212> TYPE: PRT
<213> ORGANISM: Artificial sequence
<220> FEATURE:
<223> OTHER INFORMATION: Synthetic peptide

<400> SEQUENCE: 117

Cys Ala Asp Val Ser Arg Asp Asp Lys Ile Ile Phe
1               5                   10

<210> SEQ ID NO 118
<211> LENGTH: 14
<212> TYPE: PRT
<213> ORGANISM: Artificial sequence
<220> FEATURE:
<223> OTHER INFORMATION: Synthetic peptide

<400> SEQUENCE: 118

Cys Ser Ala Leu Ala Gly Gly Asp Pro Tyr Glu Gln Tyr Phe
1               5                   10

<210> SEQ ID NO 119
<211> LENGTH: 12
<212> TYPE: PRT
<213> ORGANISM: Artificial sequence
<220> FEATURE:
<223> OTHER INFORMATION: Synthetic peptide

<400> SEQUENCE: 119

Cys Ala Met Arg Glu Gly Arg Ser Glu Val Ile Phe
1               5                   10

<210> SEQ ID NO 120
<211> LENGTH: 11
<212> TYPE: PRT
<213> ORGANISM: Artificial sequence
<220> FEATURE:
<223> OTHER INFORMATION: Synthetic peptide
```

```
<400> SEQUENCE: 120

Cys Ala Ser Ser Ser Tyr Asn Glu Gln Phe Phe
1               5                   10

<210> SEQ ID NO 121
<211> LENGTH: 12
<212> TYPE: PRT
<213> ORGANISM: Artificial sequence
<220> FEATURE:
<223> OTHER INFORMATION: Synthetic peptide

<400> SEQUENCE: 121

Cys Ala Glu Asn Gln Lys Gly Gly Lys Leu Ile Phe
1               5                   10

<210> SEQ ID NO 122
<211> LENGTH: 16
<212> TYPE: PRT
<213> ORGANISM: Artificial sequence
<220> FEATURE:
<223> OTHER INFORMATION: Synthetic peptide

<400> SEQUENCE: 122

Cys Ala Ser Ser Tyr Ser Arg Gly Thr Asn Thr Gly Glu Leu Phe Phe
1               5                   10                  15

<210> SEQ ID NO 123
<211> LENGTH: 11
<212> TYPE: PRT
<213> ORGANISM: Artificial sequence
<220> FEATURE:
<223> OTHER INFORMATION: Synthetic peptide

<400> SEQUENCE: 123

Cys Ala Gly Gln Asp Asn Asn Asp Met Arg Phe
1               5                   10

<210> SEQ ID NO 124
<211> LENGTH: 14
<212> TYPE: PRT
<213> ORGANISM: Artificial sequence
<220> FEATURE:
<223> OTHER INFORMATION: Synthetic peptide

<400> SEQUENCE: 124

Cys Ala Ser Thr Ala Trp Gly Ala Asn Thr Glu Ala Phe Phe
1               5                   10

<210> SEQ ID NO 125
<211> LENGTH: 12
<212> TYPE: PRT
<213> ORGANISM: Artificial sequence
<220> FEATURE:
<223> OTHER INFORMATION: Synthetic peptide

<400> SEQUENCE: 125

Cys Ala Val Asn Ala Asn Thr Asp Lys Leu Ile Phe
1               5                   10

<210> SEQ ID NO 126
<211> LENGTH: 14
<212> TYPE: PRT
<213> ORGANISM: Artificial sequence
<220> FEATURE:
<223> OTHER INFORMATION: Synthetic peptide
```

```
<400> SEQUENCE: 126

Cys Ser Ala Trp Glu Arg Thr Ser Leu Phe Glu Gln Tyr Phe
1               5                   10

<210> SEQ ID NO 127
<211> LENGTH: 14
<212> TYPE: PRT
<213> ORGANISM: Artificial sequence
<220> FEATURE:
<223> OTHER INFORMATION: Synthetic peptide

<400> SEQUENCE: 127

Cys Leu Val Gly Arg Asp Asn Ala Gly Asn Met Leu Thr Phe
1               5                   10

<210> SEQ ID NO 128
<211> LENGTH: 12
<212> TYPE: PRT
<213> ORGANISM: Artificial sequence
<220> FEATURE:
<223> OTHER INFORMATION: Synthetic peptide

<400> SEQUENCE: 128

Cys Ala Ser Gly Thr Asp Thr Asp Thr Gln Tyr Phe
1               5                   10

<210> SEQ ID NO 129
<211> LENGTH: 14
<212> TYPE: PRT
<213> ORGANISM: Artificial sequence
<220> FEATURE:
<223> OTHER INFORMATION: Synthetic peptide

<400> SEQUENCE: 129

Cys Ala Gly Asp Pro Asp Ser Gly Asn Thr Pro Leu Val Phe
1               5                   10

<210> SEQ ID NO 130
<211> LENGTH: 16
<212> TYPE: PRT
<213> ORGANISM: Artificial sequence
<220> FEATURE:
<223> OTHER INFORMATION: Synthetic peptide

<400> SEQUENCE: 130

Cys Ala Ser Ser Val Gly Leu Thr Val Thr Asn Thr Glu Ala Phe Phe
1               5                   10                  15

<210> SEQ ID NO 131
<211> LENGTH: 18
<212> TYPE: PRT
<213> ORGANISM: Artificial sequence
<220> FEATURE:
<223> OTHER INFORMATION: Synthetic peptide

<400> SEQUENCE: 131

Cys Ala Met Ser Ala Thr Glu Gly Arg Asp Asn Tyr Gly Gln Asn Phe
1               5                   10                  15

Val Phe

<210> SEQ ID NO 132
<211> LENGTH: 15
<212> TYPE: PRT
<213> ORGANISM: Artificial sequence
<220> FEATURE:
<223> OTHER INFORMATION: Synthetic peptide
```

-continued

```
<400> SEQUENCE: 132

Cys Ala Ser Gly Phe Tyr Thr Gly Val Ser Thr Glu Ala Phe Phe
1               5                   10                  15
```

ENGINEERING LYMPHOCYTES WITH SPECIFIC ALPHA AND BETA CHAINS ON THEIR T-CELL RECEPTOR

CROSS-REFERENCE TO RELATED APPLICATIONS

The present invention claims the priority benefit of U.S. Provisional Patent Application 62/569,215, filed Oct. 6, 2017, which is incorporated by reference in its entirety.

FIELD

Provided herein are methods to identify T-cell-receptor-recognizing cancer-specific antigens, and T-cell-receptor-engineered T cells having antigen-specific cytotoxic activity.

BACKGROUND

Cancer immunotherapies treat cancer by boosting the patient's own anti-tumor immune responses. In particular, the success of immune checkpoint inhibitors has highlighted the importance of anti-cancer immune activity in cancer patients. However, a minority of patients exhibit clinical benefits from anti-immune checkpoint treatments, and 70-80% of cancer patients have no or minimum benefit by this type of treatment. Therefore, it is important and urgent to identify mechanisms of resistance to immunotherapies and to develop methods to further enhance and improve immune responses (Ref 1; incorporated by reference in its entirety). Cytotoxic T lymphocytes (CTLs) play critical roles in cancer immunotherapy, but identification of T cell receptors (TCRs) of CTLs as well as their targets, cancer-specific antigens, is difficult and time-consuming.

SUMMARY

Provided herein are methods to identify TCR-recognizing cancer-specific antigens, and TCR-engineered T cells having antigen-specific cytotoxic activity.

In some embodiments, provided herein are methods comprising: (a) stimulating target lymphocytes (e.g., CD8$^+$ cytotoxic T lymphocytes) with a stimulation peptide comprising candidate antigen sequence; (b) capturing immune-active lymphocytes (e.g., CD8$^+$ cytotoxic T lymphocytes) with T-cell receptor (TCR) that binds to the candidate peptide, wherein said capturing comprises contacting the immune-active T lymphocytes with a capture reagent that displays major histocompatibility complex (MHC) bound to a capture peptide comprising the candidate antigen sequence; and (c) sequencing the all or a portion of the TCR of the captured immune-active T lymphocytes.

In some embodiments, the target lymphocytes are obtained from a healthy donor. In some embodiments, the target lymphocytes are CD8$^+$ cytotoxic T lymphocytes. In some embodiments, the stimulating is performed in vitro (e.g., in cell culture).

In some embodiments, the peptide comprising a candidate antigen sequence is all or a fragment of an oncoantigen and neoantigen. In some embodiments, a candidate antigen sequence is all or a fragment of an oncoantigen and neoantigen.

In some embodiments, the capture reagent is an MHC multimer. In some embodiments, the MHC multimer is an MHC dextramer.

In some embodiments, the sequencing comprises a next-generation sequencing technique. In some embodiments, the portion of the TCR sequenced comprises the TCR-α and/or TCR-β chains. In some embodiments, the portion of the TCR sequenced comprises one or more complementarity determining regions (CDRs) of the TCR-α and/or TCR-β chains. In some embodiments, the portion of the TCR sequenced comprises the CDR3 of the TCR-α and/or TCR-β chains.

In some embodiments, the target lymphocytes (e.g., CD8$^+$ cytotoxic T lymphocytes) are a population of target lymphocytes, wherein the stimulation peptide is one of a population of stimulation peptides comprising different candidate antigen sequences; and wherein said capturing comprises contacting the population of immune-active T lymphocytes (e.g., CD8$^+$ cytotoxic T lymphocytes) with a capture reagents that displays major histocompatibility complex (MHC) bound to a population of capture peptides comprising the candidate antigen sequences.

In some embodiments, provided herein are TCR-recognizing cancer-specific antigens identified by the methods described herein (e.g., SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, etc.).

In some embodiments, provided herein are methods comprising: (a) stimulating target lymphocytes (e.g., CD8$^+$ cytotoxic T lymphocytes) with a stimulation peptide comprising candidate antigen sequence; (b) capturing immune-active T lymphocytes (e.g., CD8$^+$ cytotoxic T lymphocytes) with T-cell receptor (TCR) that binds to the candidate peptide, wherein said capturing comprises contacting the immune-active T lymphocytes with a capture reagent that displays major histocompatibility complex (MHC) bound to a capture peptide comprising the candidate antigen sequence; (c) sequencing the all or a portion of the TCR of the captured immune-active T lymphocytes; and further comprising: (d) generating engineered T lymphocytes (e.g., CD8$^+$ cytotoxic T lymphocytes) displaying all or a portion of the TCR of the captured immune-active T lymphocytes, wherein the engineered T lymphocytes recognize antigen presenting cells displaying MHC bound to the peptide comprising the candidate antigen sequence.

In some embodiments, the engineered T lymphocytes are CD8$^+$ cytotoxic T lymphocytes.

In some embodiments, generating engineered T lymphocytes (e.g., CD8$^+$ cytotoxic T lymphocytes) displaying all or a portion of the TCR of the captured immune-active T lymphocytes comprising: (i) cloning a nucleic acid sequence encoding the portion of the TCR of the captured immune-active T lymphocytes into a vector; (ii) introducing the vector into host T lymphocytes (e.g., CD8$^+$ cytotoxic T lymphocytes); and (iii) culturing under conditions such that the portion of the TCR of the captured immune-active T lymphocytes is expressed and displayed on the engineered T lymphocytes. In some embodiments, the portion of the TCR comprises the TCR-α and/or TCR-β chains. In some embodiments, the portion of the TCR comprises one or more complementarity determining regions (CDRs) of the TCR-α and/or TCR-β chains. In some embodiments, the portion of the TCR sequenced comprises the CDR3 of the TCR-α and/or TCR-β chains. In some embodiments, the portion of the TCR sequenced comprises an amino acid sequence selected from the group consisting of SEQ ID NOS: 45-132. In some embodiments, the engineered T lymphocytes display a TCR comprising α and β chains (e.g., CDR3s) comprising the amino acid sequence pairs selected from the group consisting of SEQ ID NOS: 45 and 46, 47 and 48, 49 and 50, 51 and 52, 53 and 54, 55 and 56, 57 and 58, 59 and 60, 61 and 62, 63 and 64, 65 and 66, 67 and 68, 69 and 70, 71 and 72, 73 and 74, 75 and 76, 77 and 78, 79 and 80, 81 and 82, 83 and 84, 85 and 86, 87 and 88, 89 and 90, 91 and 92, 93 and 94, 95 and 96, 97 and 98, 99 and 100, 101 and 102, 103 and 104, 105 and 106, 107 and 108, 109 and 110, 111 and 112, 113 and 114, 115 and 116, 117 and 118, 119 and 120, 121 and 122, 123 and 124, 125 and 126, 127 and 128, 129 and 130, and 131 and 132. In some embodiments, the vector is introduced into host T lymphocytes from a healthy donor host. In some embodiments, the vector is introduced into host T lymphocytes from a cancer patient to be treated with the engineered T lymphocytes.

In some embodiments, provided herein are engineered T lymphocytes (e.g., CD8$^+$ cytotoxic T lymphocytes) produced by the methods described herein. In some embodiments, the engineered T lymphocytes are CD8$^+$ cytotoxic T lymphocytes.

In some embodiments, provided herein are methods of treating cancer in a subject comprising administering the engineered T lymphocytes described herein (e.g., CD8$^+$ cytotoxic T lymphocytes) to a subject.

In some embodiments, provided herein are methods comprising: (a) stimulating target lymphocytes (e.g., CD8$^+$ cytotoxic T lymphocytes) with a stimulation peptide comprising candidate antigen sequence; (b) capturing immune-active T lymphocytes (e.g., CD8$^+$ cytotoxic T lymphocytes) with T-cell receptor (TCR) that binds to the candidate peptide, wherein said capturing comprises contacting the immune-active T lymphocytes with a capture reagent that displays major histocompatibility complex (MHC) bound to a capture peptide comprising the candidate antigen sequence; (c) sequencing the all or a portion of the TCR of the captured immune-active T lymphocytes; and further comprising: (d) generating therapeutic antibodies comprising all or a portion of the sequence of the TCR of the captured immune-active T lymphocytes. In some embodiments, the portion of the TCR comprises the TCR-α and/or TCR-β chains. In some embodiments, the portion of the TCR comprises one or more complementarity determining regions (CDRs) of the TCR-α and/or TCR-β chains. In some embodiments, the portion of the TCR sequenced comprises the CDR3 of the TCR-α and/or TCR-β chains. In some embodiments, the portion of the TCR sequenced comprises an amino acid sequence selected from the group consisting of SEQ ID NOS: 45-132. In some embodiments, the therapeutic antibodies comprise a CDR3s comprising the amino acid sequence pairs selected from the group consisting of SEQ ID NOS: 45 and 46, 47 and 48, 49 and 50, 51 and 52, 53 and 54, 55 and 56, 57 and 58, 59 and 60, 61 and 62, 63 and 64, 65 and 66, 67 and 68, 69 and 70, 71 and 72, 73 and 74, 75 and 76, 77 and 78, 79 and 80, 81 and 82, 83 and 84, 85 and 86, 87 and 88, 89 and 90, 91 and 92, 93 and 94, 95 and 96, 97 and 98, 99 and 100, 101 and 102, 103 and 104, 105 and 106, 107 and 108, 109 and 110, 111 and 112, 113 and 114, 115 and 116, 117 and 118, 119 and 120, 121 and 122, 123 and 124, 125 and 126, 127 and 128, 129 and 130, and 131 and 132. In some embodiments, the antibodies are antibody fragments.

In some embodiments, provided herein are antibodies produced by the methods described herein. In some embodiments, the antibodies are antibody fragments.

In some embodiments, provided herein are methods of treating cancer in a subject comprising administering the antibodies described herein to a subject.

Embodiments herein are described as utilizing CD8$^+$ cyttooxic lymphocytes as target cells and/or for generating engineered CD8$^+$ cytotoxic lymphocytes. However, in other embodiments within the scope herein, the target cells and/or engineered lymphocytes described herein may instead comprise CD4$^+$ helper lymphocytes, NK cells, NKT cells, B cells, dendritic cells as target cells.

BRIEF DESCRIPTION OF THE DRAWINGS

FIGS. 1A-C. Induction of FOXM1- and UBE2T-derived peptides-specific CTLs and cytotoxic activity of established CTLs. (A) IFN-γ production by FOXM1- and UBE2T-specific CTLs was confirmed only when exposed with C1R-A24 cells stimulated with FOXM1- or UBE2T-specific peptides. R/S ratio indicates responder cells (CTLs)/stimulators (C1R-A24 cells) ratio. (B, C) FOXM1- (B) and UBE2T-specific CTLs (C) exerted significant cell killing effect against HLA-A*24:02 positive SW480 cells, but not against HLA-A*24:02 negative HCC1143 cells or BT549 cells. Both CTLs ($2 \times 10^5$ cells/well) were coincubated with cancer cells ($2 \times 10^4$ cells/well) for 5 h.

FIG. 3A-H. Cytotoxic activity of TCR-engineered T cells for FOXM1 and UBE2T. (A, B) TCR-engineered T cells for FOXM1 (A) and UBE2T (B) exerted significant cell killing effect against HLA-A*24:02 positive SW480 cells, but not against HLA-A*24:02 negative HCC1143 cells. (C, D) The time course of cancer cells viability cocultured with FOXM1 (C) and UBE2T TCR-engineered T cells (D). Both sorted TCR-engineered T cells ($4 \times 10^5$ cells/well) were coincubated with cancer cells ($2 \times 10^4$ cells/well) for 20 h. (E, F) Recognition of TCR-engineered T cells for FOXM1 and UBE2T stimulated with C1R-A24 cells when pulsed with or without FOXM1- (E) or UBE2T-specific peptide (F) in ELISPOT assay. Sorted TCR-engineered T cells ($5 \times 10^4$ cells/well) were coincubated with peptide-pulsed stimulator cells ($2 \times 10^4$ cells/well) at 37° C. for 20 h in 96-well plates. (G, H) The secreted protein levels of granzyme B and perforin from original specific CTLs or TCR-engineered T cells after cocultured with cancer cells at 0 h, 2.5 h and 5 h.

DEFINITIONS

Figure 1A:
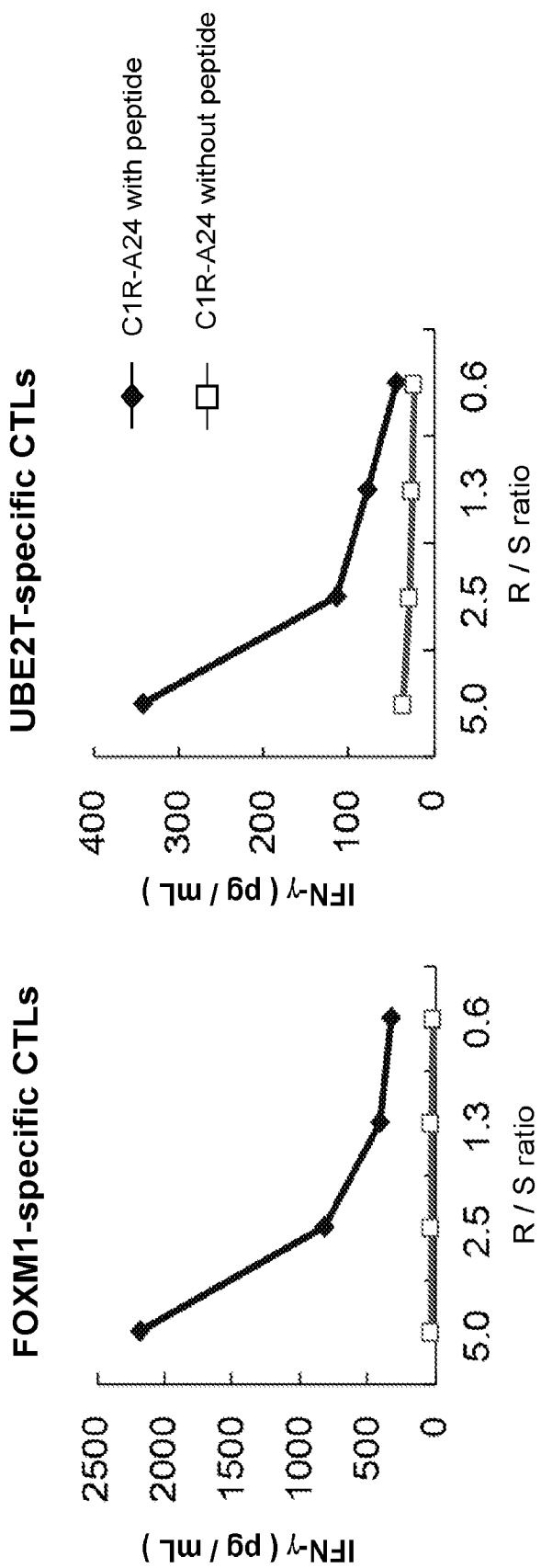

The terminology used herein is for the purpose of describing the particular embodiments only, and is not intended to limit the scope of the embodiments described herein. Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "an engineered lymphocyte" is a reference to one or more engineered lymphocytes and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, an "immune response" refers to the action of a cell of the immune system (e.g., T lymphocytes, B lymphocytes, natural killer (NK) cells, macrophages, eosinophils, mast cells, dendritic cells, neutrophils, etc.) and soluble macromolecules produced by any of these cells or the liver (including antibodies, cytokines, and complement) that results in selective targeting, binding to, damage to, destruction of, and/or elimination from a subject of invading pathogens, cells or tissues infected with pathogens, or cancerous or other abnormal cells. Some embodiments herein comprise generating an immune response in a subject to treat cancer.

As used herein, the term "immunotherapy" refers to the treatment or prevention of a disease or condition by a method comprising inducing, enhancing, suppressing or otherwise modifying an immune response. Some embodiments herein comprise immunotherapies.

As used herein, the terms "adoptive immunotherapy" and "adoptive cell transfer" refer to the transfer of immunocompetent cells (e.g., TCR-engineered T cells) for the treatment of cancer or infectious diseases (June, C. H., ed., 2001, In: Cancer Chemotherapy and Biotherapy: Principles and Practice, Lippincott Williams & Wilkins, Baltimore; Vonderheide et al., 2003, Immun. Research 27:1-15; incorporated by reference in its entirety). Some embodiments herein comprise adoptive immunotherapy.

As used herein, the term "cancer vaccine" refers to a composition (e.g., a tumor antigen) that elicits a specific immune response. The response is elicited from the subject's own immune system by administering the cancer vaccine.

As used herein, the term "native immune cell" refers to an immune cell that naturally occurs in the immune system of a subject. Illustrative examples include, but are not limited to, T-cells, NK cells, NKT cells, B cells, and dendritic cells. Some embodiments herein comprise eliciting a response in a subject to the subject native immune cells.

As used herein, the term "engineered immune cell" refers to an immune cell (e.g., T-cell, NK cell, NKT cell, B cell, dendritic cell, etc.) that is genetically modified. Some embodiments herein comprise generating and/or administering engineered immune cells.

As used herein, the term "T-cell receptor" ("TCR") refers to a molecular complex found on the surface of T cells (T lymphocytes) that is responsible for recognizing antigen fragments bound to major histocompatibility complex (MHC) of antigen presenting cells. The binding between TCR and antigen peptides is of relatively low affinity and is degenerate: that is, many TCRs recognize the same antigen peptide and many antigen peptides are recognized by the same TCR. The TCR is a heterodimer composed of two different protein chains. In 95% of human T cells, the TCR is made up of an alpha (α) chain and a beta (β) chain (encoded by TRA and TRB, respectively), whereas in 5% of T cells the TCR is made up of gamma and delta (γ/δ) chains (encoded by TRG and TRD, respectively). When the TCR engages with an antigenic peptide and the MHC, the T lymphocyte is activated through signal transduction. Some embodiments herein comprise generating engineered TCR, preparing cells displaying engineered TCR, and/or administering cells displaying engineered TCR to a subject for the treatment of cancer.

As used herein, the term "human leukocyte antigen" ("HLA") refers to the major histocompatibility complex (MHC) proteins in humans or the gene complex encoding the human MHC proteins.

As used herein, the term "antibody" refers to a whole antibody molecule or a fragment thereof (e.g., fragments such as Fab, Fab', and F(ab')$_2$), it may be a polyclonal or monoclonal antibody, a chimeric antibody, a humanized antibody, a human antibody, etc. As used herein, when an antibody or other entity "specifically recognizes" or "specifically binds" an antigen or epitope, it preferentially recognizes the antigen in a complex mixture of proteins and/or macromolecules, and binds the antigen or epitope with affinity which is substantially higher than to other entities not displaying the antigen or epitope. In this regard, "affinity which is substantially higher" means affinity that is high enough to enable detection of an antigen or epitope which is distinguished from entities using a desired assay or measurement apparatus. Typically, it means binding affinity having a binding constant ($K_a$) of at least $10^7$ M$^{-1}$ (e.g., >$10^7$ M$^{-1}$, >$10^8$ M$^{-1}$, >$10^9$ M$^{-1}$, >$10^{10}$ M$^{-1}$, >$10^{11}$ M$^{-1}$, >$10^{12}$ M$^{-1}$, >$10^{13}$ M$^{-1}$, etc.). In certain such embodiments, an antibody is capable of binding different antigens so long as the different antigens comprise that particular epitope. In certain instances, for example, homologous proteins from different species may comprise the same epitope. Some embodiments herein comprise generating and/or administering antibodies that bind oncoantigens and/or neoantigens.

As used herein, the term "antibody fragment" refers to a portion of a full-length antibody, including at least a portion antigen binding region or a variable region. Antibody fragments include, but are not limited to, Fab, Fab', F(ab')2, Fv, scFv, Fd, diabodies, and other antibody fragments that retain at least a portion of the variable region of an intact antibody. See, e.g., Hudson et al. (2003) Nat. Med. 9:129-134; herein incorporated by reference in its entirety. In certain embodiments, antibody fragments are produced by enzymatic or chemical cleavage of intact antibodies (e.g., papain digestion and pepsin digestion of antibody) produced by recombinant DNA techniques, or chemical polypeptide synthesis. For example, a "Fab" fragment comprises one light chain and the $C_{H1}$ and variable region of one heavy chain. The heavy chain of a Fab molecule cannot form a disulfide bond with another heavy chain molecule. A "Fab'" fragment comprises one light chain and one heavy chain that comprises additional constant region, extending between the $C_{H1}$ and $C_{H2}$ domains. An interchain disulfide bond can be formed between two heavy chains of a Fab' fragment to form a "F(ab')$_2$" molecule. An "Fv" fragment comprises the variable regions from both the heavy and light chains, but lacks the constant regions. A single-chain Fv (scFv) fragment comprises heavy and light chain variable regions connected by a flexible linker to form a single polypeptide chain with an antigen-binding region. Exemplary single chain antibodies are discussed in detail in WO 88/01649 and U.S. Pat. Nos. 4,946,778 and 5,260,203; herein incorporated by reference in their entireties. In certain instances, a single variable region (e.g., a heavy chain variable region or a light chain variable region) may have the ability to recognize and bind antigen. Other antibody fragments will be understood by skilled artisans. Some embodiments herein comprise generating and/or administering antibody fragments that bind oncoantigens and/or neoantigens.

As used herein, the term "monoclonal antibody" refers to an antibody which is a member of a substantially homogeneous population of antibodies that specifically bind to the same epitope. In certain embodiments, a monoclonal antibody is secreted by a hybridoma. In certain such embodiments, a hybridoma is produced according to certain methods known to those skilled in the art. See, e.g., Kohler and Milstein (1975) Nature 256: 495-499; herein incorporated by reference in its entirety. In certain embodiments, a monoclonal antibody is produced using recombinant DNA methods (see, e.g., U.S. Pat. No. 4,816,567). In certain embodiments, a monoclonal antibody refers to an antibody fragment isolated from a phage display library. See, e.g., Clackson et al. (1991) Nature 352: 624-628; and Marks et al. (1991) J. Mol. Biol. 222: 581-597; herein incorporated by reference in their entireties. The modifying word "monoclonal" indicates properties of antibodies obtained from a substantially-homogeneous population of antibodies, and does not limit a method of producing antibodies to a specific method. For various other monoclonal antibody production techniques, see, e.g., Harlow and Lane (1988) Antibodies: A Laboratory Manual (Cold Spring Harbor Laboratory, Cold Spring Harbor, N.Y.); herein incorporated by reference in its entirety. Some embodiments herein comprise generating and/or administering monoclonal antibodies that bind oncoantigens and/or neoantigens.

The term "antigen-binding site" refers to a portion of an antibody capable of specifically binding an antigen. In certain embodiments, an antigen-binding site is provided by one or more antibody variable regions.

The term "epitope" refers to any polypeptide determinant capable of specifically binding to an immunoglobulin or a T-cell or B-cell receptor. In certain embodiments, an epitope is a region of an antigen that is specifically bound by an antibody. In certain embodiments, an epitope may include chemically active surface groupings of molecules such as amino acids, sugar side chains, phosphoryl, or sulfonyl groups. In certain embodiments, an epitope may have specific three dimensional structural characteristics (e.g., a "conformational" epitope) and/or specific charge characteristics.

An epitope is defined as "the same" as another epitope if a particular antibody specifically binds to both epitopes. In certain embodiments, polypeptides having different primary amino acid sequences may comprise epitopes that are the same. In certain embodiments, epitopes that are the same may have different primary amino acid sequences. Different antibodies are said to bind to the same epitope if they compete for specific binding to that epitope.

As used herein, the term "sequence identity" refers to the degree to which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) have similar polymer sequences. For example, similar amino acids are those that share the same biophysical characteristics and can be grouped into the families (see above). The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position. In some embodiments, peptides or polypeptides herein comprise a minimum sequence identity to a base sequence.

The term "effective dose" or "effective amount" refers to an amount of an agent, e.g., an antibody, that results in the reduction of symptoms in a patient or results in a desired biological outcome. In certain embodiments, an effective dose or effective amount is sufficient to treat or reduce symptoms of a disease or condition.

As used herein, the terms "administration" and "administering" refer to the act of giving a drug, prodrug, or other agent, or therapeutic to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

The term "treatment" encompasses both therapeutic and prophylactic/preventative measures unless otherwise indicated. Those in need of treatment include, but are not limited to, individuals already having a particular condition as well as individuals who are at risk of acquiring a particular condition or disorder (e.g., those having a genetic or epigenetic predisposition; based on age, gender, lifestyle, etc.).

The term "treating" refers to administering an agent to a subject for therapeutic and/or prophylactic/preventative purposes.

A "therapeutic agent" refers to an agent that may be administered in vivo to bring about a therapeutic and/or prophylactic/preventative effect.

A "therapeutic antibody" refers to an antibody that may be administered in vivo to bring about a therapeutic and/or prophylactic/preventative effect.

As used herein, the terms "co-administration" and "co-administering" refer to the administration of at least two agent(s) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "pharmaceutical composition" refers to the combination of an active agent (e.g., binding agent) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintegrants (e.g., potato starch or sodium starch glycolate), and the like. The compositions also can include stabilizers and preservatives. For examples of carriers, stabilizers and adjuvants, see, e.g., Martin, Remington's Pharmaceutical Sciences, 15th Ed., Mack Publ. Co., Easton, Pa. (1975), incorporated herein by reference in its entirety.

As used herein, the term "healthy donor" refers to a mammal, such a human, who does not suffer from any form of cancer and/or whose cells/tissues that are used in embodiments herein do not show any signs of cancer (e.g., cancer morphology, cancer biomarkers, etc.).

DETAILED DESCRIPTION

Provided herein are methods to identify TCR-recognizing cancer-specific antigens, and TCR-engineered T cells having antigen-specific cytotoxic activity.

Pre-existing cytotoxic T lymphocytes (CTLs) recognizing cancer-specific antigens (oncoantigens and neoantigens) in tumor or blood circulation play critical roles to achieve a beneficial clinical response to cancer immunotherapy. For instance, a higher number of somatic mutations may increase a chance of generating a larger number of immunogenic neoantigens that could be recognized by lymphocytes with high cytolytic activity, which may be further unleashed by immune checkpoint inhibitors (Refs. 2-5; incorporated by reference in their entireties). In addition, higher expression levels of programmed death-ligand 1 (PD-L1), that interacts with programmed death-1 (PD-1) in T cells, in cancer cells was upregulated and is a biomarker for good clinical response (Refs. 4, 6-8; incorporated by reference in their entireties). Furthermore, tumor-infiltrating lymphocytes (TILs) in patients who responded to adoptive TILs transfer therapy include CTLs targeting both neoantigens and oncoantigens (shared antigens) (Ref 9; incorporated by reference in its entirety).

To enhance CTL-mediated anti-tumor immune responses for further improvement in clinical outcomes of cancer immunotherapy, embodiments herein utilize cancer-specific antigens, oncoantigens and neoantigens, as vaccines to activate antigen-specific CTLs in cancer patients. Oncoantigens are immunogenic peptides derived from oncogenic proteins that are highly expressed in cancer cells but not expressed in normal organs, except testis or fetal organs (Ref 10; incorporated by reference in its entirety). It has been contemplated that immunogenic peptide epitopes derived from oncoantigens induce oncoantigen-specific CTLs and improve the prognosis of cancer patients (Refs. 11-13; incorporated by reference in their entireties). Neoantigens are immunogenic peptides derived from non-synonymous mutations in cancer cells (Ref 10; incorporated by reference in its entirety). Considering some evidence that neoantigen-specific T cells showed good clinical outcome (Refs. 14-15; incorporated by reference in their entireties), neoantigen vaccine provides an option to further activate anti-cancer immune responses in patients. However, since induction of a sufficient number of anti-tumor T cells with vaccine therapy often occur very gradually and needs several months, this vaccine approach does not work for patients with a large tumor burden. Hence, identification of cancer antigen-specific T cell receptor (TCR), generation of TCR-engineered T cells using autologous T lymphocytes, and infusion of such genetically engineered T cells with/without anti-immune checkpoint antibodies provide attractive options for patients with advanced tumors where the host immune system was usually suppressed significantly. Preclinical studies and recent clinical trials have showed encouraging results that oncoantigen/neoantigen-specific TCR-engineered T cells are even effective for a large size of solid tumors (Refs. 16-18; incorporated by reference in their entireties). Provided herein are rapid screening methods to identify TCR sequences that recognize neoantigens and the rapid preparation of personalized TCR-engineered T cell therapies therewith.

Experiments were conducted during development of embodiments herein to establish a rapid screening method to detect oncoantigen/neoantigen-specific TCRs. After in vitro stimulation of CD8+ T lymphocytes from healthy donors with candidate peptides, CD8+ T cells were sorted using an HLA class I dextramer with each peptide, and TCR sequences for these cells were determined. Mono- or oligo-clonal expansion of unique T cells was achieved by stimulation of the epitope peptides. The TCR cDNAs were cloned and TCR-engineered T cells were generated. Through this approach, two antigen-specific CD8+ T cell clones were generated; two of the T-cell clones, which recognize oncoantigens derived from FOXM1 and UBE2T, revealed strong cytotoxic activity against HLA-matched cancer cells expressing target proteins, but not against HLA-unmatched cancer cells. The methods described herein allow for the rapid identification of TCR-recognizing cancer-specific antigens after obtaining antigen peptides. The approach allows for the rapid development of personalized T-cell immunotherapies for treating cancer. Provided herein is a pipeline to identify TCR-recognizing cancer-specific antigens by integrating the in vitro neoantigen stimulation of T cells, dextramer sorting, and TCR sequencing using next-generation sequencers as well as to establish TCR-engineered T cells having antigen-specific cytotoxic activity.

Experiments conducted during development of embodiments herein to develop a pipeline from screening of putative oncoantigen/neoantigen-derived peptides to induction of specific T cells from peripheral blood mononuclear cells (PBMCs) of healthy donors, and also established antigen-specific TCR-engineered T cells. Throughout this pipeline, immunogenic oncoantigens/neoantigens-derived peptides are identified as useful in cancer vaccines, and oncoantigen/neoantigen-specific TCRs are identified which lead to the establishment of antigen-specific TCR-engineered T cells to observe cytotoxic activity against HLA-matched cancer cells.

As a source of PBMCs, PBMCs from healthy donors allow detection of candidates for oncoantigens/neoantigens-specific CTLs, because they have different T cell repertoires from that of cancer patients. T cells obtained from healthy donors broaden neoantigen-specific T cell reactivity and enable targeting of neoantigens that have not been recognized by the patients' own immune system (Ref 30; incorporated by reference in its entirety). In some embodiments, after identification of TCR recognizing cancer-specific antigens, TCR-engineered T cells are established from autologous T cells from patients and infused as an adoptive cell transfer therapy.

TCR-engineered T cells, generated using the methods described herein, using PBMCs from HLA-A*24:02-positive healthy donors, recognized only HLA-A*24:02 restricted peptides and showed significant cytotoxic activity against the HLA-A*24:02 matched cancer cells. Considering that TCR-engineered T cells targeting HLA-A*02:01 restricted NY-ESO-1-derived peptide using autologous PBMCs showed encouraging clinical responses in myeloma patients (Ref 21; incorporated by reference in its entirety), it is noteworthy that the TCR-engineered T cells from healthy donors herein also exerted cytotoxic activity against HLA-A matched cancer cells. These results demonstrate the feasibility of preparing TCR-engineered T cells from healthy donors, for example, in situations in which obtaining autologous T cells from patients in unfeasible.

The pipeline described herein provides personalized immunotherapies responding to both oncoantigens and neoantigens. Given that some oncoantigens are frequently overexpressed in many types of cancer, TCR-engineered T cell therapy targeting oncoantigens is reasonable because identified TCRs recognizing specific oncoantigens have broad utility for patients having the same HLA genotype. For instance, elevated FOXM1 or UBE2T expression in tumor tissues was correlated with poor survival of patients with breast cancer, colon cancer, and prostate cancer (Refs. 31-34; incorporated by reference in its entirety). Therefore, in some embodiments, the FOXM1- and UBE2T-specific TCR engineered T cells describe herein find use in adoptive transfer therapies. Given that clinical benefit of chimeric antigen receptor (CAR) T cell therapy and TCR-engineered T cell therapy are currently limited to hematological malignancies (Refs. 35-36; incorporated by reference in their entireties), the pipeline presented herein for oncoantigen-specific TCR-engineered T cells provide another adoptive cell transfer therapy for solid tumors. In contrast, neoantigens are more specific to cancer cells and regarded as attractive immune targets, although their presentation is dependent on somatic mutations of cancer cell. Considering that the transfer therapy of neoantigen-specific TILs already showed encouraging clinical results against not only melanoma but solid tumors (Refs. 14-15; incorporated by reference in their entireties), the TCR-engineered T cells for neoantigens described herein provide a therapy in the clinical settings.

In some embodiments, provided herein are methods for identifying sequences of immune active TCR comprising stimulating target lymphocytes (e.g., CD8$^+$ cytotoxic T lymphocytes) with a stimulation peptide comprising candidate antigen sequence. In some embodiments, stimulation peptides are fragments of proteins that are expressed on cancer and/or tumor cells. In some embodiments, stimulation peptides are fragments of cancer-specific antigens and/or tumor-specific antigens. In some embodiments, the target T lymphocytes are obtained from any suitable source (e.g., a donor, cell culture, etc.). In some embodiments, the target T lymphocytes are obtained from a healthy donor. In some embodiments, the target T lymphocytes are CD8$^+$ cytotoxic T lymphocytes. In some embodiments, the stimulating is performed in vitro (e.g., in cell culture). In some embodiments, the type of cell culture is determined by the type of target T lymphocytes. Suitable conditions and methods for culturing T lymphocytes and stimulating T lymphocytes with a stimulation peptide are understood in the field.

In some embodiments, the target T lymphocytes (e.g., CD8$^+$ cytotoxic T lymphocytes) are a population of target T lymphocytes, and the stimulation peptide is one of a population of stimulation peptides comprising different candidate antigen sequences; and wherein said capturing comprises contacting the population of immune-active T lymphocytes (e.g., CD8$^+$ cytotoxic T lymphocytes) with a capture reagents that displays major histocompatibility complex (MHC) bound to a population of capture peptides comprising the candidate antigen sequences.

In some embodiments, the target lymphocytes are CD8$^+$ cytotoxic lymphocytes, CD4$^+$ helper lymphocytes, NK cells, NKT cells, B cells, dendritic cells, etc.

In some embodiments, the stimulation peptide comprising a candidate antigen sequence is all or a fragment of an oncoantigen and neoantigen. In some embodiments, a candidate antigen sequence is all or a fragment of an oncoantigen and neoantigen. In some embodiments, the stimulation peptide comprises a random amino acid sequence and methods herein allow for identification of peptides capable of eliciting an immune response. In some embodiments, the stimulation peptide comprises an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, and SEQ ID NO: 44.

In some embodiments, after stimulating the target T lymphocytes with a stimulation peptide, immune-active T lymphocytes (e.g., CD8$^+$ cytotoxic T lymphocytes) with T-cell receptor (TCR) that binds to the stimulation peptide are captured. In some embodiments, capturing comprises contacting the immune-active T lymphocytes with a capture reagent that displays major histocompatibility complex (MHC) bound to a capture peptide comprising the candidate antigen sequence. In some embodiments, the capture reagent displays a peptide comprising the sequence of one or more of the stimulation peptides. In some embodiments, the peptide is added to the T lymphocytes in a form bound to a MHC I complex. In some embodiments, the capture reagent is an MHC multimer. In some embodiments, the MHC multimer is an MHC dextramer. For example, the peptide may be presented to the T lymphocytes bound to MHC dextramers. In some embodiments, MHC dextramers are fluorescently-labeled MHC multimers bound to a dextrose backbone. The use of multimeric MHC structures has the advantage that multiple copies of the peptide are presented thereby increasing the capture potential.

In some embodiments, after capture of the immune-active T lymphocytes, all or a portion of the TCR of the captured immune-active T lymphocytes is sequenced. In some embodiments, the sequencing comprises a next-generation sequencing technique. Next-generation sequencing techniques are described in more detail below. In some embodiments, the portion of the TCR sequenced comprises the TCR-α and/or TCR-β chains. In some embodiments, the portion of the TCR sequenced comprises one or more complementarity determining regions (CDRs) of the TCR-α and/or TCR-β chains. In some embodiments, the portion of the TCR sequenced comprises the CDR3 of the TCR-α and/or TCR-β chains.

In some embodiments, provided herein are TCR-recognizing cancer-specific antigens identified by the methods described herein (e.g., SEQ ID NO: 1, SEQ ID NO: 2, etc.). In some embodiments, the cancer-specific antigens identified by the methods described herein are employed as therapeutics, such as cancer vaccines. Delivery systems for cancer vaccines may include, for example, liposomes, systems made of cholesterol, cholesterol hemisuccinate or alpha-tochoferol (e.g., vitamin E), or other amphipathic molecules in which modified or synthesized neoantigens can attach or insert. In some embodiments, a cancer vaccine comprises a cancer-specific antigen identified by the methods herein of variants thereof. In some embodiments, a cancer-specific antigen is provided as fusion peptide. In some embodiments, incorporates multiple sequences identified in the methods herein. In some embodiments, the peptide used in a cancer vaccine is 10-80 amino acids in length (e.g., 10, 20, 30, 40, 50, 60, 70, 80, or ranges therebetween).

In some embodiments, provided herein are therapeutic antibodies that binds to the TCR-recognizing cancer-specific antigens described herein. In some embodiments, a therapeutic antibody herein is an antibody fragment. Antibodies and antibody fragments for use in treatment of cancer are well understood in the field. In some embodiments, antibodies are monoclonal antibodies. In some embodiments, antibodies are humanized antibodies. In some embodiments, the therapeutic antibodies bind to an antigen comprising an amino acid sequence selected from the group consisting of SEQ ID NOS: 1-44. In some embodiments, the therapeutic antibodies comprise CDR3 sequences comprising pairs of amino acid sequences selected from the group consisting of SEQ ID NOS: 45 and 46, 47 and 48, 49 and 50, 51 and 52, 53 and 54, 55 and 56, 57 and 58, 59 and 60, 61 and 62, 63 and 64, 65 and 66, 67 and 68, 69 and 70, 71 and 72, 73 and 74, 75 and 76, 77 and 78, 79 and 80, 81 and 82, 83 and 84, 85 and 86, 87 and 88, 89 and 90, 91 and 92, 93 and 94, 95 and 96, 97 and 98, 99 and 100, 101 and 102, 103 and 104, 105 and 106, 107 and 108, 109 and 110, 111 and 112, 113 and 114, 115 and 116, 117 and 118, 119 and 120, 121 and 122, 123 and 124, 125 and 126, 127 and 128, 129 and 130, and 131 and 132.

In some embodiments, provided herein are methods for generating engineered T lymphocytes (e.g., CD8$^+$ cytotoxic T lymphocytes) displaying all or a portion of a TCR of captured immune-active T lymphocytes, wherein the engineered T lymphocytes recognize antigen presenting cells displaying MHC bound to the peptide comprising the candidate antigen sequence. In some embodiments, the engineered lymphocytes are CD8$^+$ cytotoxic lymphocytes, CD4$^+$ helper lymphocytes, NK cells, NKT cells, B cells, dendritic cells, etc. In some embodiments, sequences TCR of immune-active T lymphocytes are used to prepare nucleic acids and/or vectors encoding TCRs that will recognize target oncoantigens or neoantigens. In some embodiments, such nucleic acids and/or vectors are transformed, transfected, and/or otherwise placed into T lymphocytes to generate engineered T lymphocytes. Nucleic acids, vectors, and methods for such purposes are known in the field and described herein. In some embodiments, the engineered T lymphocytes are CD8$^+$ cytotoxic T lymphocytes. In some embodiments, generating engineered T lymphocytes (e.g., CD8$^+$ cytotoxic T lymphocytes) displaying all or a portion of the TCR of the captured immune-active T lymphocytes comprising: (i) cloning a nucleic acid sequence encoding the portion of the TCR of the captured immune-active T lymphocytes into a vector; (ii) introducing the vector into host T lymphocytes (e.g., CD8$^+$ cytotoxic T lymphocytes); and (iii) culturing under conditions such that the portion of the TCR of the captured immune-active T lymphocytes is expressed and displayed on the engineered T lymphocytes. In some embodiments, the portion of the TCR comprises the TCR-α and/or TCR-β chains. In some embodiments, the portion of the TCR comprises one or more complementarity determining regions (CDRs) of the TCR-α and/or TCR-β chains. In some embodiments, the portion of the TCR sequenced comprises the CDR3 of the TCR-α and/or TCR-β chains. In some embodiments, the portion of the TCR sequenced comprises an amino acid sequence selected from the group consisting of SEQ ID NOS: 45-132. In some embodiments, the engineered T lymphocytes display a TCR comprising α and β chains comprising the amino acid sequence pairs selected from the group consisting of SEQ ID NOS: 45 and 46, 47 and 48, 49 and 50, 51 and 52, 53 and 54, 55 and 56, 57 and 58, 59 and 60, 61 and 62, 63 and 64, 65 and 66, 67 and 68, 69 and 70, 71 and 72, 73 and 74, 75 and 76, 77 and 78, 79 and 80, 81 and 82, 83 and 84, 85 and 86, 87 and 88, 89 and 90, 91 and 92, 93 and 94, 95 and 96, 97 and 98, 99 and 100, 101 and 102, 103 and 104, 105 and 106, 107 and 108, 109 and 110, 111 and 112, 113 and 114, 115 and 116, 117 and 118, 119 and 120, 121 and 122, 123 and 124, 125 and 126, 127 and 128, 129 and 130, and 131 and 132. In some embodiments, the vector is introduced into host T lymphocytes from a healthy donor host. In some embodiments, the vector is introduced into host T lymphocytes from a cancer patient to be treated with the engineered T lymphocytes.

In some embodiments, provided herein are methods for generating engineered T lymphocytes (e.g., CD8$^+$ cytotoxic T lymphocytes) comprising chimeric antigen receptors (CARs), wherein the CARs recognize antigen presenting cells displaying MHC bound to the peptide comprising the candidate antigen sequence. In certain embodiments, the antigen-binding domain is a single-chain variable fragment (scFv) containing heavy and light chain variable regions that bind with specificity to the desired antigen (e.g., variable regions identified by the methods herein). In some embodiments, the CAR further comprises a transmembrane domain (e.g., a T cell transmembrane domain (e.g., a CD28 transmembrane domain)) and a signaling domain comprising one or more immunoreceptor tyrosine-based activation motifs (ITAMs)(e.g., a T cell receptor signaling domain (e.g., TCR zeta chain). In some embodiments, the CAR comprises one or more co-stimulatory domains (e.g., domains that provide a second signal to stimulate T cell activation). The invention is not limited by the type of co-stimulatory domain. In some embodiments, the engineered lymphocytes are $CD8^+$ cytotoxic lymphocytes, $CD4^+$ helper lymphocytes, NK cells, NKT cells, B cells, dendritic cells, etc. In some embodiments, TCR sequences of immune-active T lymphocytes are used to prepare CARs that will recognize target oncoantigens or neoantigens. In some embodiments, nucleic acids and/or vectors encoding such CARs are transformed or transfected into T cells, and/or the CARs are otherwise placed into T lymphocytes to generate engineered T lymphocytes. Nucleic acids, vectors, and methods for such purposes are known in the field and described herein. In some embodiments, the engineered T lymphocytes are $CD8^+$ cytotoxic T lymphocytes. In some embodiments, the CAR comprises an antigen binding region comprising sequences of the TCR-α and/or TCR-β chains identified in the methods herein. In some embodiments, the CAR comprises one or more complementarity determining regions (CDRs) of the TCR-α and/or TCR-β chains. In some embodiments, the portion of the TCR sequenced comprises the CDR3 of the TCR-α and/or TCR-β chains. In some embodiments, the portion of the TCR sequenced comprises an amino acid sequence selected from the group consisting of SEQ ID NOS: 45-132. In some embodiments, the engineered T lymphocytes display a TCR comprising α and β chains comprising the amino acid sequence pairs selected from the group consisting of SEQ ID NOS: 45 and 46, 47 and 48, 49 and 50, 51 and 52, 53 and 54, 55 and 56, 57 and 58, 59 and 60, 61 and 62, 63 and 64, 65 and 66, 67 and 68, 69 and 70, 71 and 72, 73 and 74, 75 and 76, 77 and 78, 79 and 80, 81 and 82, 83 and 84, 85 and 86, 87 and 88, 89 and 90, 91 and 92, 93 and 94, 95 and 96, 97 and 98, 99 and 100, 101 and 102, 103 and 104, 105 and 106, 107 and 108, 109 and 110, 111 and 112, 113 and 114, 115 and 116, 117 and 118, 119 and 120, 121 and 122, 123 and 124, 125 and 126, 127 and 128, 129 and 130, and 131 and 132. In some embodiments, the vector is introduced into host T lymphocytes from a healthy donor host. In some embodiments, the vector is introduced into host T lymphocytes from a cancer patient to be treated with the engineered T lymphocytes.

In some embodiments, the methods herein are applicable to generating engineered lymphocytes, such as $CD4^+$ helper lymphocytes, NK cells, NKT cells, B cells, dendritic cells, etc.

In some embodiments, nucleic acids (e.g., TCR cDNAs) are sequenced. Nucleic acid molecules may be sequence analyzed by any number of techniques. The analysis may identify the sequence of all or a part of a nucleic acid. Illustrative non-limiting examples of nucleic acid sequencing techniques include, but are not limited to, chain terminator (Sanger) sequencing and dye terminator sequencing, as well as "next generation" sequencing techniques. In some embodiments, RNA is reverse transcribed to cDNA before sequencing.

A number of DNA sequencing techniques are known in the art, including fluorescence-based sequencing methodologies (See, e.g., Birren et al., Genome Analysis: Analyzing DNA, 1, Cold Spring Harbor, N.Y.; herein incorporated by reference in its entirety). In some embodiments, automated sequencing techniques understood in that art are utilized. In some embodiments, the systems, devices, and methods employ parallel sequencing of partitioned amplicons (PCT Publication No: WO2006084132 to Kevin McKernan et al., herein incorporated by reference in its entirety). In some embodiments, DNA sequencing is achieved by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques include the Church polony technology (Mitra et al., 2003, Analytical Biochemistry 320, 55-65; Shendure et al., 2005 Science 309, 1728-1732; U.S. Pat. Nos. 6,432,360, 6,485,944, 6,511,803; herein incorporated by reference in their entireties) the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties), the Adessi PCR colony technology (Adessi et al. (2000). Nucleic Acid Res. 28, E87; WO 00018957; herein incorporated by reference in its entirety), and suitable combinations or alternative thereof.

A set of methods referred to as "next-generation sequencing" techniques have emerged as alternatives to Sanger and dye-terminator sequencing methods (Voelkerding et al., Clinical Chem., 55: 641-658, 2009; MacLean et al., Nature Rev. Microbiol., 7: 287-296; each herein incorporated by reference in their entirety). Next-generation sequencing (NGS) methods share the common feature of massively parallel, high-throughput strategies, with the goal of lower costs and higher speeds in comparison to older sequencing methods. NGS methods can be broadly divided into those that require template amplification and those that do not.

Sequencing techniques that finds use in embodiments herein include, for example, Helicos True Single Molecule Sequencing (tSMS) (Harris T. D. et al. (2008) Science 320:106-109). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm.sup.2. The flow cell is then loaded into a sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step. Further description of tSMS is shown for example in Lapidus et al. (U.S. Pat. No. 7,169,560), Lapidus et al. (U.S. patent application number 2009/0191565), Quake et al. (U.S. Pat. No. 6,818,395), Harris (U.S. Pat. No. 7,282,337), Quake et al. (U.S. patent application number 2002/0164629), and Braslaysky, et al., PNAS (USA), 100: 3960-3964 (2003), each of which is incorporated by reference in their entireties.

Another example of a DNA sequencing technique that finds use in embodiments herein is 454 sequencing (Roche) (Margulies, M et al. 2005, Nature, 437, 376-380; incorporated by reference in its entirety). 454 sequencing involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments are attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a DNA sequencing technique that finds use in embodiments herein is SOLiD technology (Applied Biosystems). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

Another example of a DNA sequencing technique that finds use in embodiments herein is Ion Torrent sequencing (U.S. patent application numbers 2009/0026082, 2009/ 0127589, 2010/0035252, 2010/0137143, 2010/0188073, 2010/0197507, 2010/0282617, 2010/0300559), 2010/ 0300895, 2010/0301398, and 2010/0304982; incorporated by reference in their entireties). In Ion Torrent sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to a surface and is attached at a resolution such that the fragments are individually resolvable. Addition of one or more nucleotides releases a proton ($H^+$), which signal detected and recorded in a sequencing instrument. The signal strength is proportional to the number of nucleotides incorporated.

Another example of a DNA sequencing technique that finds use in embodiments herein is Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated.

Another example of a DNA sequencing technique that finds use in embodiments herein is the single molecule, real-time (SMRT) technology of Pacific Biosciences. In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another example of a DNA sequencing technique that finds use in embodiments herein involves nanopore sequencing (Soni G V and Meller A. (2007) Clin Chem 53: 1996-2001; incorporated by reference in its entirety). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a DNA sequencing technique that finds use in embodiments herein involves using a chemical-sensitive field effect transistor (chemFET) array to sequence DNA (for example, as described in US Patent Application Publication No. 20090026082; incorporated by reference in its entirety). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

In some embodiments, other sequencing techniques (e.g., NGS techniques) understood in the field, or alternatives or combinations of the above techniques find use in embodiments herein.

Certain embodiments herein comprise the detection of one or more biomarkers (e.g., detection of cytokines (e.g., IFN-γ) to detect and/or quantify immune response). In some embodiments of the methods, the method further comprises isolating one or more biomarkers (e.g., detection of cytokines (e.g., IFN-γ) to detect and/or quantify immune response) from a biological sample or in vitro culture. In some embodiments, reagents are provided that bind to biomarkers. Such reagents are selected from antibodies, antibody fragments, aptamers, etc.

In some embodiments, the detection method includes an enzyme/substrate combination that generates a detectable signal that corresponds to the biomarker level (e.g., using the techniques of ELISA, Western blotting, isoelectric focusing). Generally, the enzyme catalyzes a chemical alteration of the chromogenic substrate which can be measured using various techniques, including spectrophotometry, fluorescence, and chemiluminescence. Suitable enzymes include, for example, luciferases, luciferin, malate dehydrogenase, urease, horseradish peroxidase (HRPO), alkaline phosphatase, beta-galactosidase, glucoamylase, lysozyme, glucose oxidase, galactose oxidase, and glucose-6-phosphate dehydrogenase, uricase, xanthine oxidase, lactoperoxidase, microperoxidase, and the like. In some embodiments, the detection method is a combination of fluorescence, chemiluminescence, radionuclide or enzyme/substrate combinations that generate a measurable signal. In some embodiments, multimodal signaling has unique and advantageous characteristics in biomarker assay formats.

In some embodiments, the biomarker presence/levels is detected using any analytical methods including, singleplex aptamer assays, multiplexed aptamer assays, singleplex or multiplexed immunoassays, expression profiling, mass spectrometric analysis, histological/cytological methods, etc. as discussed below.

In some embodiments, biomarkers (e.g., detection of cytokines (e.g., IFN-γ) to detect and/or quantify immune response) are detected/quantified using a suitable immunoassay. Immunoassay methods are based on the reaction of an antibody to its corresponding target or analyte and can detect the analyte in a sample depending on the specific assay format. To improve specificity and sensitivity of an assay method based on immuno-reactivity, monoclonal antibodies and fragments thereof are often used because of their specific epitope recognition. Polyclonal antibodies have also been successfully used in various immunoassays because of their increased affinity for the target as compared to monoclonal antibodies. Immunoassays have been designed for use with a wide range of biological sample matrices. Immunoassay formats have been designed to provide qualitative, semi-quantitative, and quantitative results.

Numerous immunoassay formats have been designed. ELISA or EIA can be quantitative for the detection of an analyte. This method relies on attachment of a label to either the analyte or the antibody and the label component includes, either directly or indirectly, an enzyme. ELISA tests may be formatted for direct, indirect, competitive, or sandwich detection of the analyte. Other methods rely on labels such as, for example, radioisotopes ($I^{125}$) or fluorescence. Additional techniques include, for example, agglutination, nephelometry, turbidimetry, Western blot, immunoprecipitation, immunocytochemistry, immunohistochemistry, flow cytometry, Luminex assay, and others (see ImmunoAssay: A Practical Guide, edited by Brian Law, published by Taylor & Francis, Ltd., 2005 edition; herein incorporated by reference in its entirety).

Exemplary assay formats include enzyme-linked immunosorbent assay (ELISA), radioimmunoassay, fluorescent, chemiluminescence, and fluorescence resonance energy transfer (FRET) or time resolved-FRET (TR-FRET) immunoassays. Examples of procedures for detecting biomarkers include biomarker immunoprecipitation followed by quantitative methods that allow size and peptide level discrimination, such as gel electrophoresis, capillary electrophoresis, planar electrochromatography, and the like.

Methods of detecting and/or for quantifying a detectable label or signal generating material depend on the nature of the label. The products of reactions catalyzed by appropriate enzymes (where the detectable label is an enzyme; see above) can be, without limitation, fluorescent, luminescent, or radioactive or they may absorb visible or ultraviolet light. Examples of detectors suitable for detecting such detectable labels include, without limitation, x-ray film, radioactivity counters, scintillation counters, spectrophotometers, colorimeters, fluorometers, luminometers, and densitometers.

Any of the methods for detection can be performed in any format that allows for any suitable preparation, processing, and analysis of the reactions. This can be, for example, in multi-well assay plates (e.g., 96 wells or 384 wells) or using any suitable array or microarray. Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting a detectable label.

In some embodiments, antigenic peptides and sequences thereof for use in embodiments herein are derived from cancer or tumor cell markers. Such markers may be selected from the group including but not limited to, epidermal growth factor receptor (EGFR, EGFR1, ErbB-1, HER1). ErbB-2 (HER2/neu), ErbB-3/HER3, ErbB-4/HER4, EGFR ligand family; insulin-like growth factor receptor (IGFR) family, IGF-binding proteins (IGFBPs), IGFR ligand family (IGF-1R); platelet derived growth factor receptor (PDGFR) family, PDGFR ligand family; fibroblast growth factor receptor (FGFR) family, FGFR ligand family, vascular endothelial growth factor receptor (VEGFR) family, VEGF family; HGF receptor family: TRK receptor family; ephrin (EPH) receptor family: AXL receptor family; leukocyte tyrosine kinase (LTK) receptor family; TIE receptor family, angiopoietin 1, 2; receptor tyrosine kinase-like orphan receptor (ROR) receptor family; discoidin domain receptor (DDR) family; RET receptor family; KLG receptor family; RYK receptor family; MuSK receptor family; Transforming growth factor alpha (TGF-α), TGF-α receptor; Transforming growth factor-beta (TGF-β), TGF-β receptor; Interleukin β receptor alpha2 chain (IL13Ralpha2), Interleukin-6 (IL-6), 1L-6 receptor, interleukin-4, IL-4 receptor, Cytokine receptors, Class I (hematopoietin family) and Class II (interferon/1L-10 family) receptors, tumor necrosis factor (TNF) family, TNF-α, tumor necrosis factor (TNF) receptor superfamily (TNTRSF), death receptor family, TRAIL-receptor; cancer-testis (CT) antigens, lineage-specific antigens, differentiation antigens, alpha-actinin-4, ARTC1, breakpoint cluster region-Abelson (Bcr-abl) fusion products, B-RAF, caspase-5 (CASP-5), caspase-8 (CASP-8), beta-catenin (CTNNB1), cell division cycle 27 (CDC27), cyclin-dependent kinase 4 (CDK4), CDKN2A, COA-1, dek-can fusion protein, EFTUD-2, Elongation factor 2 (ELF2), Ets variant gene 6/acute myeloid leukemia 1 gene ETS (ETC6-AML1) fusion protein, fibronectin (FN), GPNMB, low density lipid receptor/GDP-L fucose: beta-Dgalactose 2-alpha-Lfucosyltraosferase (LDLR/FUT) fusion protein, HLA-A2, MLA-A11, heat shock protein 70-2 mutated (HSP70-2M), KIAA0205, MART2, melanoma ubiquitous mutated 1, 2, 3 (MUM-1, 2, 3), prostatic acid phosphatase (PAP), neo-PAP, Myosin class 1, NFYC, OGT, OS-9, pml-RARalpha fusion protein, PRDXS, PTPRK, K-ras (KRAS2), N-ras (NRAS), HRAS, RBAF600, SIRT12, SNRPD1, SYT-SSX1 or -SSX2 fusion protein, Triosephosphate Isomerase, BAGE, BAGE-1, BAGE-2, 3, 4, 5, GAGE-1, 2, 3, 4, 5, 6, 7, 8, GnT-V (aberrant N-acetyl glucosaminyl transferase V, MGATS), HERV-K MEL, KK-LC, KM-HN-1, LAGE, LAGE-1, CTL-recognized antigen on melanoma (CAMEL), MAGE-A1 (MAGE-1). MAGE-A2, MAGE-A3, MAGE-A4, MAGE-AS, MAGE-A6, MAGE-A8, MAGE-A9, MAGE-A10. MAGE-A11, MAGE-A12, MAGE-3, MAGE-B1, MAGE-B2, MAGE-B5. MAGE-B6, MAGE-C1, MAGE-C2, mucin 1 (MUC1), MART-1/Melan-A (MLANA), gp100, gp100/Pme117 (S1LV), tyrosinase (TYR), TRP-1, HAGE, NA-88, NY-ESO-1, NY-ESO-1/LAGE-2, SAGE, Sp17. SSX-1, 2, 3, 4, TRP2-1NT2, carcino-embryonic antigen (CEA), Kallikrein 4, mamma-globin-A, OA1, prostate specific antigen (PSA), prostate specific membrane antigen, TRP-1/, 75. TRP-2 adipophilin, interferon inducible protein absent in melanoma 2 (AIM-2). BING-4, CPSF, cyclin D1, epithelial cell adhesion molecule (Ep-CAM), EpbA3, fibroblast growth factor-5 (FGF-5), glycoprotein 250 (gp250 intestinal carboxyl esterase (iCE), alpha-feto protein (AFP), M-CSF, mdm-2, MUCI, p53 (TP53), PBF, PRAME, PSMA, RAGE-1, RNF43, RU2AS, SOX10, STEAP1, survivin (BIRCS), human telomerase reverse transcriptase (hTERT), telomerase, Wilms' tumor gene (WT1), SYCP1, BRDT, SPANX, XAGE, ADAM2, PAGE-5, LIP1, CTAGE-1, CSAGE, MMA1, CAGE, BORIS, HOM-TES-85, AF15q14, HCA66I, LDHC, MORC, SGY-1, SPO11, TPX1, NY-SAR-35, FTHLI7, NXF2 TDRD1, TEX 15, FATE, TPTE, immunoglobulin idiotypes, Bence-Jones protein, estrogen receptors (ER), androgen receptors (AR), CD40, CD30, CD20, CD19, CD33, CD4, CD25, CD3, cancer antigen 72-4 (CA 72-4), cancer antigen 15-3 (CA 15-3), cancer antigen 27-29 (CA 27-29), cancer antigen 125 (CA 125), cancer antigen 19-9 (CA 19-9), beta-human chorionic gonadotropin, 1-2 microglobulin, squamous cell carcinoma antigen, neuron-specific enolase, heat shock protein gp96. GM2, sargramostim, CTLA-4, 707 alanine proline (707-AP), adenocarcinoma antigen recognized by T cells 4 (ART-4), carcinoembryogenic antigen peptide-1 (CAP-1), calcium-activated chloride channel-2 (CLCA2), cyclophilin B (Cyp-B), human signet ring tumor-2 (HST-2), etc. In some embodiments, antigenic peptides and sequences thereof for use in embodiments herein are derived from cell surface markers that are specific to, or predominantly displayed upon (e.g., recognizable by antibodies and/or immune cells) cancer/tumor cells.

In some embodiments, provided herein are T lymphocytes engineered to express immune-active TCR. In some embodiments, provided herein are T lymphocytes engineered to express immune-active CAR. Engineered cells may be generated by any suitable method in the art. In some embodiments, T lymphocytes are engineered to express/display immune-active TCR obtained by the methods described herein (e.g., stimulation, capture, sequencing). In some embodiments, T lymphocytes are engineered to express/display immune-active CAR obtained by the methods described herein (e.g., stimulation, capture, sequencing).

In some embodiments, provided herein are nucleic acids and nucleic acid sequences encoding immune-active TCR (or immune active CAR), as described above, and cells harboring such nucleic acids. In some embodiments, nucleic acid molecules are recombinant nucleic acid molecules. In some embodiments, nucleic acid molecules are synthetic. Nucleic acids encoding immune-active TCR and portions thereof may comprise DNA, RNA, PNA (peptide nucleic acid), and hybrids thereof.

In some embodiments, a nucleic acid encoding an immune-active TCR and portions thereof comprises one or more regulatory sequences. For example, promoters, transcriptional enhancers and/or sequences that allow for induced expression of the polynucleotide of the disclosure may be employed. In some embodiments, nucleic acid molecules are transcribed by an appropriate vector comprising a chimeric gene that allows for the transcription of the nucleic acid molecule in the cell.

In some embodiments, a nucleic acid molecule is a recombinantly-produced chimeric nucleic acid molecule comprising any of the aforementioned nucleic acid molecules either alone or in combination. In some embodiments, the nucleic acid molecule is part of a vector.

In some embodiments, provided herein are vectors comprising the nucleic acid molecule described herein (e.g., encoding immune-active TCR and portions thereof). Many suitable vectors are known to those skilled in molecular biology, the choice of which would depend on the function desired and include plasmids, cosmids, viruses, bacteriophages and other vectors used conventionally in genetic engineering. Methods that are well known to those skilled in the art can be used to construct various plasmids and vectors; see, for example, the techniques described in Sambrook et al. (1989) and Ausubel, Current Protocols in Molecular Biology, Green Publishing Associates and Wiley Interscience, N.Y. (1989), (1994); incorporated by reference in its entirety. Alternatively, the polynucleotides and vectors of the disclosure are reconstituted into liposomes for delivery to target cells. A cloning vector may be used to isolate individual sequences of DNA. Relevant sequences can be transferred into expression vectors where expression of a particular polypeptide is required. Typical cloning vectors include pBluescript SK, pGEM, pUC9, pBR322 and pGBT9. Typical expression vectors include pTRE, pCAL-n-EK, pESP-1, pOP13CAT.

In some embodiments, a vector comprises a nucleic acid sequence that is a regulatory sequence operably linked to the nucleic acid sequence encoding immune-active TCR and portions thereof. Such regulatory sequences (control elements) are known to the artisan and may include a promoter, a splice cassette, translation initiation codon, and insertion site for introducing an insert into the vector. In specific embodiments, the nucleic acid molecule is operatively linked to said expression control sequences allowing expression in eukaryotic or prokaryotic cells.

In some embodiments, the vector is a viral vector, such as a lentiviral vector or adenovirus associate vector.

In some embodiments, nucleic acids and/or vectors are used in a cell to express encoded polypeptides (e.g., immune-active TCR and portions thereof, etc.) in the cells. The nucleic acid molecules or vectors containing the DNA sequence(s) encoding any of the immune-active TCR described herein are introduced into the cells that in turn produce the polypeptide(s). The recited nucleic acid molecules and vectors may be designed for direct introduction or for introduction via liposomes, or viral vectors (e.g., adenoviral, retroviral) into a cell.

In accordance with the above, provided herein are methods to derive vectors, particularly plasmids, cosmids, viruses and bacteriophages used conventionally in genetic engineering that comprise a nucleic acid molecule encoding a polypeptide sequence (e.g., an immune-active TCR and portions thereof) described herein. In some embodiments, a vector is an expression vector and/or a gene transfer or targeting vector. Expression vectors derived from viruses such as retroviruses, vaccinia virus, adeno-associated virus, herpes viruses, or bovine papilloma virus, may be used for delivery of polynucleotides and/or vectors into targeted cell populations. Methods which are well known to those skilled in the art can be used to construct recombinant vectors. Vectors are transferred into the host cells by well-known methods, which vary depending on the type of cellular host.

In some embodiments, provided herein are cells comprising a host cell transformed or transfected with a vector defined herein above (e.g., encoding immune-active TCR described herein). The host cell may be produced by introducing at least one of the above described vectors or at least one of the above described nucleic acid molecules into the host cell. The presence of the at least one vector or at least one nucleic acid molecule in the host may mediate the expression of a gene encoding the above described immune-active TCRs and portions thereof. The nucleic acid molecule or vector that is introduced in the host cell may either integrate into the genome of the host or it may be maintained extrachromosomally.

In some embodiments, provided herein are methods comprising culturing a host cell defined herein above under conditions allowing the introduction of the nucleic acid and/or vector. In some embodiments, provided herein are methods comprising culturing a host cell defined herein above under conditions allowing expression of a construct (e.g., comprising an immune-active TCR or portion thereof). In particular embodiments, the cultured cells are provided to a subject (e.g., from which the original cells were obtained, a second subject, etc.). Conditions for the culturing of cells harboring an expression construct are known in the art.

In some embodiments, lymphocytes for engineering according to embodiments herein are from any suitable source. For example, a source of lymphocytes is a subject (e.g., the subject to be treated, a healthy subject, etc.). Lymphocytes can be obtained from a number of sources, including peripheral blood mononuclear cells, bone marrow, lymph node tissue, cord blood, thymus tissue, tissue from a site of infection, ascites, pleural effusion, spleen tissue, and tumors. In some embodiments, a specific type of lymphocyte (e.g., a cytotoxic T cell) desired for an embodiment described herein is obtained by appropriate methods. In some embodiments, lymphocytes expressing a particular marker are obtained by known methods (e.g., cell sorting). In some embodiments, cells are cultured following isolation. In some embodiments, cells are engineered using methods described herein.

In some embodiments, compositions herein (e.g., engineered lymphocytes, antibodies, vaccines, nucleic acid molecules, vectors, etc.) are administered either alone or in any combination using standard delivery systems and methods, and in at least some aspects, together with a pharmaceutically acceptable carrier or excipient. In the case of nucleic acid molecules or vectors, they may be stably integrated into the genome of the subject.

In some embodiments, methods and compositions are provided relating to the prevention, treatment or amelioration of a cancer comprising the step of administering to a subject in the need thereof an effective amount of compositions herein (e.g., engineered lymphocytes, antibodies, vaccines, nucleic acid molecules, vectors, etc.), as contemplated herein and/or produced by a process as contemplated herein. When cells are administered, the engineered cells are either administered to a site of treatment or may localize at a site of treatment (e.g., cell type, tissue type, etc.).

Non-limiting examples of cancers that may be treated with the compositions (e.g., engineered lymphocytes, antibodies, vaccines, etc.) and methods described herein include, but are not limited to: cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant;

carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant;

sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In some embodiments, the cancer is a melanoma (e.g., metastatic malignant melanoma), renal cancer (e.g. clear cell carcinoma), prostate cancer (e.g. hormone refractory prostate adenocarcinoma), pancreatic cancer (e.g., adenocarcinoma), breast cancer, colon cancer, gallbladder cancer, lung cancer (e.g. non-small cell lung cancer), esophageal cancer, squamous cell carcinoma of the head and neck, liver cancer, ovarian cancer, cervical cancer, thyroid cancer, glioblastoma, glioma, leukemia, lymphoma, and other neoplastic malignancies. In some embodiments, the cancer is a solid tumor cancer.

In some embodiments, the therapeutic compositions (e.g., engineered lymphocytes, antibodies, vaccines, etc.) and methods herein are employed with one or more co-therapies for the treatment of cancer. In some embodiments, one or more chemotherapies and/or immunotherapies are co-administered with the therapeutic compositions (e.g., engineered lymphocytes, antibodies, vaccines, etc.) and methods herein. In some embodiments, one or more chemotherapeutics and/or immunotherapies are provided as co-therapies, with or without (known) synergism.

The disclosure further encompasses co-administration protocols with other compounds, e.g., targeted toxins or other blocking or functional antibodies or compounds, which act via immune cells. The clinical regimen for co-administration may encompass co-administration at the same time, before or after the administration of the other component. Particular combination therapies include chemotherapy, radiation, surgery, hormone therapy, or other types of immunotherapy. Many chemotherapeutics are presently known in the art and can be used in combination with the compounds of the invention. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

In some embodiments, the therapeutic compositions (e.g., engineered lymphocytes, antibodies, vaccines, etc.) and methods herein are co-administered with one or more chemotherapeutics. Chemotherapies for co-administration herein include all classes of chemotherapeutic agents, such as, alkylating agents, antimetabalites, plant alkaloids, antibiotics, hormonal agents, and miscellaneous anticancer drugs. Specific agents include, for example, abraxane, altretamine, docetaxel, herceptin, methotrexate, novantrone, zoladex, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabine, fuldarabine, navelbine, farnesyl-protein tansferase inhibitors, transplatinum, 5-fluorouracil, vincristin, and vinblastin, or any analog or derivative variant of the foregoing and also combinations thereof. In some embodiments, chemotherapy is employed before, during and/or after administration of the therapeutic compositions (e.g., engineered lymphocytes, antibodies, vaccines, etc.) and methods herein.

In some embodiments, the therapeutic compositions (e.g., engineered lymphocytes, antibodies, vaccines, etc.) and methods herein are co-administered with radiotherapy, methods of which are understood in the field. In some embodiments, radiotherapy is employed before, during and/or after administration of the therapeutic compositions (e.g., engineered lymphocytes, antibodies, vaccines, etc.) and methods herein.

In some embodiments, the therapeutic compositions (e.g., engineered lymphocytes, antibodies, vaccines, etc.) and methods herein are co-administered with non-immune based targeted therapies, such as, agents that inhibit signaling pathways such WNT, p53, and/or RB-signaling pathways. Other examples include agents that inhibit tyrosine kinases, BRAF, STAT3, c-met, regulate gene expression, induce cell death or block blood vessel formation. Examples of specific agents include imatinib mesylate, dasatinib, nilotinib, bosutinib, lapatinib, gefinitib, erlotinib, tensirolimus, everolimus, vemurafenib, crizotinib, vorinostat, romidepsin, bexarotene, alitrionin, tretinoin, bortezomib, carfilzomib, pralatrexate, sorafenib, sunitinib, pazopanib, regorafenib, or cabozantinib. In some embodiments, non-immune based targeted therapy is employed before, during and/or after administration of engineered lymphocytes.

In some embodiments, the therapeutic compositions (e.g., engineered lymphocytes, antibodies, vaccines, etc.) and methods herein are co-administered with an immunotherapy. Immunotherapeutics generally rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect-cell killing. The antibody may also prevent cancer immunoevasion or immunosuppression. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. In some embodiments, immunotherapy is employed before, during and/or after administration of engineered lymphocytes.

In some embodiments, the therapeutic compositions (e.g., engineered lymphocytes, antibodies, vaccines, etc.) and methods herein are co-administered with a gene therapy in which a therapeutic polynucleotide is administered before, after, or at the same time as the engineered lymphocytes described herein. A variety of expression products are encompassed, including inducers of cellular proliferation, inhibitors of cellular proliferation, or regulators of programmed cell death.

In some embodiments, the therapeutic compositions (e.g., engineered lymphocytes, antibodies, vaccines, etc.) and methods herein are administered before, during, and/or after surgery. Surgeries include resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that embodiments herein may be used in conjunction with removal of superficial cancers, precancers, or incidental amounts of normal tissue.

In some embodiments, the therapeutic compositions (e.g., engineered lymphocytes, antibodies, vaccines, etc.) and methods herein are co-administered with other agents to improve the therapeutic efficacy of treatment.

In some embodiments, the co-administered agents are formulated into a single dose and/or composition. In some embodiments, the co-administered agents are in separate doses and/or compositions. In some embodiments in which separate doses and/or compositions are administered, the doses and/or compositions are administered simultaneously, consecutively, or spaced over a time span (e.g., <30 minutes, 1 hour, 2 hours, 4 hours, 6 hours, 12 hours, 1 day, 2 days, 3 days, 4 days, 5 days, 6 days, 1 week, or more, or any suitable ranges therebetween).

In some embodiments, the therapeutic compositions (e.g., engineered lymphocytes, antibodies, vaccines, etc.) and methods herein are provided as part of a kit or system along with one or more additional components, such as instructions, devices for administration, additional therapeutic agents, diagnostic agents, research agents, etc.

EXPERIMENTAL

Materials and Methods
Peptides 9-mer and 10-mer peptides were synthesized by using a standard solid phase synthesis method and purified by reversed phase high performance liquid chromatography (HPLC) (See Table 1a-e). The purity (>90%) and the identity of the peptides were determined by analytical HPLC and mass spectrometry analysis, respectively. Peptides were dissolved in dimethylsulfoxide at 20 mg/ml and stored at −80° C.

Table 1. Peptide Amino Acid Sequences for the Establishment of Peptide Specific CTLs.

TABLE 1a

List of HLA-A*24:02 restricted peptides used for establishing peptide specific CTLs

| Peptide Name | Amino Acid Sequence | SEQ ID NO |
|---|---|---|
| CDCA5-A24-10-232 | EWAAAMNAEF | 1 |
| CDH3-A24-10-807 | DYLNEWGSRF | 2 |
| FOXM1-A24-9-262 | IYTWIEDHF | 3 |
| HJURP-A24-9-408 | KWLISPVKI | 4 |
| INHBB-A24-9-180 | LYLKLLPYV | 5 |
| KIF20A-A24-10-66 | KVYLRVRPLL | 6 |
| MELK-A24-9-87_7N | EYCPGGNLF | 7 |
| NEIL3-A24-9-545 | EWADLSFPF | 8 |
| RNF43-A24-9-721 | NSQPVWLCL | 9 |
| SEMA5B-A24-10-290 | AYDIGLFAYF | 10 |
| SMYD3-A24-9-197 | QYCFECDCF | 11 |
| TOPK-A24-10-289 | SYQKVIELFS | 12 |
| UBE2T-A24-9-60 | RYPFEPPQI | 13 |
| VANGL1-A24-9-443 | RYLSAGPTL | 14 |
| VEGFR1-A24-9-1084 | SYGVLLWEI | 15 |
| VEGFR2-A24-9-169 | RFVPDGNRI | 16 |
| WDHD1-A24-9-844 | GYSNTATEW | 17 |
| WDRPUH-A24-9-314 | IYRVSFTDF | 18 |

TABLE 1b

List of HLA-A*02:01 restricted peptides used for establishing peptide specific CTLs

| Peptide Name | Amino Acid Sequence | SEQ ID NO |
|---|---|---|
| C12orf48-A02-10-193 | SIAGGQILSV | 19 |
| C18orf54-A02-9-507 | SLQKALHHL | 20 |
| C6orf167-A02-10-622 | TLLSIYIDGV | 21 |
| CDCA5-A02-9-183 | VVCSKLTEV | 22 |
| DEPDC1v1-A02-10-302 | ILVVCGYITV | 23 |
| ECT2-A02-9-34 | LLIGSTSYV | 24 |
| KNTC2-A02-9-184 | ALVWLIDCI | 25 |
| MELK-A02-9-138 | LLFDEYHKL | 26 |
| MPHOSPH1-A02-10-282 | YIYDLFVPVS | 27 |
| MYBL2-A02-9-144 | RIICEAHKV | 28 |
| NEIL3-A02-9-416 | FQNSPPASV | 29 |
| SMYD3-A02-9-335 | RLAFDIMRV | 30 |

TABLE 1b-continued

List of HLA-A*02:01 restricted peptides used for establishing peptide specific CTLs

| Peptide Name | Amino Acid Sequence | SEQ ID NO |
|---|---|---|
| TMEM22-A02-10-195 | TTMWRATTTV | 31 |
| TOMM34-A02-9-30 | ALYGRALRV | 32 |
| TTK-A02-9-593 | ITDQYIYMV | 33 |
| TTLL4-A02-9-66 | GLGPGLLGV | 34 |
| VANGL1-A02-9-484 | KCLDFSLVV | 35 |

TABLE 1c

List of HLA-A*11:01 restricted peptides used for establishing peptide specific CTLs

| Peptide Name | Amino Acid Sequence | SEQ ID NO |
|---|---|---|
| CDCA1-A11-9-219 | KTKRLNELK | 36 |
| DEPDC1v1-A11-9-627 | MSQNVDMPK | 37 |
| KIF20A-A11-9-45 | VVSTSLEDK | 38 |
| MPHOSPH1-A11-10-1546 | STSFEISRNK | 39 |

TABLE 1d

List of HLA-A*33:03 restricted peptides used for establishing peptide specific CTLs

| Peptide Name | Amino Acid Sequence | SEQ ID NO |
|---|---|---|
| CDCA1-A33-9-43 | EVLHMIYMR | 40 |
| FOXM1-A33-9-308 | WTIHPSANR | 41 |
| MPHOSPH1-A33-9-608 | EFTQYWAQR | 42 |
| VEGFR2-A33-9-114 | IYVYVQDYR | 43 |

TABLE 1e

List of HLA-A*03:01 restricted peptide used for establishing peptide specific CTLs

| Peptide Name | Amino Acid Sequence | SEQ ID NO |
|---|---|---|
| KOC1-A03-10-120 | AVVNVTYSSK | 44 |

Cell Lines

TISI (HLA-A*24:02, B-lymphoblastoid cell line) was purchased from International Histocompatibility Working Group. T2 (HLA-A*02:01, B-lymphoblastoid cell line), EB-3 (HLA-A3/Aw32, B-lymphoblastoid cell line), Jiyoye (HLA-A32, B-lymphoblastoid cell line), SW480 (HLA-A*24:02, colorectal adenocarcinoma), HCC1143 (HLA-A*31:01, breast cancer), BT549 (HLA-A*02:01, breast cancer) and C1R (lacking HLA-A and HLA-B, B lymphoblast) were purchased from American Type Culture Collection (Rockville, Md.). All cells were cultured under the recommendations of their respective depositors.

Generation of C1R Cells Stably Expressing HLA Class I

In addition to TISI and T2, human leukocyte antigen (HLA)-transfected C1R cells were used as stimulator cells. The cDNA encoding an open reading frame of HLA class I (A*24:02, A*02:01, A*11:01, A*33:03 or A*03:01) was amplified by PCR and inserted into an expression vector. C1R cells were transfected with HLA class I expression vector and cultured in presence of G418 (Invitrogen, Carlsbad, Calif.) for 14 days. G418-resistant single cell and feeder cells were plated into 96 well cell culture plate (Corning, Inc., Corning, N.Y.) containing culture medium supplemented with G418 and further cultured for 30 days. The expression of transfected HLA class I on the C1R cells was confirmed by flow cytometry analysis.

In Vitro CTL Induction

Monocyte-derived dendritic cells (DCs) were used as antigen-presenting cells to induce cytotoxic T lymphocyte (CTL) which respond against peptide presented on HLA class I. DCs were generated in vitro (Ref. 37; incorporated by reference in its entirety). Peripheral blood mononuclear cells (PBMCs) were isolated from blood of healthy volunteer by Ficoll-Paque PLUS (GE Healthcare). Monocytes (adherent cells in PBMCs) were cultured to induce into DCs in the presence of 1000 IU/ml of granulocyte-macrophage colony-stimulating factor (R&D Systems, Minneapolis, Minn.) and 1000 IU/ml of interleukin (IL)-4 (R&D System) in AIM-V Medium (Invitrogen) containing 2% heat-inactivated human serum (AIM-V/2% HS medium). After seven days of culture, monocyte-derived DCs were pulsed with 20 micro g/ml of the synthesized peptide in the presence of 3 micro g/ml of beta-2-microglobulin for 3 hr at 37° C. in AIM-V Medium. These peptide-pulsed DCs were inactivated by X ray-irradiation (20 Gy) and mixed at a 1:20 ratio with autologous CD8+ T cells obtained from PBMCs by using CD8 Positive Isolation Kit (Thermo Fisher Scientific, Carlsbad, Calif.). These cultures were set up in 48 well cell culture plate (Corning). Each well contained $1.5 \times 10^4$ peptide-pulsed DCs, $3 \times 10^5$ CD8+ T cells and 10 ng/ml of IL-7 (R&D System) in 0.5 ml of AIM-V/2% HS medium. The day after next (day 2), IL-2 (Novartis) was added to the culture at final concentration of 20 IU/ml. On day 7 and day 14, CD8+ T cells were further stimulated with autologous peptide-pulsed DCs. DCs were prepared each time in the same way as described above. Peptide specific IFN-γ production of CD8+ T cells was tested by ELISPOT assay on day 21 (Refs. 38-39; incorporated by reference in their entireties).

Expansion Culture

After limiting dilution, CD8+ T cells were expanded using Rapid Expansion Method (Ref 40; incorporated by reference in its entirety). EB-3 and Jiyoye were treated with Mitomycin C and used as feeder cells. CD8+ T cells were cultured with feeder cells ($5 \times 10^6$ cells each) and 40 ng/ml of anti-CD3 antibody in 25 ml of AIM-V/5% HS medium. Next day (day 1), 3000 IU of IL-2 were added to the culture. The half volume of culture medium were exchanged with fresh AIM-V/5% HS medium containing 60 IU/ml of IL-2 on day 5, 8 and 11. Peptide specific IFN-γ production of CD8+ T cells was tested by ELISA between day 14 and day 16 (Refs. 38-39; incorporated by reference in their entireties).

Detection of Peptide Specific IFN-γ

To examine peptide specific IFN-gamma production of CD8+ T cells, ELISPOT assay or ELISA were performed. Peptide-pulsed T2, TISI or HLA class I expressing C1R cells ($1 \times 10^4$ cells) were prepared as stimulator cells. CD8+ T cells were used as responder cells. IFN-gamma ELISPOT assay and IFN-gamma ELISA were performed under the manufacturer's procedure (BD Biosciences, San Jose, Calif.).

Evaluation of Cytotoxic Activities of CTLs Against Cancer Cells by Time-Lapse Recording CTLs and TCR-engineered T cells were pre-treated with IL-2 (100 U/mL) for 16 h. Target cells were pre-treated with IFN-γ (100 U/mL) for 48 h before experiments. The cells were incubated with 1 ug/mL of Calcein AM (Dojindo, Kumamoto, Japan) for 30 min. After 3-time washing by PBS, 2×10⁴ of target cells were mixed with 2×10⁵ FOXM1/UBE2T-specific CTLs or 4×10⁵ TCR-engineered T cells into Lab-Tek Chamber Slide Cover Glass Slide Sterile 16 Well (Thermo Scientific). Time-lapse recording was performed by an inverted microscope Axio Vert.A1 TL (Zeiss, Oberkochen, Germany). The live and dead cells were quantified using ImageJ program (National Institutes of Health, Bethesda, Md.).

T Cell Receptor Sequencing

TCR sequences were determined (Ref 41; incorporated by reference in its entirety). Total RNA was extracted from expanded or dextramer-positive T cells. cDNAs with common 5'-RACE adapter were synthesized using SMART library construction kit (Clontech, Mountain View, Calif.). The fusion PCR was performed to amplify TCRA or TCRB cDNAs using a forward primer corresponding to the SMART adapter sequence and reverse primers corresponding to the constant region of each of TCRA or TCRB. After adding the Illumina index sequences with barcode using the Nextera Index kit (Illumina, San Diego, Calif.), the prepared libraries were sequenced by 300-bp paired-end reads on the MiSeq (Illumina). Obtained sequence reads were analyzed using Tcrip software (Ref 41; incorporated by reference in its entirety). The sequence was also confirmed by Sanger sequence using fusion PCR products as a template (Thermo Scientific).

TCR-Engineered T Cells

Both TCRA and TCRB sequences were codon-optimized and cloned into pMP71-PRE (Refs. 18, 42; incorporated by reference in their entireties). To maximize TCR expression, modified murine TCRA and TCRB constant domains were used. Transient retrovival supernatants were generated and PBMCs from donors were transduced (Ref 18; incorporated by reference in its entirety). The expression of the TCR was evaluated with anti-human TCRβV antibodies. Only transduced TCR-engineered T cells were transduced using the staining with APC-conjugated anti-mouse TCR beta monoclonal antibody (H57-597, eBioscience, San Diego, Calif.) at a proper condition for TCR-engineered T cells for FOXM1 and UBE2T followed by the incubation with anti-APC microbeads (Miltenyi Biotec, Bergisch Gladbach, Germany) according to the manufacturer's instructions. To increase the number of T cells transduced with desired TCRs which were not occupied with antibodies, conditions were based on the peak fluorescence intensity and the number of sorted cells by comparing the five different conditions of antibody dilution. It was determined that 1:2000 (0.1 ug/mL) and 1:4000 (0.05 ug/mL) ratios of antibody staining were proper for sorting of TCR-engineered T cells for FOXM1 and UBE2T, respectively.

Results

Peptides-Specific CTLs

CTL clones were induced that are specific to HLA-A*24:02, HLA-A*02:01, HLA-A*11:01, HLA-A*33:03, or HLA-A*03:01 restricted peptides from Tables 1a-e. The CTLs were captured with HLA dextramer with each peptide, and TCR sequences for these cells were determined (See Tables 2a-e for CDR3 amino acid sequences of TCRs in the peptide specific CTLs). Using the HLA expressing cells with or without peptide, all of 44 CTL clones were evaluated for peptide specific IFN-γ production by ELISA assays.

Table 2. CDR3 Amino Acid Sequences of TCRs in the Peptide Specific CTLs.

TABLE 2a

List of predominant CDR3 sequences of CTL clones specific to the HLA-A*24:02 restricted peptides

| Peptide Name | TCR | Amino Acid Sequence | SEQ ID NO |
|---|---|---|---|
| CDCA5-A24-10-232 | alpha | CAALDSNYQLIW | 45 |
| | beta | CASSKNGGSYKNEQFF | 46 |
| CDH3-A24-10-807 | alpha | CAMREVLSGGGADGLTF | 47 |
| | beta | CASSPLIDTNQPQHF | 48 |
| FOXM1-A24-9-262 | alpha | CACPIMWGSNYKLTF | 49 |
| | beta | CASSLRVHEQYF | 50 |
| HJURP-A24-9-408 | alpha | CAMREALSYNTDKLIF | 51 |
| | beta | CASREYKNEQFF | 52 |
| INHBB-A24-9-180 | alpha | CAPSGSGAGSYQLTF | 53 |
| | beta | CASSFSIDTQYF | 54 |
| KIF20A-A24-10-66 | alpha | CAVIGGGSNYQLIW | 55 |
| | beta | CASSPSPLDWETQYF | 56 |
| MELK-A24-9-87_7N | alpha | CAGRNSGTYKYIF | 57 |
| | beta | CASSLGTPKETQYF | 58 |
| NEIL3-A24-9-545 | alpha | CAARGYSGAGSYQLTF | 59 |
| | beta | CASRQGGTPLHF | 60 |
| RNF43-A24-9-721 | alpha | CAVRRGNQFYF | 61 |
| | beta | CASSLALQGMVSTEAFF | 62 |
| SEMA5B-A24-10-290 | alpha | CAVDMWSQGNLIF | 63 |
| | beta | CASSLGTGDYEQYF | 64 |
| SMYD3-A24-9-197 | alpha | CAVRDIEAGGSYIPTF | 65 |
| | beta | CASSVGWTSSYEQYF | 66 |
| TOPK-A24-10-289 | alpha | CAVEAGYSTLTF | 67 |
| | beta | CASGAFF | 68 |
| UBE2T-A24-9-60 | alpha | CAMREGRNFNKFYF | 69 |
| | beta | CASSLSGGPNEQFF | 70 |
| VANGL1-A24-9-443 | alpha | CAMREVTGNQFYF | 71 |
| | beta | CASSQKSGPLKRQPQHF | 72 |
| VEGFR1-A24-9-1084 | alpha | CAVRAGAGNMLTF | 73 |
| | beta | CASSIDGLAGEQYF | 74 |
| VEGFR2-A24-9-169 | alpha | CAMSQYGNKLVF | 75 |
| | beta | CASSEIRNAYEQYF | 76 |
| WDHD1-A24-9-844 | alpha | CAVRGGSNYQLIW | 77 |
| | beta | CASSSSSGTPWNEQFF | 78 |
| WDRPUH-A24-9-314 | alpha | CATVNDYKLSF | 79 |
| | beta | CASSLVLGRNTEAFF | 80 |

TABLE 2b

List of predominant CDR3 sequences of CTL clones specific to the HLA-A*02:01 restricted peptides

| Peptide Name | TCR | Amino Acid Sequence | SEQ ID NO |
|---|---|---|---|
| C12orf48-A02-10-193 | alpha | CLVGDRQAGTALIF | 81 |
| | beta | CSVEGSLGGRDEQFF | 82 |

TABLE 2b-continued

List of predominant CDR3 sequences of CTL clones
specific to the HLA-A*02:01 restricted peptides

| Peptide Name | TCR | Amino Acid Sequence | SEQ ID NO |
|---|---|---|---|
| C18orf54-A02-9-507 | alpha | CAMRERSGGSYIPTF | 83 |
|  | beta | CASKGTGQKETQYF | 84 |
| C6orf167-A02-10-622 | alpha | CAETDTTSGTYKYIF | 85 |
|  | beta | CASSLFAQSSYKNEQFF | 86 |
| CDCA5-A02-9-183 | alpha | CAASAEGAGGTSYGKLTF | 87 |
|  | beta | CASSLLKNTEAFF | 88 |
| DEPDC1v1-A02-10-302 | alpha | CAVHDNYGQNFVF | 89 |
|  | beta | CASSLGTGNEQYF | 90 |
| ECT2-A02-9-34 | alpha | CATIRKLTGNQFYF | 91 |
|  | beta | CASSRWKGQGLHTGELFF | 92 |
| KNTC2-A02-9-184 | alpha | CAMREGQAGTALIF | 93 |
|  | beta | CASSLRQGRDTQYF | 94 |
| MELK-A02-9-138 | alpha | CAASAGNYGQNFVF | 95 |
|  | beta | CAS S SDRTAFF | 96 |
| MPHOSPH1-A02-10-282 | alpha | CAVNEPYKLSF | 97 |
|  | beta | CASSFTKNEQYF | 98 |
| MYBL2-A02-9-144 | alpha | CAMRTGGKLIF | 99 |
|  | beta | CAWSVGQGVRETQYF | 100 |
| NEIL3-A02-9-416 | alpha | CAENLARGGNKLTF | 101 |
|  | beta | CATSRDLFGDEQFF | 102 |
| SMYD3-A02-9-335 | alpha | CAGCPFRDDKIIF | 103 |
|  | beta | CASSLAGEETQYF | 104 |
| TMEM22-A02-10-195 | alpha | CALNNAGNMLTF | 105 |
|  | beta | CASTLRGWSTGELFF | 106 |
| TOMM34-A02-9-30 | alpha | CIVRAYYGGATNKLIF | 107 |
|  | beta | CASSQARMGNGELFF | 108 |
| TTK-A02-9-593 | alpha | CAESGYTGANNLFF | 109 |
|  | beta | CASSSARQGTDTQYF | 110 |
| TTLL4-A02-9-66 | alpha | CATDFNAGNMLTF | 111 |
|  | beta | CASSPDREITDTQYF | 112 |
| VANGL1-A02-9-484 | alpha | CAASGRAGANNLFF | 113 |
|  | beta | CSAGVAGGRPDTQYF | 114 |

TABLE 2c

List of predominant CDR3 sequences of CTL clones
specific to the HLA-A*11:01 restricted peptides

| Peptide Name | TCR | Amino Acid Sequence | SEQ ID NO |
|---|---|---|---|
| CDCA1-A11-9-219 | alpha | CAVSESDSGYALNF | 115 |
|  | beta | CASSLGIDSGYGTF | 116 |
| DEPDC1v1-A11-9-627 | alpha | CADVSRDDKIIF | 117 |
|  | beta | CSALAGGDPYEQYF | 118 |
| KIF20A-A11-9-45 | alpha | CAMREGRSEVIF | 119 |
|  | beta | CASSSYNEQFF | 120 |
| MPHOSPH1-A11-10-1546 | alpha | CAENQKGGKLIF | 121 |
|  | beta | CASSYSRGTNTGELFF | 122 |

TABLE 2d

List of predominant CDR3 sequences of CTL clones
specific to the HLA-A*33:03 restricted peptides

| Peptide Name | TCR | Amino Acid Sequence | SEQ ID NO |
|---|---|---|---|
| CDCA1-A33-9-43 | alpha | CAGQDNNDMRF | 123 |
|  | beta | CASTAWGANTEAFF | 124 |
| FOXM1-A33-9-308 | alpha | CAVNANTDKLIF | 125 |
|  | beta | CSAWERTSLFEQYF | 126 |
| MPHOSPH1-A33-9-608 | alpha | CLVGRDNAGNMLTF | 127 |
|  | beta | CASGTDTDTQYF | 128 |
| VEGFR2-A33-9-114 | alpha | CAGDPDSGNTPLVF | 129 |
|  | beta | CASSVGLTVTNTEAFF | 130 |

TABLE 2e

List of predominant CDR3 sequences of CTL clones
specific to the HLA-A*03:01 restricted peptides

| Peptide Name | TCR | Amino Acid Sequence | SEQ ID NO |
|---|---|---|---|
| KOC1-A03-10-120 | alpha | CAMSATEGRDNYGQNFVF | 131 |
|  | beta | CASGFYTGVSTEAFF | 132 |

Induction of and UBE2T-Derived Peptides-Specific CTLs with Cytotoxic Activity Against Cancer Cells CTL clones were induced that are specific to peptides derived from FOXM1- and UBE2T (Refs. 19-20; incorporated by reference in their entireties). Highly immunogenic FOXM1- and UBE2T-derived short peptides were identified (e.g., IYTWIEDHF (SEQ ID NO: 3) and RYPFEPPQI (SEQ ID NO: 13), respectively) that can induce HLA-A*24:02-restricted CTLs from PBMCs of healthy donors by interferon (IFN)-γ Enzyme-Linked ImmunoSpot (ELISPOT) assay. After obtaining CTLs clones by limiting dilution, it was confirmed that these FOXM1- and UBE2T-specific CTLs produced IFN-γ when they were exposed to antigen-presenting C1R cells expressing HLA-A*24:02 (C1R-A24 cells) stimulated with specific peptide-pulsed, while no or low IFN-γ production was detected without peptide-stimulation to C1R-A24 cells (FIG. 1A), indicating that established FOXM1- and UBE2T-specific CTLs specifically recognized HLA-A*24:02-restricted peptides.

Figure 1C:
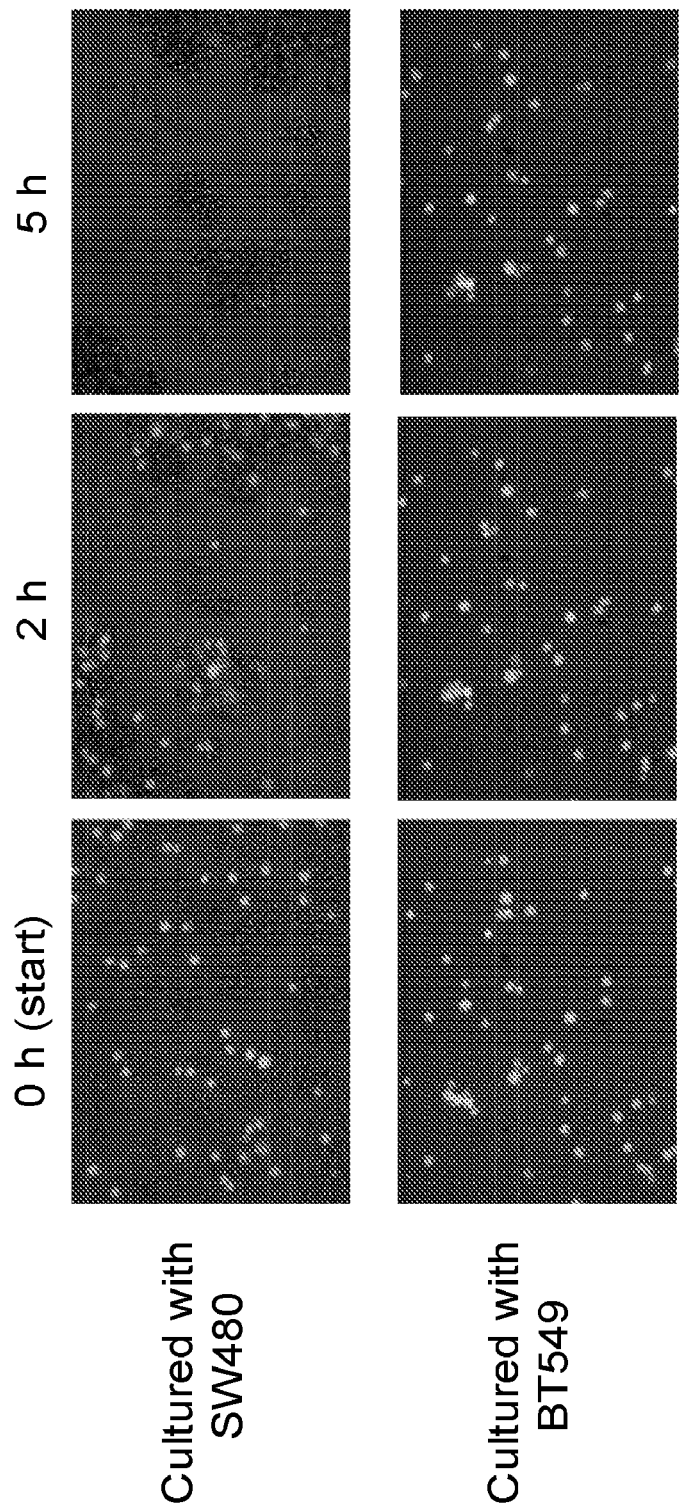
Figure 4:
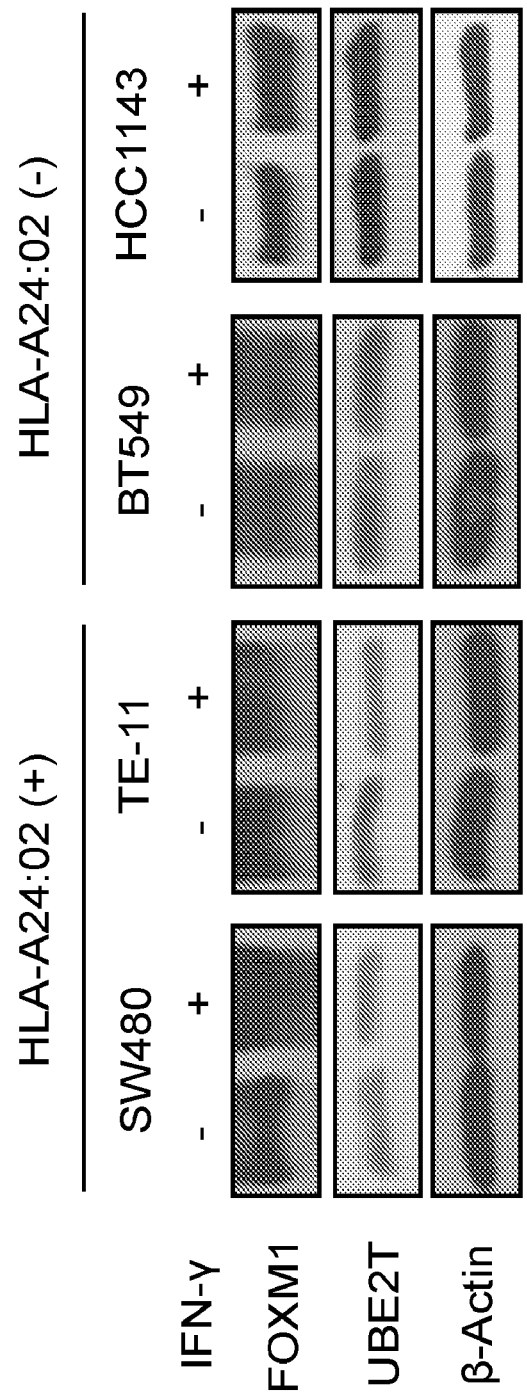
FIG. 4. FOXM1 and UBE2T protein expression in cancer cells. Expression of endogenous FOXM1 and UBE2T protein in HLA-A*24:02 positive or negative cancer cell lines examined by western blot analysis.

After examination of FOXM1 and UBE2T protein levels in cancer cell lines by western blot analysis (FIG. 4), cytotoxic activity of FOXM1- and UBE2Tspecific CTLs was examined against several cancer cell lines by a time-lapse recording system. FOXM1- and UBE2T-specific CTLs showed very strong cytotoxic activity against SW480 cells which expressed a high level of HLA-A24 as well as both FOXM1 and UBE2T proteins. Little cytotoxicity was observed against HLA-A24-negative cancer cell lines, HCC1143 and BT549 cells (FIGS. 1B and 1C). Results clearly indicated the HLA-restricted cytotoxic activity of antigen-specific T cells against cancer cells.

Generation of FOXM1- and UBE2T-Specific TCR-Engineered T Cells

Figure 2A:
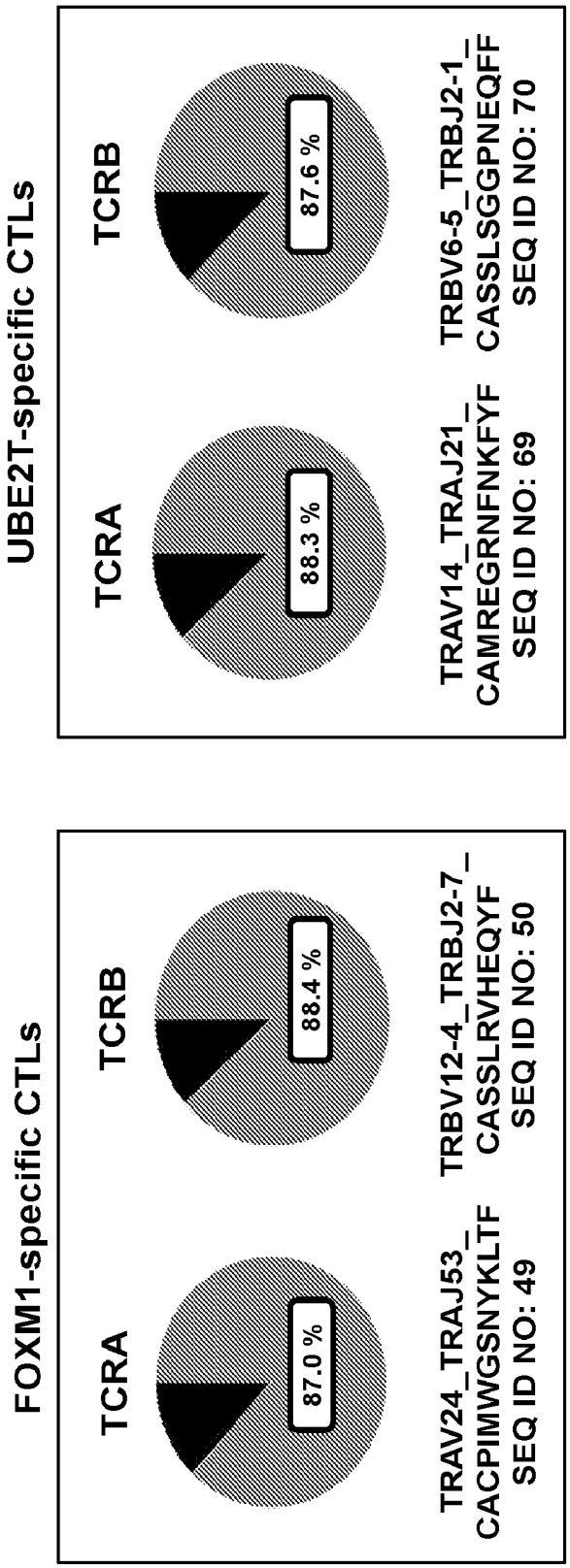
FIGS. 2A-B. Generation of TCR-engineered T cells for FOXM1 and UBE2T. (A) The distribution of TCRA and TCRB CDR3 clonotypes of FOXM1- and UBE2T-specific CTLs is presented in pie chart with CDR3 sequences. Black color indicates portion of CDR3 clonotypes below the read frequency of 1%. This population contained only one dominant clonotype for TCRA and TCRB. (B) The transduced efficiency was examined by staining for CD8 and TCRvβ8 (FOXM1 TCR-engineered T cells) or TCRvβ13 (UBE2T TCR-engineered T cells). Flow cytometry figures are representative of FOXM1- or UBE2T-TCR engineered T cells.

Subsequently, TCRA and TCRB chains of these FOXM1- and UBE2T-specific CTLs were sequenced by TCR repertoire analysis with next generation sequencing (FIG. 2A). Both of these CTL clones showed monoclonal TCR repertoire (FIG. 2A). Through DNA sequencing, dominant TCRA and TCRB CDR3 clonotypes were identified for FOXM1-

Figure 2B:
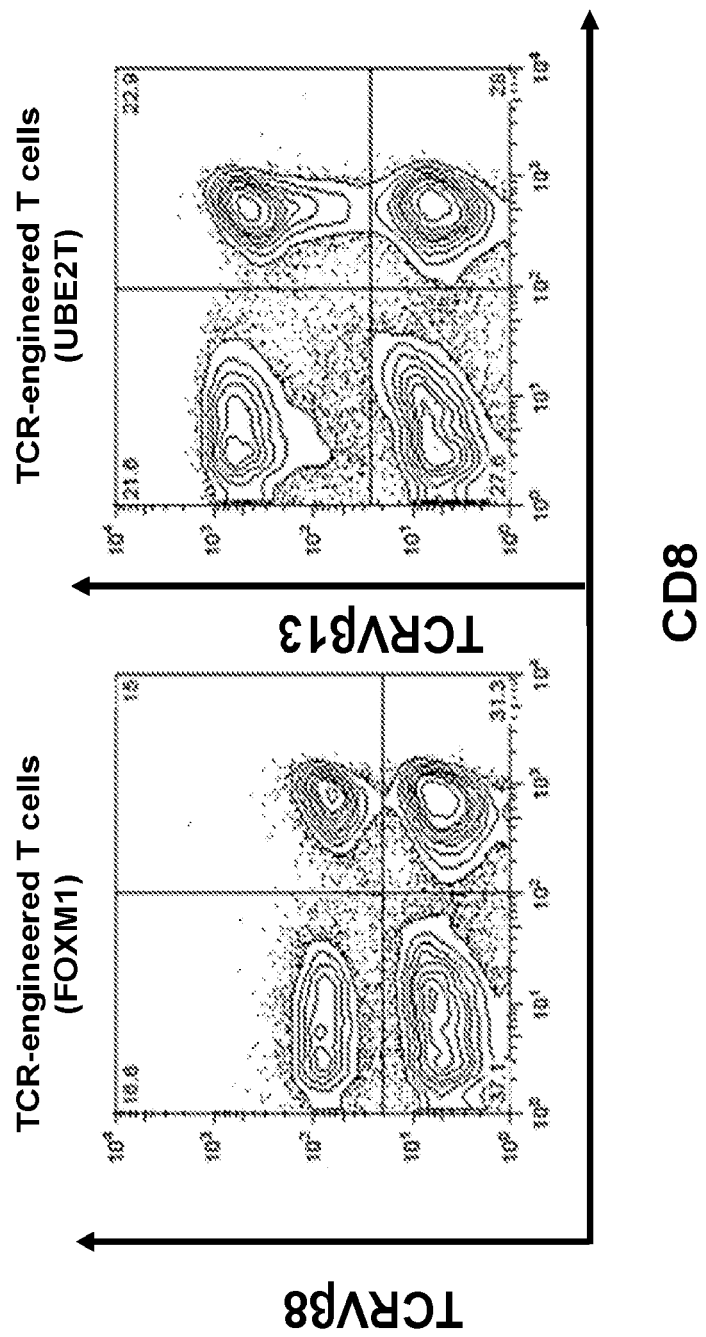

CTLs (CACPIMWGSNYKLTF (SEQ ID NO: 49) and CASSLRVHEQYF (SEQ ID NO: 50)) as well as in UBE2T-CTLs (CAMREGRNFNKFYF (SEQ ID NO: 69) and CASSLSGGPNEQFF (SEQ ID NO: 70)). TCR-expressing vector was constructed using cDNA information, cloned into the lenti virus vector, and generated TCR-engineered T cells recognizing FOXM1 and UBE2T. Transduction efficiency was measured by TCRvβ-specific antibodies (representative staining data was shown in FIG. 2B). For assays, only TCR-transduced cells were transduced.

Cytotoxic Activity of FOXM1 and UBE2T-Specific TCR-Engineered T Cells

Figure 3A:
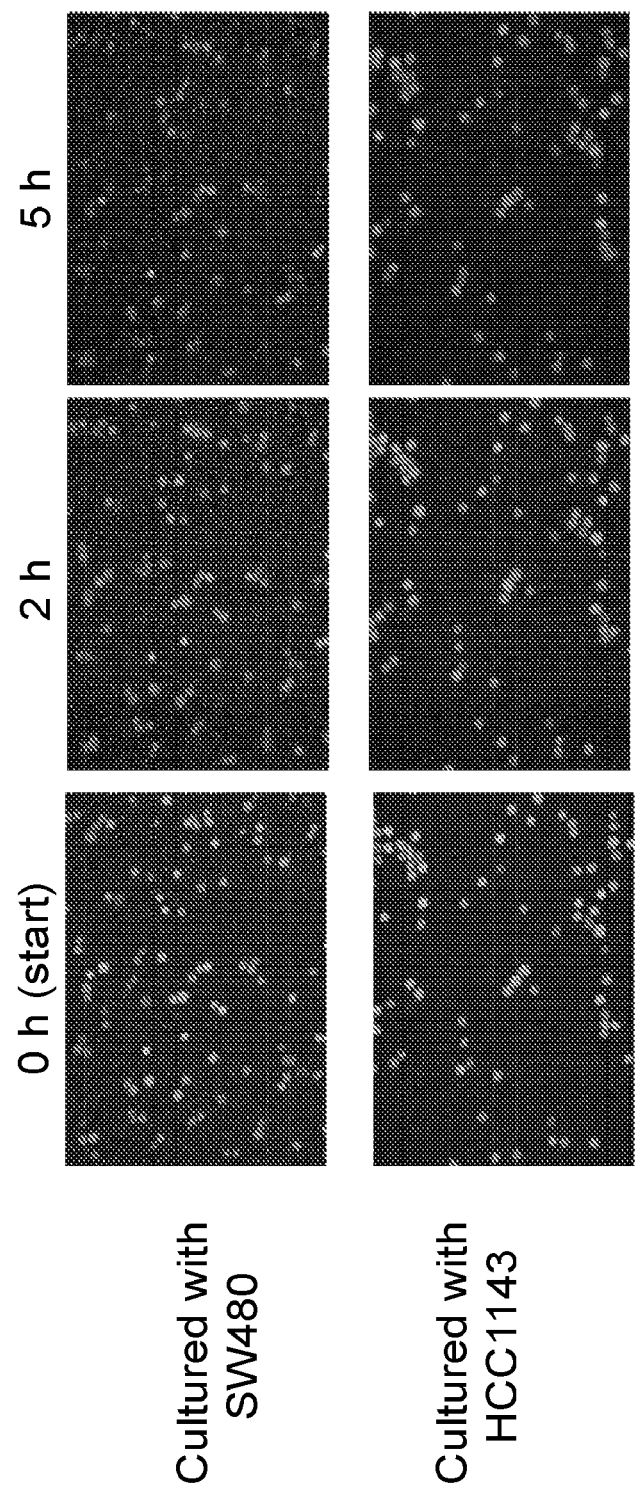
Figure 3C:
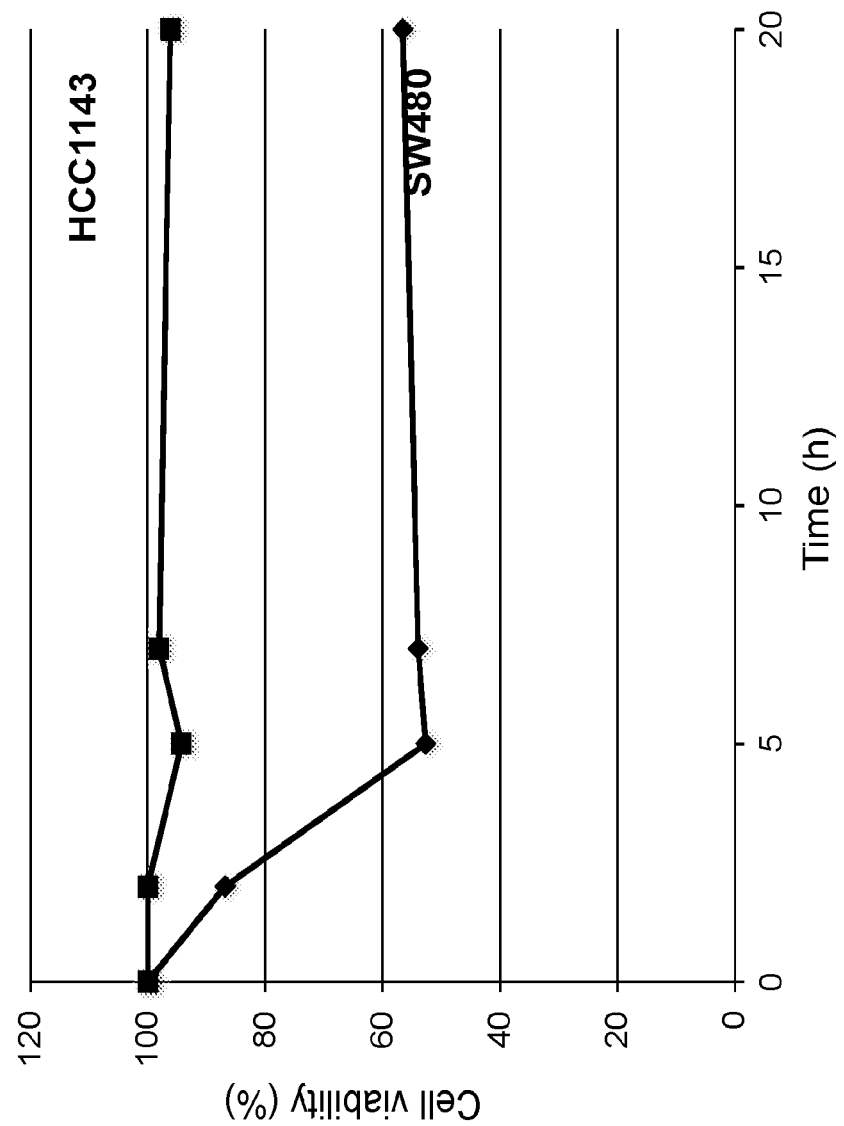
Figure 3D:
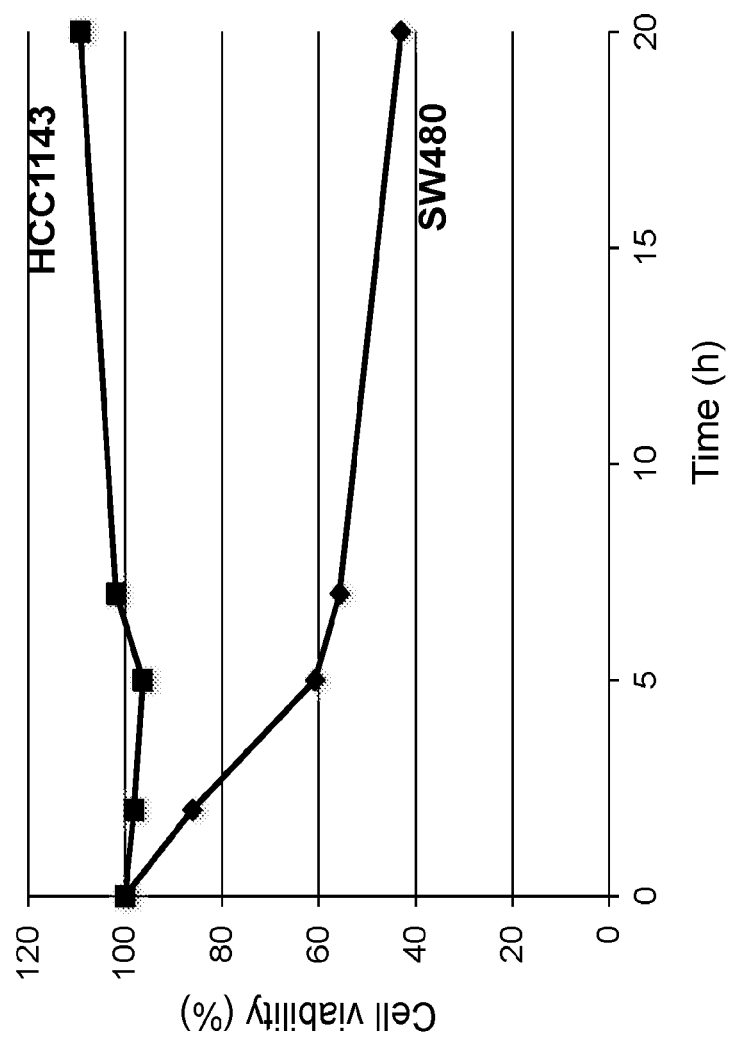
Figure 3G:
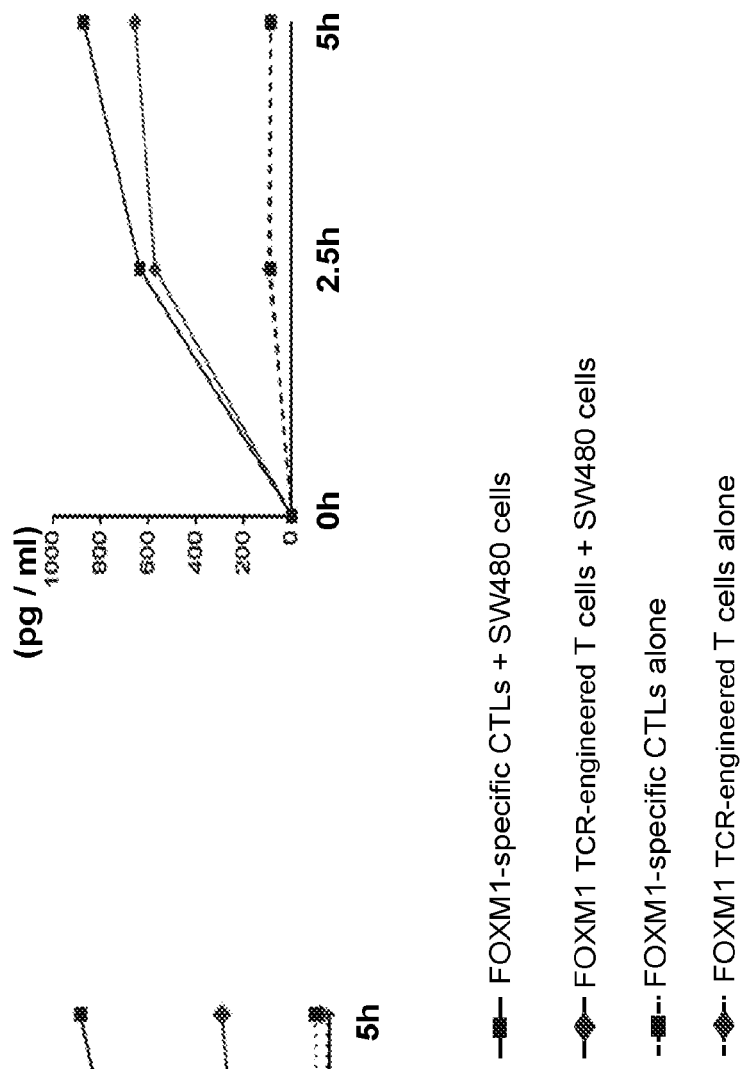

It was then assessed whether TCR-engineered T cells kill cancer cells as the original CTL clones as shown in FIGS. 1B and 1C. TCR-engineered T cells for FOXM1 and UBE2T exerted significant killing effects against HLA-A24-positive SW480 cells with the reduction of cell viability of 47.5% and 39.3% during first five hours, respectively, but not against HLA-A24-negative HCC1143 cells (FIG. 3A-3D). TCR-engineered T cells showed peptide-specific IFN-γ production in ELISPOT assay when co-cultured with C1R-A24 cells pulsed with respective peptides (FIGS. 3E and 3F).

REFERENCES

The following references, some of which are cited above by number, are incorporated by reference in their entireties.
1. Postow M A, Callahan M K, Wolchok J D. Immune Checkpoint Blockade in Cancer Therapy. J Clin Oncol. 2015; 33:1974-82.
2. Yarchoan M, Johnson B A 3rd, Lutz E R, Laheru D A, Jaffee E M. Targeting neoantigens to augment antitumour immunity. Nat Rev Cancer. 2017; 17:209-222.
3. Rizvi N A, Hellmann M D, Snyder A, Kvistborg P, Makarov V, Havel J J, Lee W, Yuan J, Wong P, Ho T S, Miller M L, Rekhtman N, Moreira A L, Ibrahim F, Bruggeman C, Gasmi B, Zappasodi R, Maeda Y, Sander C, Garon E B, Merghoub T, Wolchok J D, Schumacher T N, Chan T A. Cancer immunology. Mutational landscape determines sensitivity to PD-1 blockade in non-small cell lung cancer. Science. 2015; 348:124-8.
4. Topalian S L, Hodi F S, Brahmer J R, Gettinger S N, Smith D C, McDermott D F, Powderly J D, Carvajal R D, Sosman J A, Atkins M B, Leming P D, Spigel D R, Antonia S J, Horn L, Drake C G, Pardoll D M, Chen L, Sharfman W H, Anders R A, Taube J M, McMiller T L, Xu H, Korman A J, Jure-Kunkel M, Agrawal S, McDonald D, Kollia G D, Gupta A, Wigginton J M, Sznol M. Safety, activity, and immune correlates of anti-PD-1 antibody in cancer. N Engl J Med. 2012; 366:2443-54.
5. Rooney M S, Shukla S A, Wu C J, Getz G, Hacohen N. Molecular and genetic properties of tumors associated with local immune cytolytic activity. Cell. 2015; 160:48-61.
6. Tumeh P C, Harview C L, Yearley J H, Shintaku I P, Taylor E J, Robert L, Chmielowski B, Spasic M, Henry G, Ciobanu V, West A N, Carmona M, Kivork C, Seja E, Cherry G, Gutierrez A J, Grogan T R, Mateus C, Tomasic G, Glaspy J A, Emerson R O, Robins H, Pierce R H, Elashoff D A, Robert C, Ribas A. PD-1 blockade induces responses by inhibiting adaptive immune resistance. Nature. 2014; 515:568-71.
7. Schalper K A, Velcheti V, Carvajal D, Wimberly H, Brown J, Pusztai L, Rimm D L. In situ tumor PD-L1 mRNA expression is associated with increased TILs and better outcome in breast carcinomas. Clin Cancer Res. 2014; 20:2773-82.
8. Pardoll D M. The blockade of immune checkpoints in cancer immunotherapy. Nat Rev Cancer. 2012; 12:252-64.
9. Stevanović S, Pasetto A, Heiman S R, Gartner J J, Prickett T D, Howie B, Robins H S, Robbins P F, Klebanoff C A, Rosenberg S A, Hinrichs C S. Landscape of immunogenic tumor antigens in successful immunotherapy of virally induced epithelial cancer. Science. 2017; 356:200-205.
10. Coulie P G, Van den Eynde B J, van der Bruggen P, Boon T. Tumour antigens recognized by T lymphocytes: at the core of cancer immunotherapy. Nat Rev Cancer. 2014; 14:135-46.
11. Yoshitake Y, Fukuma D, Yuno A, Hirayama M, Nakayama H, Tanaka T, Nagata M, Takamune Y, Kawahara K, Nakagawa Y, Yoshida R, Hirosue A, Ogi H, Hiraki A, Jono H, Hamada A, Yoshida K, Nishimura Y, Nakamura Y, Shinohara M. Phase II clinical trial of multiple peptide vaccination for advanced head and neck cancer patients revealed induction of immune responses and improved OS. Clin Cancer Res. 2015; 21:312-21.
12. Hazama S, Nakamura Y, Tanaka H, Hirakawa K, Tahara K, Shimizu R, Ozasa H, Etoh R, Sugiura F, Okuno K, Furuya T, Nishimura T, Sakata K, Yoshimatsu K, Takenouchi H, Tsunedomi R, Inoue Y, Kanekiyo S, Shindo Y, Suzuki N, Yoshino S, Shinozaki H, Kamiya A, Furukawa H, Yamanaka T, Fujita T, Kawakami Y, Oka M. A phase II study of five peptides combination with oxaliplatin-based chemotherapy as a first-line therapy for advanced colorectal cancer (FXV study). J Transl Med. 2014; 12:108.
13. Kono K, Iinuma H, Akutsu Y, Tanaka H, Hayashi N, Uchikado Y, Noguchi T, Fujii H, Okinaka K, Fukushima R, Matsubara H, Ohira M, Baba H, Natsugoe S, Kitano S, Takeda K, Yoshida K, Tsunoda T, Nakamura Y. Multicenter, phase II clinical trial of cancer vaccination for advanced esophageal cancer with three peptides derived from novel cancer-testis antigens. J Transl Med. 2012; 10:141.
14. Tran E, Turcotte S, Gros A, Robbins P F, Lu Y C, Dudley M E, Wunderlich J R, Somerville R P, Hogan K, Hinrichs C S, Parkhurst M R, Yang J C, Rosenberg S A. Cancer immunotherapy based on mutation-specific CD4+ T cells in a patient with epithelial cancer. Science. 2014; 344: 641-5.
15. Tran E Robbins P F, Lu Y C, Prickett T D, Gartner J J, Jia L, Pasetto A, Zheng Z, Ray S, Groh E M, Kriley I R, Rosenberg S A. T-Cell Transfer Therapy Targeting Mutant KRAS in Cancer. N Engl J Med. 2016; 375:2255-2262.
16. Johnson L A, Morgan R A, Dudley M E, Cassard L, Yang J C, Hughes M S, Kammula U S, Royal R E, Sherry R M, Wunderlich J R, Lee C C, Restifo N P, Schwarz S L, Cogdill A P, Bishop R J, Kim H, Brewer C C, Rudy S F, VanWaes C, Davis J L, Mathur A, Ripley R T, Nathan D A, Laurencot C M, Rosenberg S A. Gene therapy with human and mouse T-cell receptors mediates cancer regression and targets normal tissues expressing cognate antigen. Blood. 2009; 114:535-46.
17. Robbins P F, Morgan R A, Feldman S A, Yang J C, Sherry R M, Dudley M E, Wunderlich J R, Nahvi A V, Helman L J, Mackall C L, Kammula U S, Hughes M S, Restifo N P, Raffeld M, Lee C C, Levy C L, Li Y F, El-Gamil M, Schwarz S L, Laurencot C, Rosenberg S A. Tumor regression in patients with metastatic synovial cell sarcoma and melanoma using genetically engineered lymphocytes reactive with NY-ESO-1. J Clin Oncol. 2011; 29:917-24.

18. Leisegang M, Engels B, Schreiber K, Yew P Y, Kiyotani K, Idel C, Arina A, Duraiswamy J, Weichselbaum R R, Uckert W, Nakamura Y, Schreiber H. Eradication of Large Solid Tumors by Gene Therapy with a T-Cell Receptor Targeting a Single Cancer-Specific Point Mutation. Clin Cancer Res. 2016; 22:2734-43.
19. Osawa R, Tsunoda T, Yoshimura S, Watanabe T, Miyazawa M, Tani M, Takeda K, Nakagawa H, Nakamura Y, Yamaue H. Identification of HLA-A24-restricted novel T Cell epitope peptides derived from P-cadherin and kinesin family member 20A. J Biomed Biotechnol. 2012; 2012: 848042.
20. Yoshimura S, Tsunoda T, Osawa R, Harada M, Watanabe T, Hikichi T, Katsuda M, Miyazawa M, Tani M, Iwahashi M, Takeda K, Katagiri T, Nakamura Y, Yamaue H. Identification of an HLA-A2-restricted epitope peptide derived from hypoxia-inducible protein 2 (HIG2). PLoS One. 2014; 9:e85267.
21. Rapoport A P, Stadtmauer E A, Binder-Scholl G K, Goloubeva O, Vogl D T, Lacey S F, Badros A Z, Garfall A, Weiss B, Finklestein J, Kulikovskaya I, Sinha S K, Kronsberg S, Gupta M, Bond S, Melchiori L, Brewer J E, Bennett A D, Gerry A B, Pumphrey N J, Williams D, Tayton-Martin H K, Ribeiro L, Holdich T, Yanovich S, Hardy N, Yared J, Kerr N, Philip S, Westphal S, Siegel D L, Levine B L, Jakobsen B K, Kalos M, June C H. NY-ESO-1-specific TCR-engineered T cells mediate sustained antigen-specific antitumor effects in myeloma. Nat Med. 2015; 21:914-921.
22. van der Bruggen P, Traversari C, Chomez P, Lurquin C, De Plaen E, Van den Eynde B, Knuth A, Boon T. A gene encoding an antigen recognized by cytolytic T lymphocytes on a human melanoma. Science. 1991; 254:1643-7.
23. Ishida Y, Agata Y, Shibahara K, Honjo T. Induced expression of PD-1, a novel member of the immunoglobulin gene superfamily, upon programmed cell death. EMBO J. 1992; 11:3887-95.
24. Krummel M F, Allison J P. CD28 and CTLA-4 have opposing effects on the response of T cells to stimulation. J Exp Med. 1995; 182:459-65.
25. Guo C, Manjili M H, Subjeck J R, Sarkar D, Fisher P B, Wang X Y. Therapeutic cancer vaccines: past, present, and future. Adv Cancer Res. 2013; 119:421-75.
26. Hinrichs C S, Rosenberg S A. Exploiting the curative potential of adoptive T-cell therapy for cancer. Immunol Rev. 2014; 257:56-71.
27. Dudley M E, Wunderlich J R, Robbins P F, Yang J C, Hwu P, Schwartzentruber D J, Topalian S L, Sherry R, Restifo N P, Hubicki A M, Robinson M R, Raffeld M, Duray P, Seipp C A, Rogers-Freezer L, Morton K E, Mavroukakis S A, White D E, Rosenberg S A. Cancer regression and autoimmunity in patients after clonal repopulation with antitumor lymphocytes. Science. 2002; 298:850-4.
28. Rosenberg S A, Yang J C, Sherry R M, Kammula U S, Hughes M S, Phan G Q, Citrin D E, Restifo N P, Robbins P F, Wunderlich J R, Morton K E, Laurencot C M, Steinberg S M, White D E, Dudley M E. Durable complete responses in heavily pretreated patients with metastatic melanoma using T-cell transfer immunotherapy. Clin Cancer Res. 2011; 17:4550-7.
29. Hodi F S, O'Day S J, McDermott D F, Weber R W, Sosman J A, Haanen J B, Gonzalez R, Robert C, Schadendorf D, Hassel J C, Akerley W, van den Eertwegh A J, Lutzky J, Lorigan P, Vaubel J M, Linette G P, Hogg D, Ottensmeier C H, Lebbe C, Peschel C, Quirt I, Clark J I, Wolchok J D, Weber J S, Tian J, Yellin M J, Nichol G M, Hoos A, Urba W J. Improved survival with ipilimumab in patients with metastatic melanoma. N Engl J Med. 2010; 363:711-23.
30. Stronen E, Toebes M, Kelderman S, van Buuren M M, Yang W, van Rooij N, Donia M, Boschen M L, Lund-Johansen F, Olweus J, Schumacher T N. Targeting of cancer neoantigens with donor-derived T cell receptor repertoires. Science. 2016; 352:1337-41.
31. Bektas N, Haaf At, Veeck J, Wild P J, Lüscher-FirzlaffJ, Hartmann A, Knüchel R, Dahl E. Tight correlation between expression of the Forkhead transcription factor FOXM1 and HER2 in human breast cancer. BMC Cancer. 2008; 8:42.
32. Weng W, Okugawa Y, Toden S, Toiyama Y, Kusunoki M, Goel A. FOXM1 and FOXQ1 Are Promising Prognostic Biomarkers and Novel Targets of Tumor-Suppressive miR-342 in Human Colorectal Cancer. Clin Cancer Res. 2016; 22:4947-4957.
33. Wen M, Kwon Y, Wang Y, Mao J H, Wei G. Elevated expression of UBE2T exhibits oncogenic properties in human prostate cancer. Oncotarget. 2015; 6:25226-39.
34. Yu H, Xiang P, Pan Q, Huang Y, Xie N, Zhu W. Ubiquitin-Conjugating Enzyme E2T is an Independent Prognostic Factor and Promotes Gastric Cancer Progression. Tumour Biol. 2016; 37:11723-11732.
35. Maude S L, Frey N, Shaw P A, Aplenc R, Barrett D M, Bunin N J, Chew A, Gonzalez V E, Zheng Z, Lacey S F, Mahnke Y D, Melenhorst J J, Rheingold S R, Shen A, Teachey D T, Levine B L, June C H, Porter D L, Grupp S A. Chimeric antigen receptor T cells for sustained remissions in leukemia. N Engl J Med. 2014; 371:1507-17.
36. Jackson H J, Rafiq S, Brentjens R J. Driving CAR T-cells forward. Nat Rev Clin Oncol. 2016; 13:370-83.
37. Uchida N, Tsunoda T, Wada S, Furukawa Y, Nakamura Y, Tahara H. Ring finger protein 43 as a new target for cancer immunotherapy. Clin Cancer Res. 2004; 10:8577-86.
38. Watanabe T, Suda T, Tsunoda T, Uchida N, Ura K, Kato T, Hasegawa S, Satoh S, Ohgi S, Tahara H, Furukawa Y, Nakamura Y. Identification of immunoglobulin superfamily 11 (IGSF11) as a novel target for cancer immunotherapy of gastrointestinal and hepatocellular carcinomas. Cancer Sci. 2005; 96:498-506.
39. Suda T, Tsunoda T, Uchida N, Watanabe T, Hasegawa S, Satoh S, Ohgi S, Furukawa Y, Nakamura Y, Tahara H. Identification of secernin 1 as a novel immunotherapy target for gastric cancer using the expression profiles of cDNA microarray. Cancer Sci. 2006; 97:411-9.
40. Riddell S R, Elliott M, Lewinsohn D A, Gilbert M J, Wilson L, Manley S A, Lupton S D, Overell R W, Reynolds T C, Corey L, Greenberg P D. T-cell mediated rejection of gene-modified HIV-specific cytotoxic T lymphocytes in HIV-infected patients. Nat Med. 1996; 2:216-23.
41. Fang H, Yamaguchi R, Liu X, Daigo Y, Yew P Y, Tanikawa C, Matsuda K, Imoto S, Miyano S, Nakamura Y. Quantitative T cell repertoire analysis by deep cDNA sequencing of T cell receptor α and β chains using next-generation sequencing (NGS). Oncoimmunology. 2015; 3:e968467.
42. Engels B, Chervin A S, Sant A J, Kranz D M, Schreiber H. Long-term persistence of CD4(+) but rapid disappearance of CD8(+) T cells expressing an MHC class I-restricted TCR of nanomolar affinity. Mol Ther. 2012; 20:652-60.

The invention claimed is:

1. A method comprising:
   (a) stimulating target lymphocytes with a stimulation peptide comprising a candidate antigen sequence;
   (b) capturing immune-active lymphocytes with T-cell receptor (TCR) that binds to the candidate peptide, wherein said capturing comprises contacting the immune-active lymphocytes with a capture reagent that displays major histocompatibility complex (MHC) bound to a capture peptide comprising the candidate antigen sequence;
   (c) sequencing all or a portion of the TCR of the captured immune-active lymphocytes; and
   (d) generating engineered lymphocytes displaying all or a portion of the TCR of the captured immune-active lymphocytes by:
      (i) cloning a nucleic acid sequence encoding the portion of the TCR of the captured immune-active lymphocytes into a vector,
      (ii) introducing the vector into host lymphocytes, and
      (iii) culturing the host lymphocytes under conditions such that the portion of the TCR of the captured immune-active lymphocytes is expressed and displayed on the engineered lymphocytes;
   wherein the engineered lymphocytes display a TCR comprising α and β chains comprising the amino acid sequence pairs selected from the group consisting of SEQ ID NOS: 45 and 46, 47 and 48, 49 and 50, 51 and 52, 53 and 54, 55 and 56, 57 and 58, 59 and 60, 61 and 62, 63 and 64, 65 and 66, 67 and 68, 69 and 70, 71 and 72, 73 and 74, 75 and 76, 77 and 78, 79 and 80, 81 and 82, 83 and 84, 85 and 86, 87 and 88, 89 and 90, 91 and 92, 93 and 94, 95 and 96, 97 and 98, 99 and 100, 101 and 102, 103 and 104, 105 and 106, 107 and 108, 109 and 110, 111 and 112, 113 and 114, 115 and 116, 117 and 118, 119 and 120, 121 and 122, 123 and 124, 125 and 126, 127 and 128, 129 and 130, and 131 and 132; and
   wherein the engineered lymphocytes recognize antigen presenting cells displaying MHC bound to the peptide comprising the candidate antigen sequence.

2. The method of claim 1, wherein the target lymphocytes are obtained from a healthy donor.

3. The method of claim 1, wherein the target lymphocytes are CD8+ cytotoxic lymphocytes.

4. The method of claim 1, wherein the stimulating is performed in vitro.

5. The method of claim 1, wherein the capture reagent is an MHC multimer.

6. The method of claim 1, wherein the portion of the TCR sequenced comprises one or more complementarity determining regions (CDRs) of the TCR-α and/or TCR-β chains.

7. The method of claim 1, wherein the target lymphocytes are a population of target lymphocytes, wherein the stimulation peptide is one of a population of stimulation peptides comprising different candidate antigen sequences; and
   wherein said capturing comprises contacting the population of immune-active lymphocytes with a capture reagents that displays major histocompatibility complex (MHC) bound to a population of capture peptides comprising the candidate antigen sequences.

8. The method of claim 1, wherein the engineered lymphocytes are CD8+ cytotoxic lymphocytes.

9. The method of claim 6, wherein the portion of the TCR sequenced comprises the CDR3 of the TCR-α and/or TCR-β chains.

10. The method of claim 1, wherein the vector is introduced into host lymphocytes from a healthy donor host or a cancer patient to be treated with the engineered lymphocytes.

11. Engineered lymphocytes produced by the method of claim 1.

* * * * *